United States Patent [19]
Lee et al.

[11] Patent Number: 5,945,526
[45] Date of Patent: *Aug. 31, 1999

[54] ENERGY TRANSFER DYES WITH ENHANCED FLUORESCENCE

[75] Inventors: Linda G. Lee, Palo Alto; Sandra L. Spurgeon, San Mateo; Barnett Rosenblum, San Jose, all of Calif.

[73] Assignee: Perkin-Elmer Corporation, Foster City, Calif.

[ * ] Notice: This patent is subject to a terminal disclaimer.

[21] Appl. No.: 09/046,203

[22] Filed: Mar. 23, 1998

Related U.S. Application Data

[63] Continuation-in-part of application No. 08/642,330, May 3, 1996, Pat. No. 5,863,727, and application No. 08/672,196, Jun. 27, 1996, Pat. No. 5,847,162.

[51] Int. Cl.$^6$ .................................................. C07H 21/04
[52] U.S. Cl. .................. 536/26.6; 536/24.33; 549/223
[58] Field of Search .............................. 536/26.6, 24.33; 435/6, 91.2; 549/223

[56] References Cited

U.S. PATENT DOCUMENTS

| | | | |
|---|---|---|---|
| 4,996,143 | 2/1991 | Heller et al. | 435/6 |
| 5,188,934 | 2/1993 | Menchen et al. | 435/6 |
| 5,607,834 | 3/1997 | Bagwell | 435/6 |
| 5,654,419 | 8/1997 | Mathies et al. | 536/25.4 |
| 5,688,648 | 11/1997 | Mathies et al. | 435/6 |

FOREIGN PATENT DOCUMENTS

| | | | |
|---|---|---|---|
| 0 201 751 A2 | 11/1986 | European Pat. Off. | C09B 11/08 |
| 0 229 943 A2 | 7/1987 | European Pat. Off. | C12Q 1/68 |
| 0 229 943 B1 | 7/1987 | European Pat. Off. | C12Q 1/68 |
| 0 747 700 A2 | 12/1996 | European Pat. Off. | G01N 33/533 |
| WO93/06482 | 4/1993 | WIPO | G01N 33/48 |
| WO93/13224 | 8/1993 | WIPO | C12Q 1/68 |
| WO95/21266 | 10/1995 | WIPO | C12Q 1/68 |
| WO96/04405 | 2/1996 | WIPO | C12Q 1/68 |
| WO96/30540 | 10/1996 | WIPO . | |
| WO97/11084 | 3/1997 | WIPO | C07H 21/00 |

OTHER PUBLICATIONS

Cardullo, R.A. et al., "Detection of nucleic acid hybridization by nonradiative fluorescence resonance energy transfer", Proc. Natl. Acad. Sci. USA, vol. 85, No. 23, Dec. 1988, pp. 8790–8794.

Clegg, R.M., "Fluorescence resonance energy transfer and nucleic acids", Methods Enzymol., vol. 211, (1992), pp. 353–388.

Haugland, Richard P., "Flurescence–Detected DNA Sequencing—Final Technical Report", Grant No. DE–FG06–88ER60684, Sep. 1990, 15 pages.

Cooper, J. et al., "Analysis of Fluorescence Energy Transfer in Duplex and Branched DNA Molecules" Biochemistry, vol. 29, No. 39, (1990), pp. 9261–9268.

Drake, J.M. et al., "Chemical and Biological Microstructures as Probed by Dynamic Processes", Science, vol. 251, pp. 1574–1579, Mar. 1991.

Ju, J. et al., "Design and synthesis of fluorescence energy transfer dye–labaled primers and their application for DNA sequencing and analysis", Anal. Biochem., vol. 231, No. 1, Oct. 10, 1995, pp. 131–140.

Ju, J. et al., "Fluorescence energy transfer dye–labeled primers for DNA sequencing and analysis", University of California Berkeley, Jan. 1995, pp. 4347–4350.

Lee, L.G. et. al., "Allelic discrimination by nick–translation PCR with fluorogenic probes", Nucleic Acids Res., vol. 21, No. 16, Aug. 11, 1993, pp. 3761–3766.

Lee, L.G. et al., "DNA sequencing with dye–labeled terminators and T7 DNA polymerase: effect of dyes and dNTPs on incorporation of dye–terminators and probability analysis of termination fragments", Nucleic Acids Res., vol. 20, No. 10, pp. 2471–2483 (1992).

Livak, K.J. et al., "Oligonucleotides with fluorescent dyes at opposite ends provide a quenched probe system useful for detecting PCR product and nucleic acid hybridization", PCR Methods Appl., vol. 4, No. 6, Jun. 1995, pp. 357–362.

Shipchandler, M.T. et al., "4'–[Aminomethyl]fluorescein and its N–alkyl derivatives: useful reagents in immunodiagnostic techniques", Anal. Biochem., vol. 162, No. 1, Apr. 1987, pp. 89–101.

Stenzel, R. et al., "Cross–Reactivity of Anti–Digoxin Antibodies with Digitoxin Depends on Tracer Structure", Clin. Chem., vol. 38, No. 11, (1992), pp. 2228–2232.

Stryer, L. et al., "Energy Transfer: A Spectroscopic Ruler", Proc. Natl. Acad. USA, vol. 58, (1967), pp. 719–726.

Hung, S. et al., "Cyanine Dyes with High Absorption Cross Section as Donor Chromophores in Energy Transfer Primers", Anal. Biochem., vol. 243, pp. 15–27, (1996).

Tyagi, S. et al., "Molecular Beacons: Probes that Fluoresce upon Hybridization", Nature Biotechnology, vol. 14, Mar. 1996, pp. 303–308.

Wu, P. et al., "Resonance energy transfer: methods and applications", Anal. Biochem., vol. 218, No. 1, Apr. 1994, pp. 1–13.

*Primary Examiner*—Scott W. Houtteman
*Attorney, Agent, or Firm*—Wilson, Sonsini, Goodrich & Rosati

[57] ABSTRACT

Novel linkers for linking a donor dye to an acceptor dye in an energy transfer fluorescent dye are provided. These linkers faciliate the efficient transfer of energy between a donor and acceptor dye in an energy transfer dye. One of these linkers for linking a donor dye to an acceptor dye in an energy transfer fluorescent dye has the general structure $R_{21}Z_1C(O)R_{22}R_{28}$ where $R_{21}$ is a $C_{1-5}$ alkyl attached to the donor dye, C(O) is a carbonyl group, $Z_1$ is either NH, sulfur or oxygen, $R_{22}$ is a substituent which includes an alkene, diene, alkyne, a five and six membered ring having at least one unsaturated bond or a fused ring structure which is attached to the carbonyl carbon, and $R_{28}$ includes a functional group which attaches the linker to the acceptor dye.

109 Claims, 16 Drawing Sheets

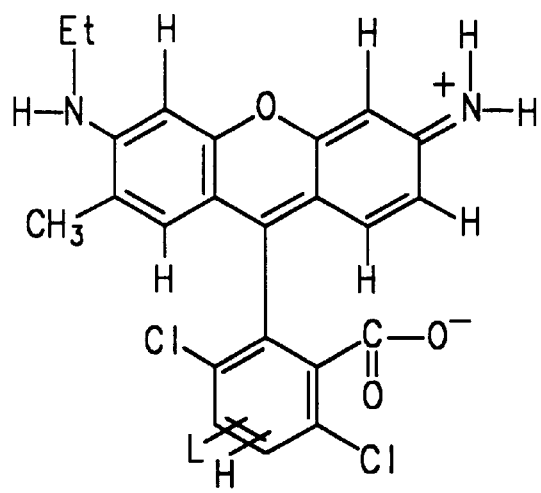
FIG. 3A-A
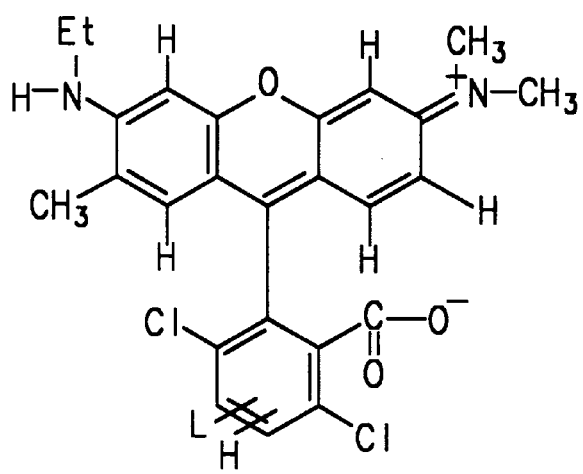
FIG. 3A-B
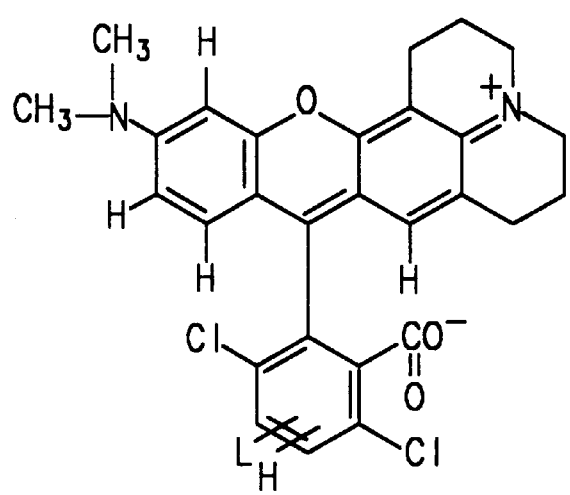
FIG. 3A-C

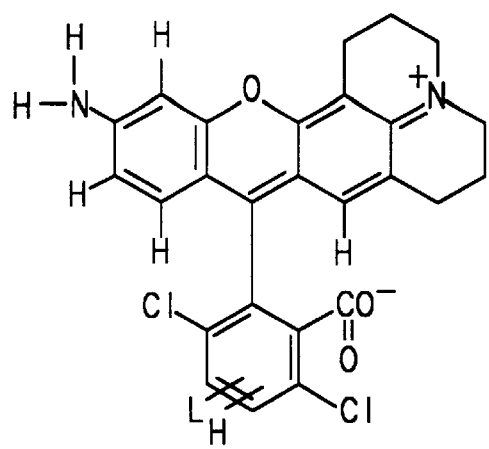
FIG. 3B-D
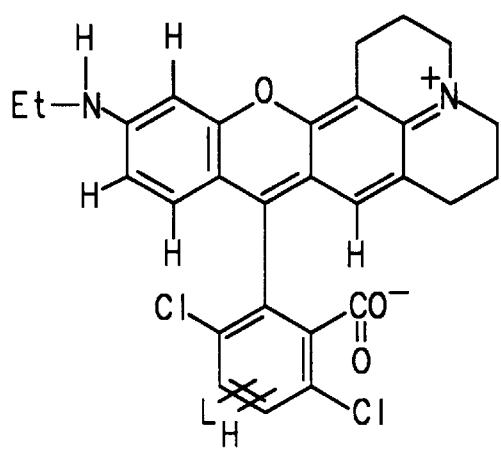
FIG. 3B-E
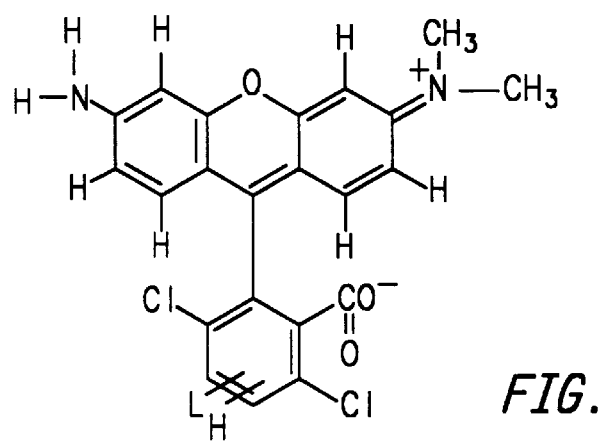
FIG. 3B-F

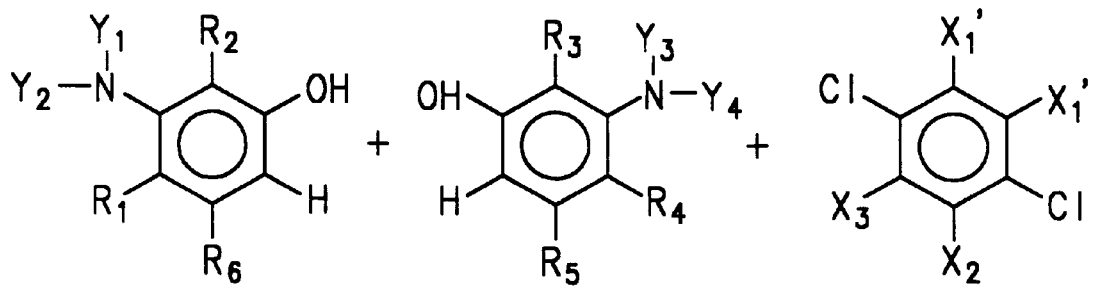
FIG. 4A-A  FIG. 4A-B  FIG. 4A-C
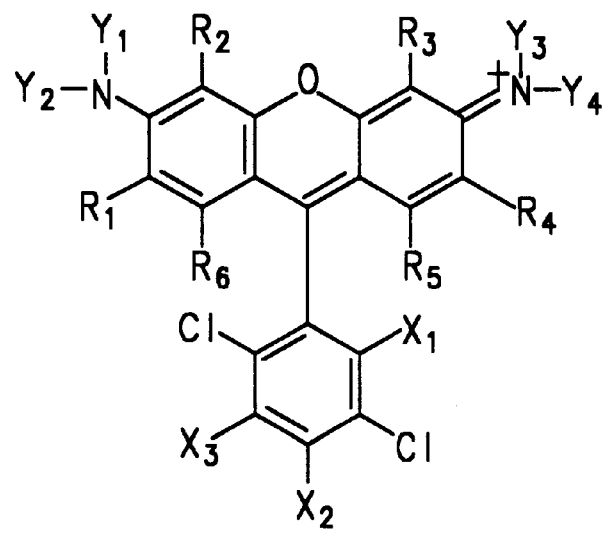
FIG. 4A-D

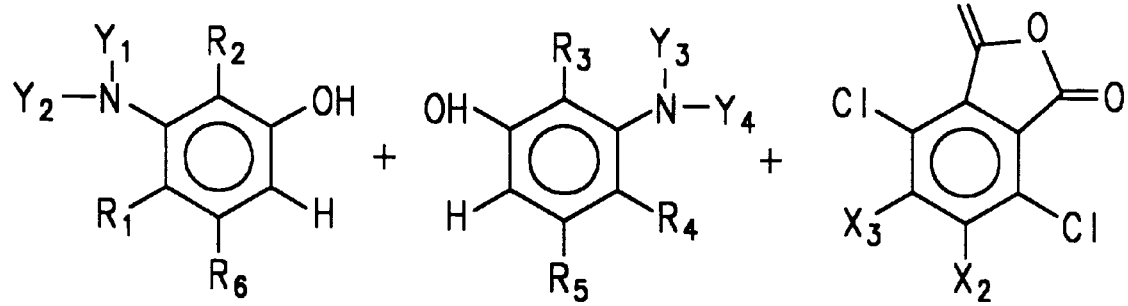
FIG. 4B-A    FIG. 4B-B    FIG. 4B-E
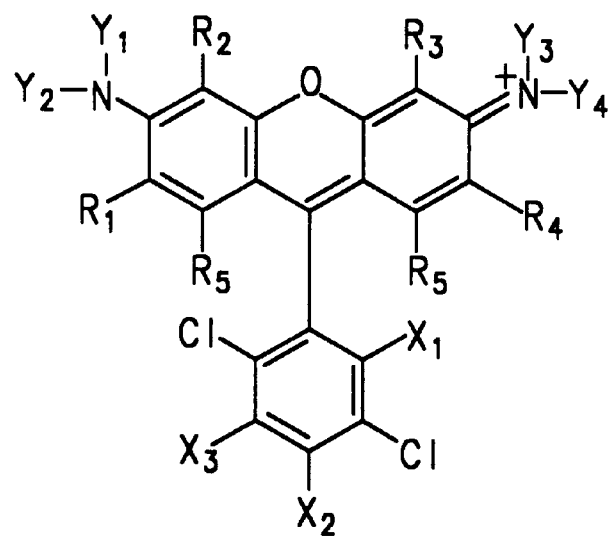
FIG. 4B-D

ENERGY TRANSFER DYES WITH ENHANCED FLUORESCENCE

RELATIONSHIP TO COPENDING APPLICATIONS

This application is a continuation-in-part of "ENERGY TRANSFER DYES WITH ENHANCED FLUORESCENCE," application Ser. No.: 08/642,330; Filed: May 3, 1996 now U.S. Pat. No. 5,863,727 and U.S. application Ser. No.: 08/672,196; filed: Jun. 27, 1996; now U.S. Pat. No. 5,847,162 entitled: "4,7-DICHLORORHODAMINE DYES" which are incorporated herein by reference.

BACKGROUND OF THE INVENTION

1. Field of the Invention

The present invention relates to fluorescent dyes and, more specifically, energy transfer fluorescent dyes and their use.

2. Description of Related Art

A variety of fluorescent dyes have been developed for labeling and detecting components in a sample. In general, fluorescent dyes preferably have a high quantum yield and a large extinction coefficient so that the dye may be used to detect small quantities of the component being detected. Fluorescent dyes also preferably have a large Stokes shift (i.e., the difference between the wavelength at which the dye has maximum absorbance and the wavelength at which the dye has maximum emission) so that the fluorescent emission is readily distinguished from the light source used to excite the dye.

One class of fluorescent dyes which has been developed is energy transfer fluorescent dyes. In general, energy transfer fluorescent dyes include a donor fluorophore and an acceptor fluorophore. In these dyes, when the donor and acceptor fluorophores are positioned in proximity with each other and with the proper orientation relative to each other, the energy emission from the donor fluorophore is absorbed by the acceptor fluorophore and causes the acceptor fluorophore to fluoresce. It is therefore important that the excited donor fluorophore be able to efficiently absorb the excitation energy of the donor fluorophore and efficiently transfer the energy to the acceptor fluorophore.

A variety of energy transfer fluorescent dyes have been described in the literature. For example, U.S. Pat. No. 4,996,143 and WO 95/21266 describe energy transfer fluorescent dyes where the donor and acceptor fluorophores are linked by an oligonucleotide chain. Lee, et al., *Nucleic Acids Research* 20:10 2471–2483 (1992) describes an energy transfer fluorescent dye which includes 5-carboxy rhodamine linked to 4'-aminomethyl-5-carboxy fluorescein by the 4'-aminomethyl substituent on fluorescein.

Several diagnostic and analytical assays have been developed which involve the detection of multiple components in a sample using fluorescent dyes, e.g. flow cytometry (Lanier, et al., *J. Immunol.* 132 151–156 (1984)); chromosome analysis (Gray, et al., *Chromosoma* 73 9–27 (1979)); and DNA sequencing. For these assays, it is desirable to simultaneously employ a set of two or more spectrally resolvable fluorescent dyes so that more than one target substance can be detected in the sample at the same time. Simultaneous detection of multiple components in a sample using multiple dyes reduces the time required to serially detect individual components in a sample. In the case of multi-loci DNA probe assays, the use of multiple spectrally resolvable fluorescent dyes reduces the number of reaction tubes that are needed, thereby simplifying the experimental protocols and facilitating the manufacturing of application-specific kits. In the case of automated DNA sequencing, the use of multiple spectrally resolvable fluorescent dyes allows for the analysis of all four bases in a single lane thereby increasing throughput over single-color methods and eliminating uncertainties associated with inter-lane electrophoretic mobility variations. Connell, et al., *Biotechniques* 5 342–348 (1987); Prober, et al., *Science* 238 336–341 (1987), Smith, et al., *Nature* 321 674–679 (1986); and Ansorge, et al., *Nucleic Acids Research* 15 4593–4602 (1989).

There are several difficulties associated with obtaining a set of fluorescent dyes for simultaneously detecting multiple target substances in a sample, particularly for analyses requiring an electrophoretic separation and treatment with enzymes, e.g., DNA sequencing. For example, each dye in the set must be spectrally resolvable from the other dyes. It is difficult to find a collection of dyes whose emission spectra are spectrally resolved, since the typical emission band halfwidth for organic fluorescent dyes is about 40–80 nanometers (nm) and the width of the available spectrum is limited by the excitation light source. As used herein the term "spectral resolution" in reference to a set of dyes means that the fluorescent emission bands of the dyes are sufficiently distinct, i.e., sufficiently non-overlapping, that reagents to which the respective dyes are attached, e.g. polynucleotides, can be distinguished on the basis of the fluorescent signal generated by the respective dyes using standard photodetection systems, e.g. employing a system of band pass filters and photomultiplier tubes, charged-coupled devices and spectrographs, or the like, as exemplified by the systems described in U.S. Pat. Nos. 4,230,558, 4,811,218, or in Wheeless et al, pgs. 21–76, in *Flow Cytometry: Instrumentation and Data Analysis* (Academic Press, New York, 1985).

The fluorescent signal of each of the dyes must also be sufficiently strong so that each component can be detected with sufficient sensitivity. For example, in the case of DNA sequencing, increased sample loading can not compensate for low fluorescence efficiencies, Pringle et al., *DNA Core Facilities Newsletter,* 1 15–21 (1988). The fluorescent signal generated by a dye is generally greatest when the dye is excited at its absorbance maximum. It is therefore preferred that each dye be excited at about its absorbance maximum.

A further difficulty associated with the use of a set of dyes is that the dyes generally do not have the same absorbance maximum. When a set of dyes are used which do not have the same absorbance maximum, a trade off is created between the higher cost associated with providing multiple light sources to excite each dye at its absorbance maximum, and the lower sensitivity arising from each dye not being excited at its absorbance maximum.

In addition to the above difficulties, the charge, molecular size, and conformation of the dyes must not adversely affect the electrophoretic mobilities of the fragments. The fluorescent dyes must also be compatible with the chemistry used to create or manipulate the fragments, e.g., DNA synthesis solvents and reagents, buffers, polymerase enzymes, ligase enzymes, and the like.

Because of the multiple constraints on developing a set of dyes for multicolor applications, particularly in the area of four color DNA sequencing, only a few sets of fluorescent dyes have been developed. Connell, et al., *Biotechniques* 5 342–348 (1987); Prober, et al., *Science* 238 336–341 (1987); and Smith, et al., *Nature* 321 674–679 (1986).

One class of fluorescent dyes that has been found to be useful in multicolor applications are rhodamine dyes, e.g., tetramethylrhodamine (TAMRA), rhodamine X (ROX), rhodamine 6G (R6G), rhodamine 110 (R110), and the like. U.S. Pat. No. 5,366,860. Rhodamine dyes are particularly attractive relative to fluorescein dyes because (1) rhodamines are typically more photostable than fluoresceins, (2) rhodamine-labeled dideoxynucleotides are better substrates for thermostable polymerase enzymes, and (3) the emission spectra of rhodamine dyes is significantly to the red (higher wavelength) of fluoresceins.

One drawback associated with currently available rhodamine dyes, particularly in the context of multiplex detection methods, is the relatively broad emission spectrum of the rhodamine dyes. This broad emission spectrum limits spectral resolution between spectrally neighboring dyes, making the multicomponent analysis of such dye combinations difficult. A second drawback associated with currently available rhodamine dyes is that their absorption spectrum does not match the wavelength of currently available solid state frequency-doubled green diode lasers, e.g., neodymium solid-state YAG lasers, which have an emission line at approximately 532 nm. It is highly advantageous to use such lasers because of their compact size, long useful life, and efficient use of power.

Energy transfer fluorescent dyes possess several features which make them attractive for use in the simultaneous detection of multiple target substances in a sample, such as in DNA sequencing. For example, a single donor fluorophore can be used in a set of energy transfer fluorescent dyes so that each dye has strong absorption at a common wavelength. Then, by varying the acceptor fluorophore in the energy transfer dye, a series of energy transfer dyes having spectrally resolvable fluorescence emissions can be generated.

Energy transfer fluorescent dyes also provide a larger effective Stokes shift than non-energy transfer fluorescent dyes. This is because the Stokes shift for an energy transfer fluorescent dye is based on the difference between the wavelength at which the donor fluorophore maximally absorbs light and the wavelength at which the acceptor fluorophore maximally emits light. In general, a need exists for fluorescent dyes having larger Stokes shifts.

The sensitivity of any assay using a fluorescent dye is dependent on the strength of the fluorescent signal generated by the fluorescent dye. A need therefore exists for fluorescent dyes which have a strong fluorescence signal. With regard to energy transfer fluorescent dyes, the fluorescence signal strength of these dyes is dependent on how efficiently the acceptor fluorophore absorbs the energy emission of the donor fluorophore. This, in turn, depends on a variety of variables, including the proximity of the donor fluorophore to the acceptor fluorophore and the orientation of the donor fluorophore relative to the acceptor fluorophore. A need therefore exists for energy transfer fluorescent dyes in which the orientation between the donor and acceptor fluorophore is such that energy is efficiently transferred between the donor and acceptor fluorophore.

SUMMARY OF THE INVENTION

The present invention relates to linkers for linking a donor dye to an acceptor dye in an energy transfer fluorescent dye. The present invention also relates to energy transfer fluorescent dyes having enhanced fluorescence. The present invention also relates to reagents which include the energy transfer dyes of the present invention, methods for using the dyes and reagents, and kits within which the dyes and reagents are included.

One linker according to the present invention for linking a donor dye to an acceptor dye in an energy transfer fluorescent dye has the general structure $R_{21}Z_1C(O)R_{22}R_{28}$, as illustrated below, where $R_{21}$ is a $C_{1-5}$ alkyl attached to the donor dye, $C(O)$ is a carbonyl group, $Z_1$ is either NH, sulfur or oxygen, $R_{22}$ is a substituent attached to the carbonyl carbon which may be either an alkene, diene, alkyne, a five or six membered ring having at least one unsaturated bond or a fused ring structure, and $R_{28}$ includes a functional group which attaches the linker to the acceptor dye.

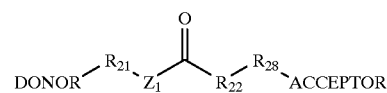

The $R_{28}$ group used in the linker may be any group known in the art which can be used to attach the $R_{22}$, group to an acceptor dye. Typically, the $R_{28}$ group will be attached to a benzene ring or other aromatic ring structure on the acceptor dye. Accordingly, $R_{28}$ is preferably formed by forming an electrophilic functional group on the benzene ring or other aromatic ring structure of the acceptor dye, such as a carboxylic acids, acid halide, sulfonic acid, ester, aldehyde, thio, disulfide, isothiocyanate, isocyanate, sulfonyl halide, maleimide, hydroxysuccinimide ester, haloacetyl, hydroxysulfosuccinimide ester, imido ester, hydrazine, azidonitrophenyl, and azide. The $R_{22}$ group can then be added to the acceptor dye, either before or after attachment of the donor dye to the $R_{22}$ group, by reacting the electrophilic agent on the acceptor dye with a nucleophile, such as an amino, hydroxyl or sulfhydryl nucleophile.

For example, in the embodiment illustrated below, the linker has the general structure $R_{21}Z_1C(O)R_{22}R_{22}Z_2C(O)$ where $R_{21}$ and $R_{22}$ are as detailed above, $Z_1$ and $Z_2$ are each independently either NH, sulfur or oxygen, and $R_{29}$ is a $C_{1-5}$ alkyl, and the terminal carbonyl group is attached to the ring structure of the acceptor dye. In the variation where $Z_2$ is nitrogen, the $C(O)R_{22}R_{21}Z_2$ subunit forms an amino acid subunit.

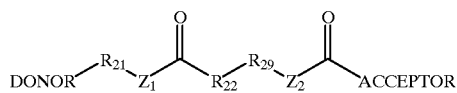

In this embodiment, the linker may be formed by the reaction of an activated carbonyl group (NHS ester) with a amine, hydroxyl or thiol group. It is noted that a wide variety of other mechanisms for attaching an $R_{22}$ group to an acceptor dye are envisaged and are intended to fall within the scope of the invention.

Particular examples of five or six membered rings which may be used as $R_{22}$ in the linker include, but are not limited to cyclopentene, cyclohexene, cyclopentadiene, cyclohexadiene, furan, thiofuran, pyrrole, isopyrole, isoazole, pyrazole, isoimidazole, pyran, pyrone, benzene, pyridine, pyridazine, pyrimidine, pyrazine and oxazine. Examples of fused ring structures include, but are not limited to indene, benzofuran, thionaphthene, indole and naphthalene.

A preferred embodiment of this linker is where $R_2$, and $R_{29}$ are methylene, $Z_1$ and $Z_2$ are NH, and $R_{22}$ is benzene, as shown below.

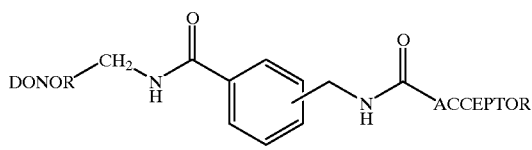

One class of energy transfer fluorescent dyes according to the present invention includes a donor dye which has the following xanthene ring structure with a 4' ring position

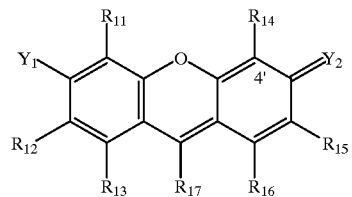

where $Y_1$ and $Y_2$ taken separately are either hydroxyl, oxygen, iminium or amine, the iminium and amine preferably being a tertiary iminium or amine. $R_{11}-R_{17}$ may be any substituent which is compatible with the energy transfer dyes of the present invention, it being noted that the $R_{11}-R_{17}$ may be widely varied in order to alter the spectral and mobility properties of the dyes.

According to this embodiment, the energy transfer dye also includes an acceptor dye which absorbs the excitation energy emitted by the donor dye and fluoresces at a second wavelength in response. The energy transfer dye also includes a linker which attaches the donor dye to the acceptor dye.

In one variation of this embodiment of energy transfer dyes, the linker has the general structure $R_{21}Z_1C(O)R_{22}R_{28}$, as illustrated above, where $R_{21}$ is a $C_{1-5}$ alkyl attached to the 4' position of the xanthene donor dye, C(O) is a carbonyl group, $Z_1$ is either NH, sulfur or oxygen, $R_{22}$ is a substituent attached to the carbonyl carbon which may be either an alkene, diene, alkyne, a five or six membered ring having at least one unsaturated bond or a fused ring structure, and $R_{28}$ includes a functional group which attaches the linker to the acceptor dye.

In a further variation of this embodiment of energy transfer dyes, the linker has the general structure $R_{21}Z_1C(O)R_{22}R_{29}Z_2C(O)$, as illustrated above, where $R_{21}$ and $R_{22}$ are as detailed above, $Z_1$ and $Z_2$ are each independently either NH, sulfur or oxygen, and $R_{29}$ is a $C_{1-5}$ alkyl, and the terminal carbonyl group is attached to the ring structure of the acceptor dye. In the variation where $Z_2$ is nitrogen, —$C(O)R_{22}R_{29}Z_2$— forms an amino acid subunit.

In a further preferred variation of this embodiment of energy transfer dyes, the linker is where $R_2$, and $R_{29}$ are methylene, $Z_1$ and $Z_2$ are NH, and $R_{22}$ is benzene, as shown below.

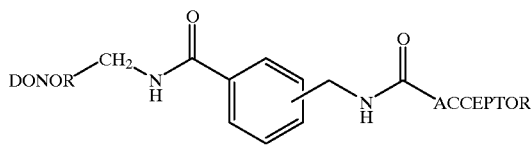

The donor dye may optionally be a member of the class of dyes where $R_{17}$ is a phenyl or substituted phenyl. When $Y_1$ is hydroxyl and $Y_2$ is oxygen, and $R_{17}$ is a phenyl or substituted phenyl, the dye is a member of the fluorescein class of dyes. When $Y_1$ is amine and $Y_2$ is iminium, and $R_{17}$ is a phenyl or substituted phenyl, the dye is a member of the rhodamine class of dyes. Further according to this embodiment, the acceptor dye may optionally be a member of the xanthene, cyanine, phthalocyanine and squaraine classes of dyes.

In another embodiment, the energy transfer fluorescent dyes have donor and acceptor dyes with the general structure

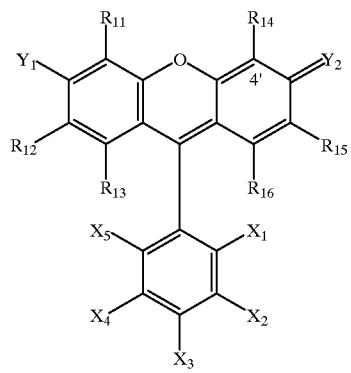

where $Y_1$ and $Y_2$ taken separately are either hydroxyl, oxygen, iminium or amine, the iminium and amine preferably being a tertiary iminium or amine and $R_{11}-R_{16}$ are any substituents which are compatible with the energy transfer dyes of the present invention.

According to this embodiment, as illustrated below, the linker is attached to one of $X_3$ and $X_4$ substituents of each of the donor and acceptor dyes, preferably the $X_3$ substituents of the donor and acceptor dyes. In this embodiment, the linker is preferably short and/or rigid as this has been found to enhance the transfer of energy between the donor and acceptor dyes.

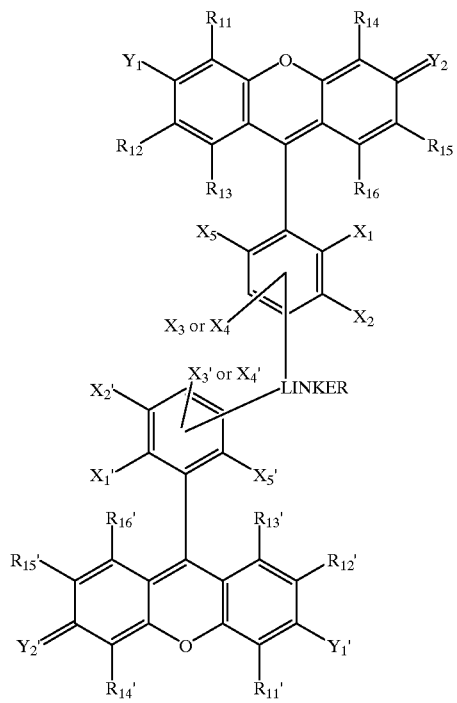

In another embodiment, the energy transfer fluorescent dyes include a donor dye which is a member of the xanthene class of dyes, an acceptor dye which is a member of the xanthene, cyanine, phthalocyanine and squaraine classes of dyes which is capable of absorbing the excitation energy emitted by the donor dye and fluorescing at a second wavelength in response, and a linker attaching the donor dye to the acceptor dye. According to this embodiment, the acceptor has an emission maximum that is greater than about 600 nm or at least about 100 nm greater than the absorbance maximum of the donor dye.

In addition to the above-described novel energy transfer fluorescent dyes, the present invention also relates to fluorescent reagents containing the energy transfer fluorescent dyes. In general, these reagents include any molecule or material to which the energy transfer dyes of the invention can be attached and used to detect the presence of the reagent based on the fluorescence of the energy transfer dye. In one embodiment, a fluorescent reagent is provided which includes a nucleoside or a mono-, di- or triphosphate nucleotide labeled with an energy transfer fluorescent dye. The nucleotide may be a deoxynucleotide which may be used for example, in the preparation of dye labeled oligonucleotides. The nucleotide may also be a dideoxynucleoside which may be used, for example, in dye terminator sequencing. In another embodiment, the fluorescent reagent includes an oligonucleotide labeled with an energy transfer fluorescent dye. These reagents may be used, for example, in dye primer sequencing.

The present invention also relates to methods which use the energy transfer fluorescent dyes and reagents of the present invention. In one embodiment, the method includes forming a series of different sized oligonucleotides labeled with an energy transfer fluorescent dye of the present invention, separating the series of labeled oligonucleotides based on size, detecting the separated labeled oligonucleotides based on the fluorescence of the energy transfer dye.

In one embodiment of this method, a mixture of extended labeled primers is formed by hybridizing a nucleic acid sequence with an oligonucleotide primer in the presence of deoxynucleotide triphosphates, and at least one dye labeled dideoxynucleotide triphosphate and a DNA polymerase. The DNA polymerase serves to extend the primer with the deoxynucleotide triphosphates until a dideoxynucleotide triphosphate is incorporated which terminates extension of the primer. Once terminated, the mixture of extended primers are separated and detected based on the fluorescence of the dye on the dideoxynucleoside. In a variation of this embodiment, four different fluorescently labeled dideoxynucleotide triphosphates are used, i.e., a fluorescently labeled dideoxycytosine triphosphate, a fluorescently labeled dideoxyadenosine triphosphate, a fluorescently labeled dideoxyguanosine triphosphate, and a fluorescently labeled dideoxythymidine triphosphate. In an alternate embodiment of this method, the oligonucleotide primer is fluorescently labeled as opposed to the deoxynucleotide triphosphate.

The present invention also relates to kits containing the dyes and reagents for performing DNA sequencing using the dyes and reagents of present invention.

BRIEF DESCRIPTION OF THE FIGURES

FIGS. 3A and 3B show several particularly preferred embodiments of 4,7-dichlororhodamine dye compounds which can be used in the energy transfer dyes of the present invention.

FIGS. 4A and 4B show preferred generalized synthesis schemes for the preparation of the 4,7-dichlororhodamine dyes of the invention.

FIG. 4A shows a generalized synthesis wherein the substituent $X_1$ can be other than carboxylate.

FIG. 4B shows a generalized synthesis wherein the substituent $X_1$ is carboxylate.

FIG. 9A provides the overlaid spectra of 6-CFB-DR110-2 and DR110-2.

FIG. 9B provides an overlaid spectra of 5-CFB-DR6G-2 and DR6G-2.

FIG. 9C provides an overlaid spectra of 6-CFB-DTMR-2 and DTMR-2.

FIG. 9D provides an overlaid spectra of 6-CFB-DROX-2 and DROX-2.

DETAILED DESCRIPTION

Figure 1:
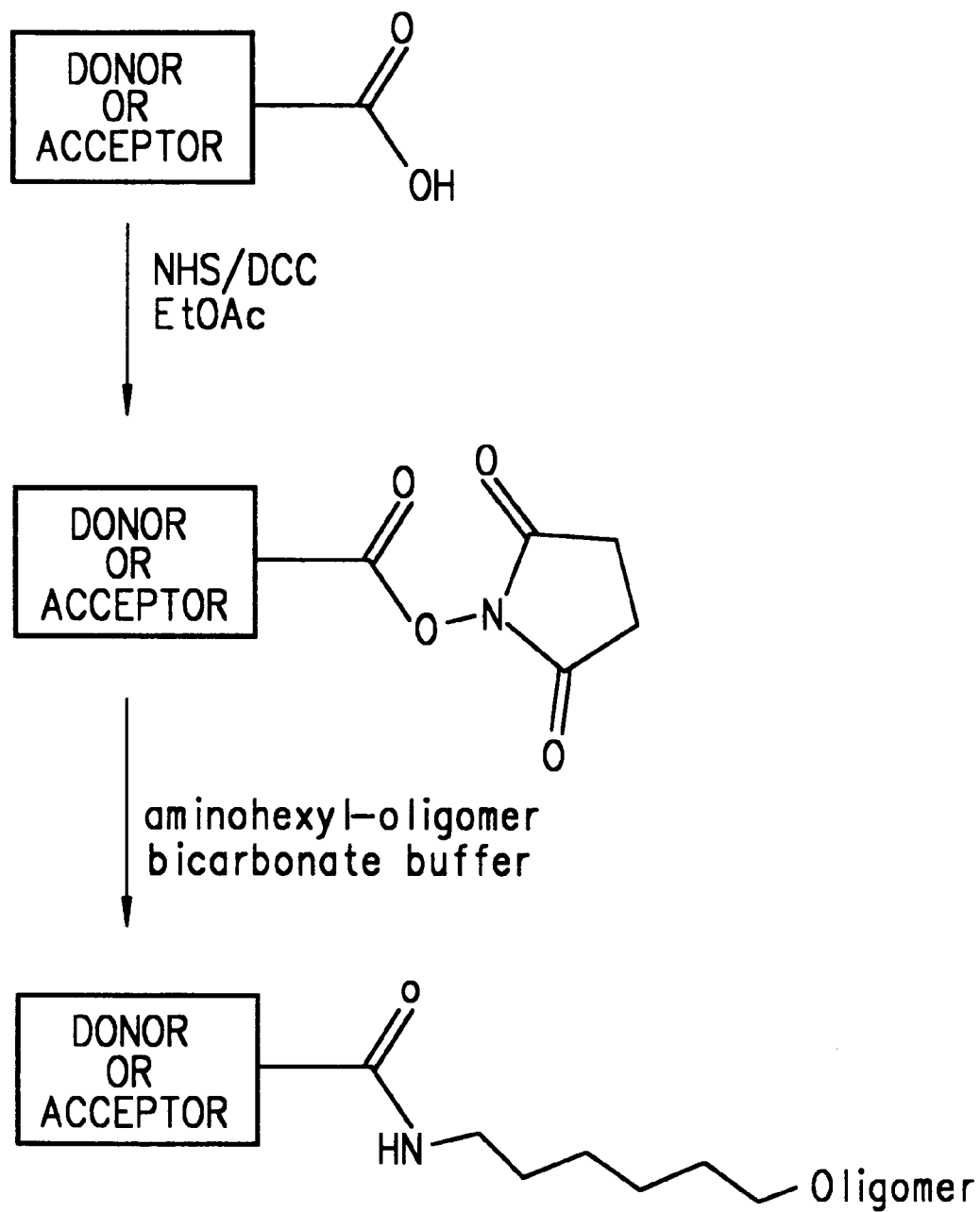
FIG. 1 illustrates the modification of a carboxy substituent on a energy transfer dye to an activated N-hydroxysuccinimidyl (NHS) ester which is then reacted with an aminohexyl-oligomer to form a dye labeled oligonucleotide primer.

I. Energy Transfer Dye Linkers Of The Present Invention

The present invention relates to novel linkers for linking a donor dye to an acceptor dye in an energy transfer fluorescent dye. The present invention also relates to energy transfer fluorescent dyes which incorporate these linkers. These linkers have been found to faciliate the efficient transfer of energy between a donor and acceptor dye in an energy transfer dye.

One linker according to the present invention for linking a donor dye to an acceptor dye in an energy transfer fluorescent dye has the general structure $R_{21}Z_1C(O)R_{22}R_{28}$, as illustrated below, where $R_2$, is a $C_{1-5}$ alkyl attached to the donor dye, C(O) is a carbonyl group, $Z_1$ is either NH, sulfur or oxygen, $R_{22}$ is a substituent which includes an alkene, diene, alkyne, a five and six membered ring having at least one unsaturated bond or a fused ring structure which is attached to the carbonyl carbon, and $R_{28}$ includes a functional group which attaches the linker to the acceptor dye.

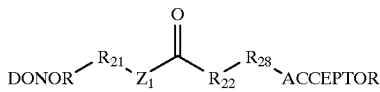

In one embodiment of this linker, illustrated below, the linker has the general structure $R_{21}Z_1C(O)R_{22}R_{29}Z_2C(O)$ where $R_2$, and $R_{22}$ are as detailed above, $Z_1$ and $Z_2$ are each independently either NH, sulfur or oxygen, $R_{29}$ is a $C_{1-5}$ alkyl, and the terminal carbonyl group is attached to the ring structure of the acceptor dye. In the variation where $Z_2$ is nitrogen, the $C(O)R_{22}R_{29}Z_2$ subunit forms an amino acid subunit.

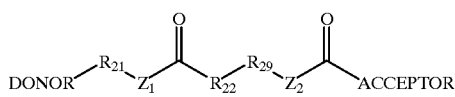

Particular examples of five or six membered rings which may be used as $R_{22}$ in the linker include, but are not limited to cyclopentene, cyclohexene, cyclopentadiene, cyclohexadiene, furan, thiofuran, pyrrole, isopyrole, isoazole, pyrazole, isoimidazole, pyran, pyrone, benzene, pyridine, pyridazine, pyrimidine, pyrazine and oxazine. Examples of fused ring structures include, but are not limited to indene, benzofuran, thionaphthene, indole and naphthalene.

A preferred embodiment of this linker is where $R_{21}$ and $R_{29}$ are methylene, $Z_1$ and $Z_2$ are NH, and $R_{22}$ is benzene, as shown below.

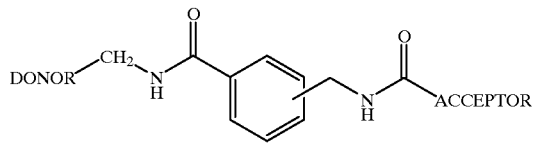

Table 3 illustrates examples of —$C(O)R_{22}$— subunits of linkers which may be used in the linkers of the present invention.

II. Energy Transfer Dyes Of The Present Invention

In general, the energy transfer dyes of the present invention include a donor dye which absorbs light at a first wavelength and emits excitation energy in response, an acceptor dye which is capable of absorbing the excitation energy emitted by the donor dye and fluorescing at a second wavelength in response, and a linker which attaches the donor dye to the acceptor dye. With regard to all of the molecular structures provided herein, it is intended that these molecular structures encompass not only the exact electronic structure presented, but also include all resonant structures and protonation states thereof.

One class of energy transfer fluorescent dyes according to the present invention includes a donor dye which is a member of the xanthene class of dyes, an acceptor dye and a linker which is a member of the group of linkers described in Section I. As used herein, xanthene dyes include all molecules having the general structure

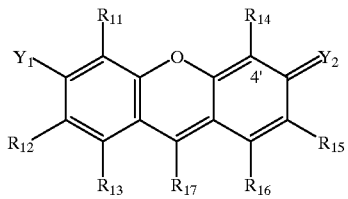

where $Y_1$ and $Y_2$ taken separately are either hydroxyl, oxygen, iminium or amine, the iminium and amine preferably being a tertiary iminium or amine. When $Y_1$ is hydroxyl and $Y_2$ is oxygen, and $R_{17}$ is a phenyl or substituted phenyl, the dye is a member of the fluorescein class of dyes. When $Y_1$ is amine and $Y_2$ is iminium, and $R_{17}$ is a phenyl or substituted phenyl, the dye is a member of the rhodamine class of dyes.

$R_{11}$–$R_{17}$ may be any substituent which is compatible with the energy transfer dyes of the present invention, it being noted that the $R_{11}$–$R_{17}$ may be widely varied in order to alter the spectral and mobility properties of the dyes. The number indicated in the ring structure indicates the 4' position on the xanthene ring structure. For the energy transfer dyes of the present invention in which the linker is attached to the 4' position of the xanthene ring structure, the $R_{14}$ substituent corresponds to the linker.

Examples of $R_{11}$–$R_{17}$ substituents include, but not limited to hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof.

In one embodiment, $R_{15}$ and $R_{16}$ are taken together to form a substituted or unsubstituted benzene ring. This class of xanthene dyes are referred to herein as asymmetric benzoxanthene dyes and are described in U.S. application Ser. No. 08/626,085, filed Apr. 1, 1996, entitled Asymmetric Benzoxanthene Dyes, by Scott C. Benson, et al. which is incorporated herein by reference.

In another embodiment, $R_{17}$ is a phenyl or substituted phenyl having the general formula

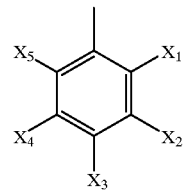

Substituents $X_1$–$X_5$ on the phenyl ring can include hydrogen, fluorine, chlorine, bromine, iodine, carboxyl, alkyl, alkene, alkyne, sulfonate, amino, ammonium, amido, nitrile, alkoxy, where adjacent substituents are taken together to form a ring, and combinations thereof.

In one embodiment, the donor dye is a member of the class of dyes where $Y_1$ is amine, $Y_2$ is iminium, and $X_2$ and $X_5$ are chlorine, referred to herein as 4,7-dichlororhodamine dyes. Dyes falling within the 4,7-dichlororhodamine class of dyes and their synthesis are described herein as well as in U.S. application Ser. No.: 08/672,196; filed: Jun. 27, 1996; entitled: "4,7-DICHLORORHODAMINE DYE" which is incorporated herein by reference.

As used here, alkyl denotes straight-chain and branched hydrocarbon moieties, i.e., methyl, ethyl, propyl, isopropyl, tert-butyl, isobutyl, sec-butyl, neopentyl, tert-pentyl, and the like. Substituted alkyl denotes an alkyl moiety substituted with any one of a variety of substituents, including, but not limited to hydroxy, amino, thio, cyano, nitro, sulfo, and the like. Haloalkyl denotes a substituted alkyl with one or more halogen atom substituents, usually fluoro, chloro, bromo, or iodo. Alkene denotes a hydocarbon wherein one or more of the carbon-carbon bonds are double bonds, and the non-double bonded carbons are alkyl or substituted alkyl. Alkyne denotes a hydocarbon where one or more of the carbons are bonded with a triple bond and where the non-triple bonded carbons are alkyl or substituted alkyl moieties. Sulfonate refers to moieties including a sulfur atom bonded to 3 oxygen atoms, including mono- and di-salts thereof, e.g., sodium sulfonate, potassium sulfonate, disodium sulfonate, and the like. Amino refers to moieties including a nitrogen atom bonded to 2 hydrogen atoms, alkyl moieties, or any combination thereof. Amido refers to moieties including a carbon atom double bonded to an oxygen atom and single bonded to an amino moiety. Nitrile refers to moieties including a carbon atom triple bonded to a nitrogen atom. Alkoxy refers to a moiety including an alkyl moiety single bonded to an oxygen atom. Aryl refers to single or multiple phenyl or substituted phenyl, e.g., benzene, naphthalene, anthracene, biphenyl, and the like.

$R_{11}$–$R_{17}$ may also each independently be a linking moiety which may be used to attach the energy transfer dye to a reagent, such as a nucleotide, nucleoside or oligonucleotide. Examples of linking moieties include isothiocyanate, sulfonyl chloride, 4,6-dichlorotriazinylamine, succinimidyl ester, or other active carboxylate whenever the complementary functionality is amine. Preferably the linking group is maleimide, halo acetyl, or iodoacetamide whenever the complementary functionality is sulfhydryl. See R. Haugland, *Molecular Probes Handbook of Fluorescent Probes and Research Chemicals,* Molecular probes, Inc. (1992). In a particularly preferred embodiment, as illustrated in FIG. 1, the linking group is an activated NHS ester formed from a carboxyl group on either the donor or acceptor dye which can be reacted with an aminohexyloligomer to form a dye labeled oligonucleotide primer.

The energy transfer fluorescent dyes of this embodiment also include an acceptor dye which is capable of absorbing the excitation energy emitted by the donor dye and fluorescing at a second wavelength in response, and a linker which attaches the donor dye to the acceptor dye. In the first class of energy transfer dyes, the linker is a member of the class of linkers described in Section I and is attached to the donor dye at the 4' position of the xanthene ring structure.

Energy transfer dyes of this first class exhibit enhanced fluorescent strength as compared to the acceptor fluorophore itself and energy transfer fluorescent dyes having the same donor—acceptor pair where the linkage between the donor—acceptor pair is different.

The present invention also relates to a second class of energy transfer fluorescent dyes in which the donor and acceptor dyes each have the general structure

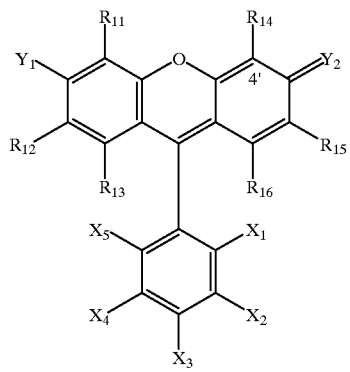

where $Y_1$, $Y_2$, $R_{11}$–$R_{16}$ and $X_1$–$X_5$ are as specified above.

Within this class of dyes, the linker is attached to the donor and acceptor dyes by one of $X_3$ and $X_4$ substituents of each of the donor and acceptor dyes.

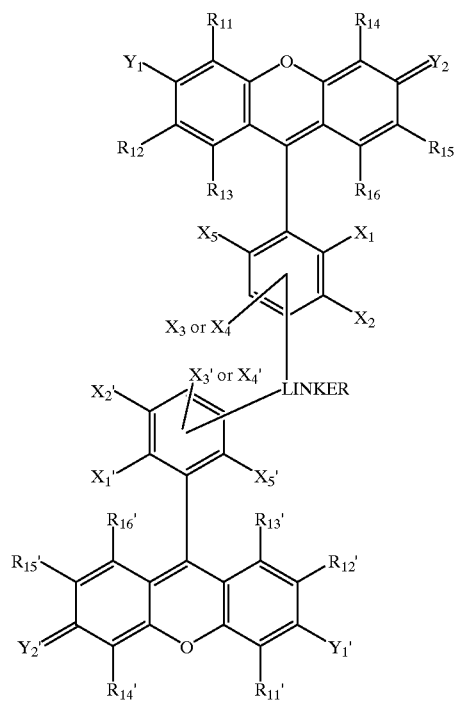

In a preferred embodiment of this class of dyes, the linker is attached to the donor and acceptor dyes by the $X_3$ substituent of each of the donor and acceptor dyes.

Within this class of dyes, the linker is preferably short and/or rigid as this has been found to enhance the transfer of energy between the donor and acceptor dyes.

The present invention also relates to a third class of energy transfer fluorescent dyes in which the acceptor dye is a member of the 4,7-dichlororhodamine class of dyes, i.e., dyes having the general structure

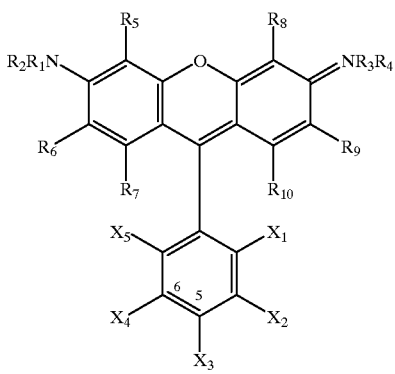

where

R₁–R₄ are each independently hydrogen, alkyl or where R₁ and R₅, R₂ and R₆, R₃ and R₈, R₄ and R₉ are taken together to form a ring, and combinations thereof;

R₅–R₁₀ are each independently hydrogen, fluorine, chlorine, bromine, iodine, carboxyl, alkyl, alkene, alkyne, sulfonate, sulfone, amino, ammonium, amido, nitrile, alkoxy, phenyl, or substituted phenyl, or where adjacent substituents are taken together to form a ring, and combinations thereof;

X₁, X₃ and X₄ are each independently hydrogen, fluorine, chlorine, bromine, iodine, carboxyl, alkyl, alkene, alkyne, sulfonate, sulfone, amino, ammonium, amido, nitrile, or alkoxy, or where adjacent substituents are taken together to form a ring, and combinations thereof; and X₂ and X₅ are chlorine.

With regard to R₁–R₁₀, X₃ and X₄, R₁ and R₅, R₂ and R₆, R₃ and R₈, R₄ and R₉, and X₃ and X₄ may each independently be taken together to form a 5, 6, or 7 membered ring.

The numbers (4', 5, 6) indicated in the ring structure indicate the 4', 5 and 6 ring positions on the rhodamine ring structure. As will be discussed herein, the 4' and 5 ring positions are preferred sites for attachment of the linker used in the energy transfer dyes of the present invention which attaches the donor to the acceptor fluorophore. The 4', 5 and 6 ring positions are also preferred sites for attachment of a biomolecule, such as a nucleotide or oligonucleotide to the energy transfer dye.

Donor dyes within this class of energy transfer dyes may include any dye which emits excitation energy which a 4,7-dichlororhodamine dye is capable of absorbing and producing an energy emission in response. In one embodiment, the donor dye has a xanthene ring structure with a 4' ring position where the 4,7-dichlororhodamine acceptor dye is attached to the donor dye by a linker which is attached to the 4' ring position of the xanthene dye. The linker is preferably attached to the 5 or 6 ring positions of the 4,7-dichlororhodamine acceptor dye.

Energy transfer dyes according to this third class of dyes, i.e., where 4,7-dichlororhodamine is the acceptor dye, provide the advantage of having a relatively narrow emission spectrum as compared to other rhodamine dyes. This narrow emission spectrum enhances the spectral resolution achievable by a set of these dyes, thereby facilitating multicomponent analysis using these dyes.

The present invention also relates to a fourth class of energy transfer fluorescent dyes in which the donor dye is a member of the xanthene class of dyes, the acceptor dye is a member of the xanthene, cyanine, phthalocyanine and squaraine classes of dyes, and the acceptor has an emission maximum that is greater than about 600 nm and/or preferably has an emission maximum that is at least about 100 nm greater than the absorbance maximum of the donor dye. Within this class of dyes, the donor is preferably a member of the fluorescein class of dyes.

The fourth class of energy transfer dyes of the present invention exhibit unusually large Stoke shifts, as measured by the difference between the absorbance of the donor and the emission of the acceptor. In addition, these dyes exhibit efficient energy transfer in that minimal donor fluorescence is observed.

Described herein in greater detail are the four classes of energy transfer dyes of the present invention.

TABLE 1

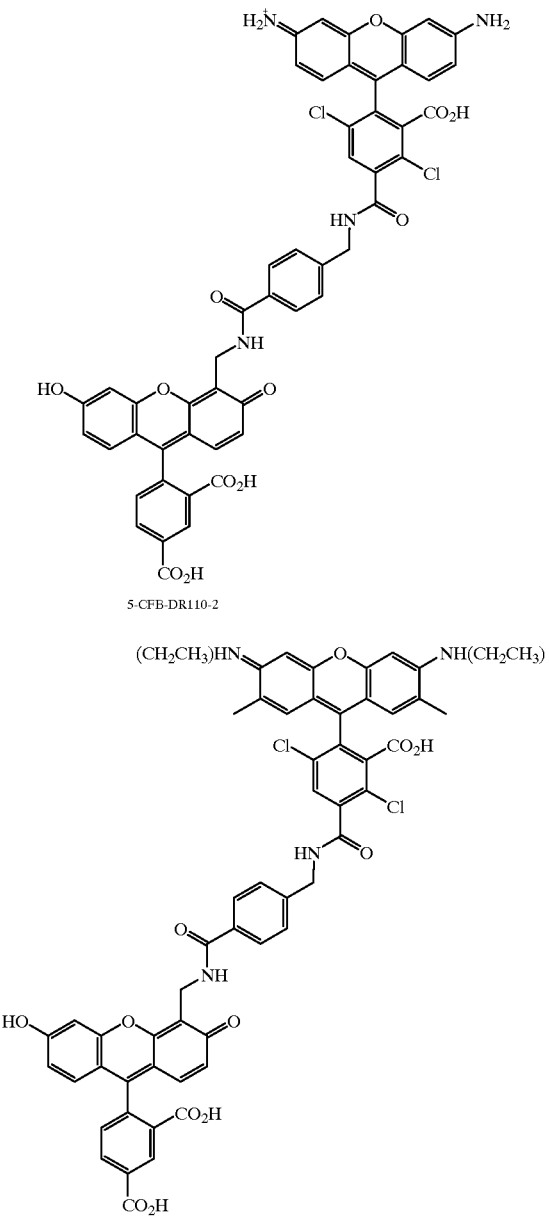

TABLE 1-continued
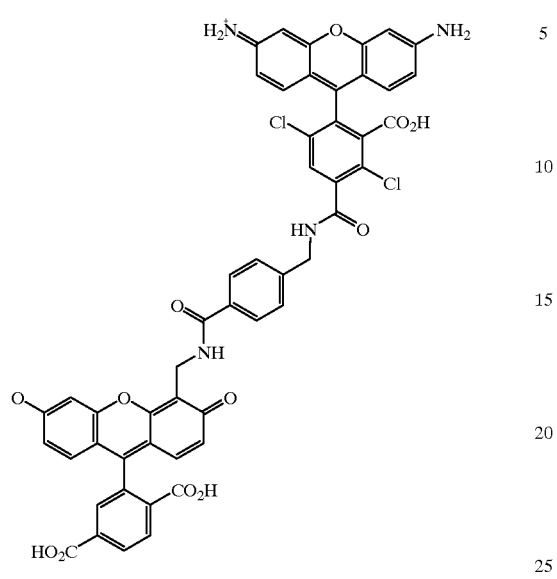
6-CFB-DR110-2
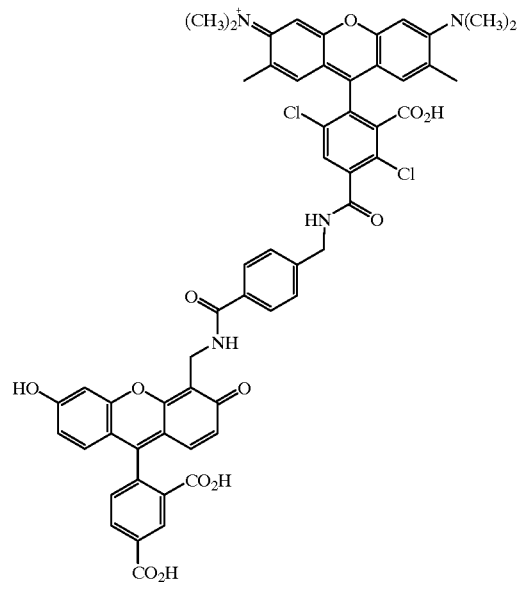
5-CFB-DTMR-2
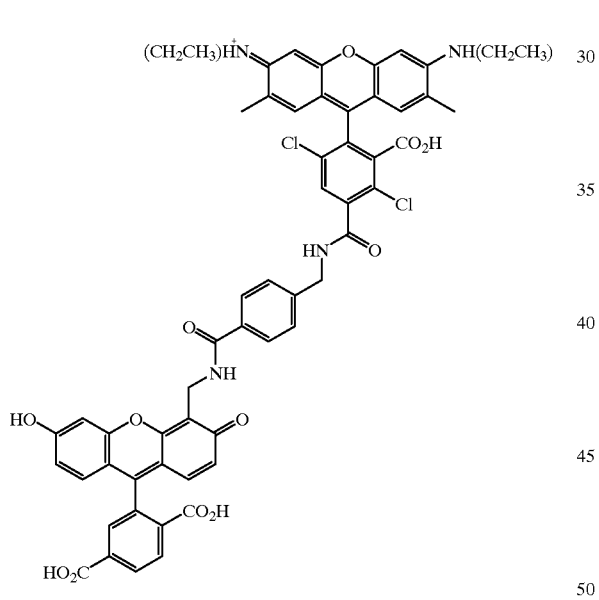
6-CFB-DR6G-2
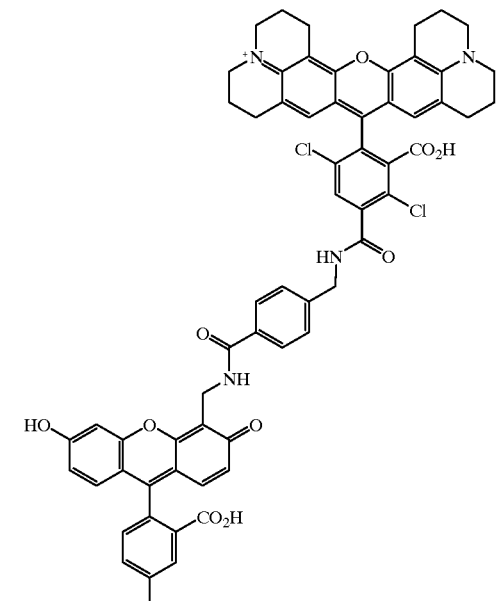
5-CFB-DROX-2

TABLE 1-continued
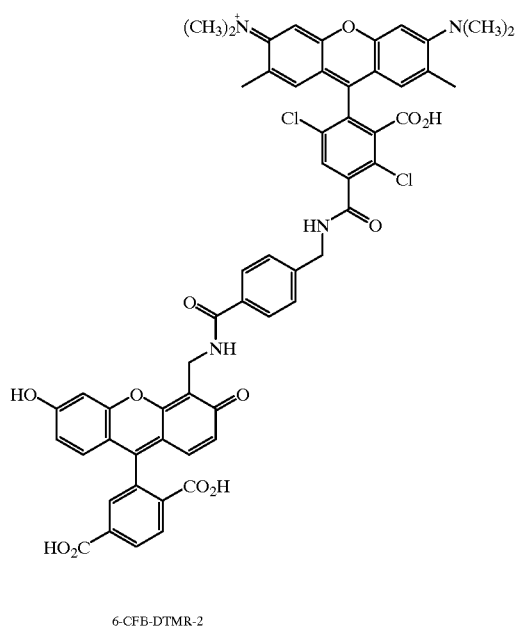
6-CFB-DTMR-2
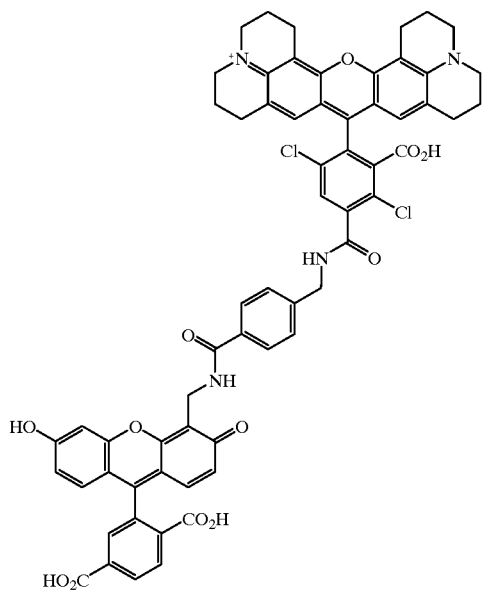
6-CFB-DROX-2
TABLE 1A
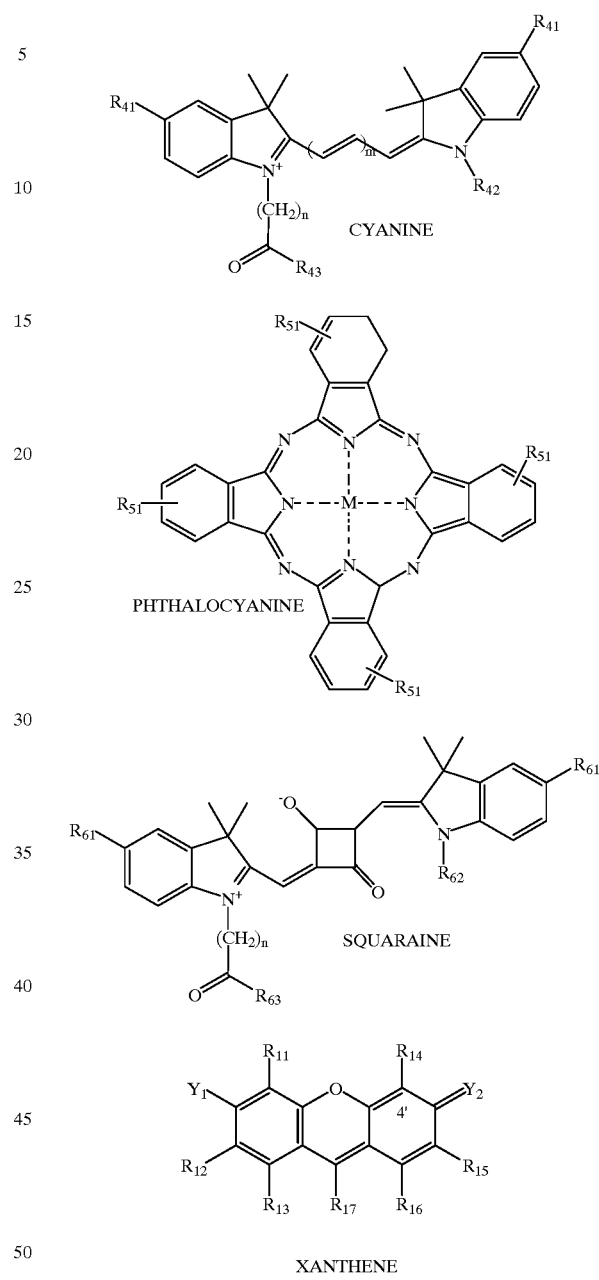
A. First Class Of Energy Transfer Dyes
As described above, the first class of energy transfer dyes according to the present invention includes a donor dye which is a member of the xanthene class of dyes and hence has a xanthene ring structure with a 4' ring position. Within this class of dyes, the acceptor dye is a dye which is capable of absorbing the excitation energy emitted by the donor dye and fluorescing at a second wavelength in response.

According to this embodiment, the donor may be a member of the fluorescein, rhodamine or asymmetric benzoxanthene classes of dyes, these dyes each being members of the broader xanthene class of dyes. Illustrated below are the general structural formulas for these xanthene dyes. The substituents illustrated on these dyes may be selected from the wide variety of substituents which may be incorporated onto these different classes of dyes since all dyes having the general xanthene, fluorescein, rhodamine, and asymmetric benzoxanthene ring structures are intended to fall within the scope of this invention.

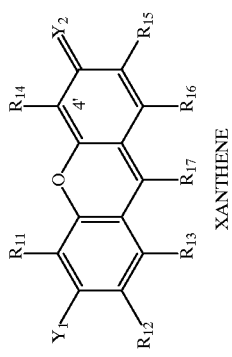
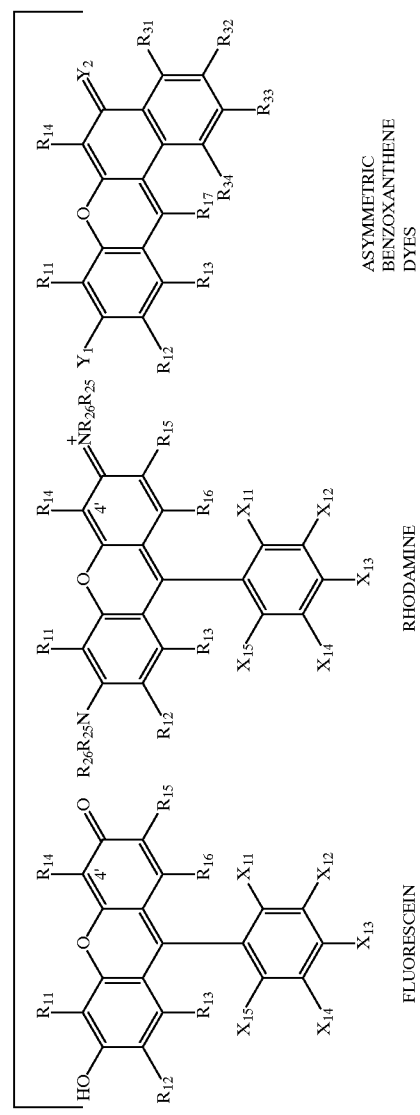

Examples of classes of acceptor dyes which may be used in the energy transfer fluorescent dye of this embodiment include, but are not limited to, xanthene dyes, cyanine dyes, phthalocyanine dyes and squaraine dyes. The general structures of these dyes are illustrated in Table 1A. The substituents illustrated on these dyes may be selected from the wide variety of substituents which may be incorporated onto these different classes of dyes since all dyes having the general xanthene, fluorescein, rhodamine, asymmetric benzoxanthene, cyanine, phthalocyanine and squaraine ring structures are intended to fall within the scope of this invention.

Examples of donor dyes which may be used in this embodiment include, but are not limited to fluorescein, isomers of carboxyfluorescein (e.g., 5 and 6 carboxy), isomers of carboxy-HEX (e.g., 5 and 6 carboxy), NAN, CL-FLAN, TET, JOE, ZOE, rhodamine, isomers of carboxyrhodamine (e.g., 5 and 6 carboxy), isomers of carboxy $R_{110}$ (e.g., 5 and 6 carboxy), isomers of carboxy R6G (e.g., 5 and 6 carboxy), 4,7-dichlorofluoresceins (See U.S. Pat. No. 5,188,934), 4,7-dichlororhodamines (See application Ser. No. 08/672,196, filed Jun. 27, 1996), asymmetric benzoxanthene dyes (See U.S. application Ser. No. 08/626,085, filed Apr. 1, 1996), and isomers of N,N,N',N'-tetramethyl-carboxyrhodamine (TAMRA) (e.g., 5 and 6 carboxy).

Examples of acceptor dyes which may be used in this embodiment include, but are not limited to isomers of carboxyfluorescein (e.g., 5 and 6 carboxy), 4,7-dichlorofluoresceins, 4,7-dichlororhodamines, fluoresceins, asymmetric benzoxanthene dyes, isomers of carboxy-HEX (e.g., 5 and 6 carboxy), NAN, Cl-FLAN, TET, JOE, ZOE, rhodamine, isomers of carboxyrhodamine (e.g., 5 and 6 carboxy), isomers of carboxy R110 (e.g., 5 and 6 carboxy), isomers of carboxy R6G (e.g., 5 and 6 carboxy), isomers of N,N,N',N'-tetramethyl carboxyrhodamine (TAMRA) (e.g., 5 and 6 carboxy), isomers of carboxy-X-rhodamine (ROX) (e.g., 5 and 6 carboxy) and Cy5. Illustrated in Table 2 are the structures of these dyes.

In the first class of energy transfer dyes according to the present invention, the linker is attached to the donor dye at the 4' position of the xanthene ring structure. In one embodiment, the linker has the general structure $R_{21}Z_1C(O)R_{22}R_{28}$, as illustrated below, where $R_{21}$ is a $C_{1-5}$ alkyl which is attached to the 4' ring position of the donor xanthene dye, $Z_1$ is either NH, sulfur or oxygen, C(O) is a carbonyl group, $R_{22}$ is a substituent which includes an alkene, diene, alkyne, a five and six membered ring having at least one unsaturated bond or a fused ring structure which is attached to the carbonyl carbon, and $R_{28}$ is a functional group which attaches the linker to the acceptor dye.

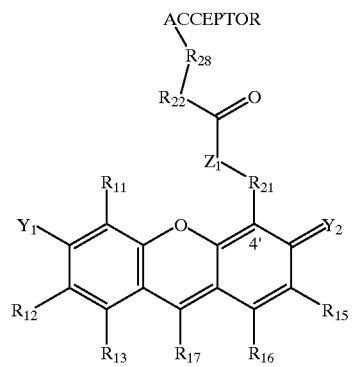

Examples of five or six membered rings which may be used in $R_{22}$ include, but are not limited to cyclopentene, cyclohexene, cyclopentadiene, cyclohexadiene, furan, thiofuran, pyrrole, isopyrole, isoazole, pyrazole, isoimidazole, pyran, pyrone, benzene, pyridine, pyridazine, pyrimidine, pyrazine and oxazine. Examples of fused ring structures include, but are not limited to indene, benzofuran, thionaphthene, indole and naphthalene.

In one variation of this embodiment, illustrated below, the linker has the general structure $R_{21}Z_1C(O)R_{22}R_{29}Z_2C(O)$ where $R_{21}$ is a $C_{1-5}$ alkyl which is attached to the 4' ring position of the donor xanthene dye, $Z_1$ and $Z_2$ are each independently either NH, sulfur or oxygen, C(O) is a carbonyl group, $R_{22}$ is a substituent which includes an alkene, diene, alkyne, a five and six membered ring having at least one unsaturated bond or a fused ring structure which is attached to the carbonyl carbon, $R_{29}$ is a $C_{1-5}$ alkyl, and the terminal carbonyl group is attached to the ring structure of the acceptor dye.

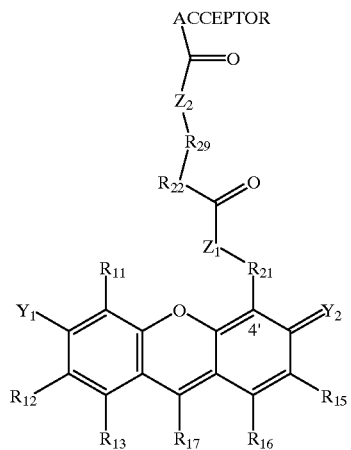

A preferred embodiment of this linker is where $R_2$, and $R_{29}$ are methylene, $Z_1$ and $Z_2$ are NH, and $R_{22}$ is benzene, as shown below.

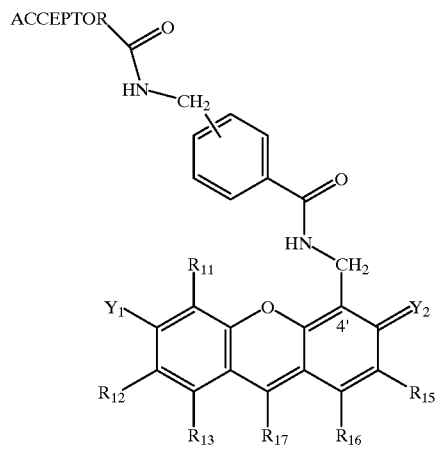

TABLE 2
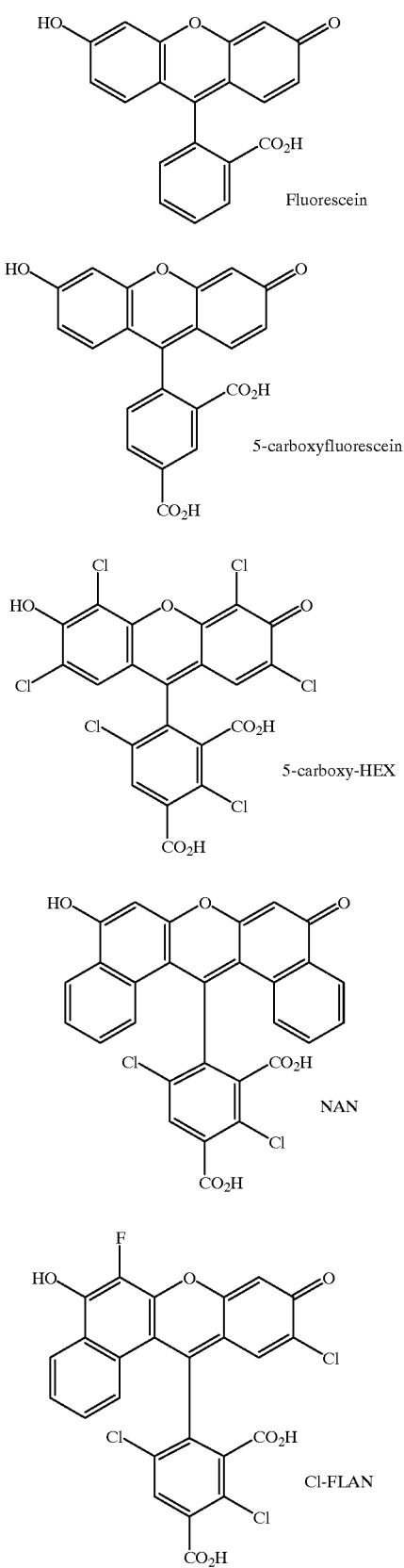
TABLE 2-continued
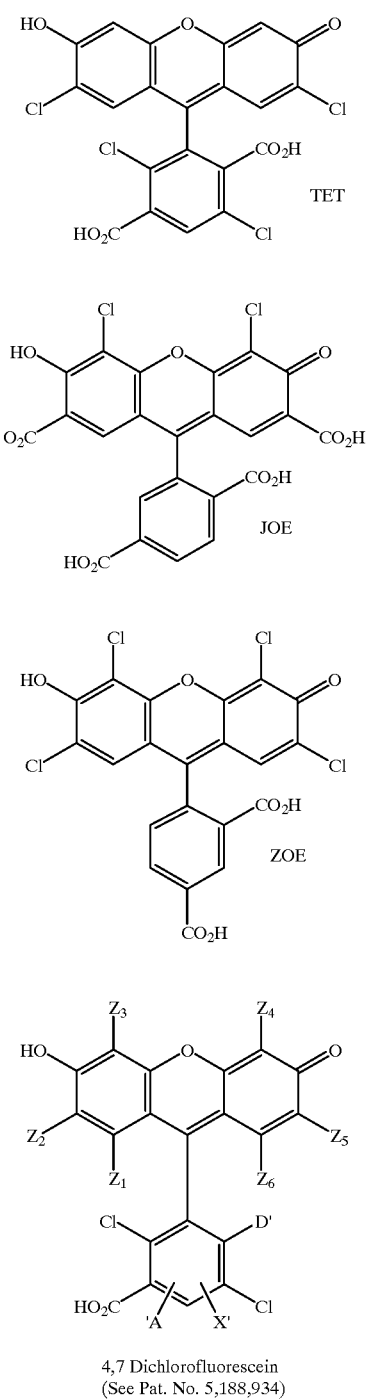
4,7 Dichlorofluorescein
(See Pat. No. 5,188,934)

TABLE 2-continued
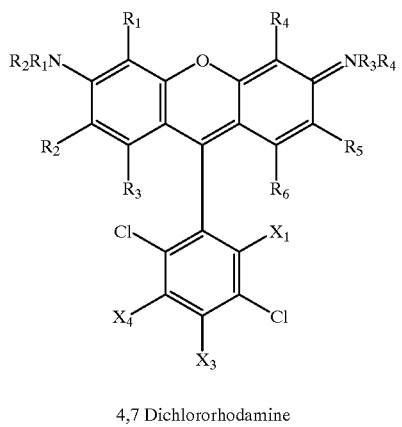
4,7 Dichlororhodamine
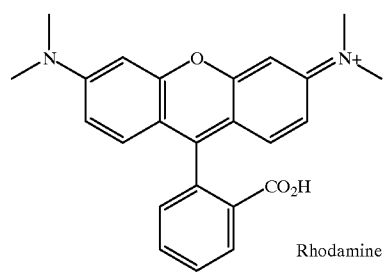
Rhodamine
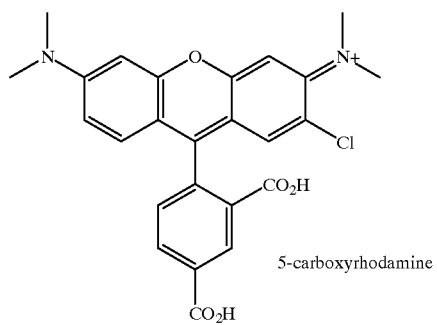
5-carboxyrhodamine
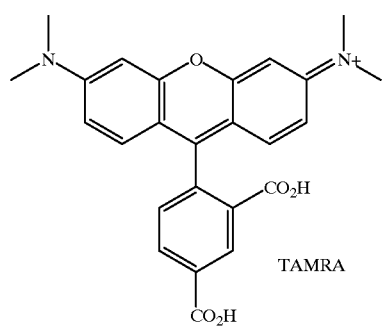
TAMRA
TABLE 2-continued
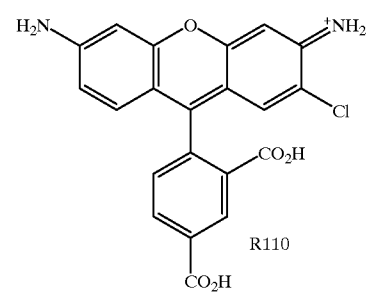
R110
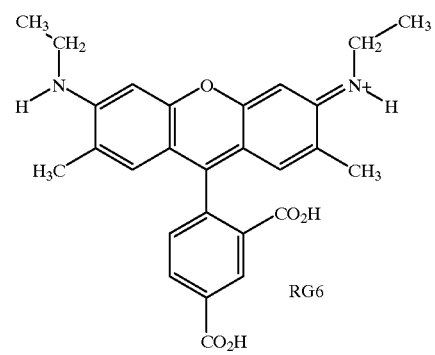
RG6
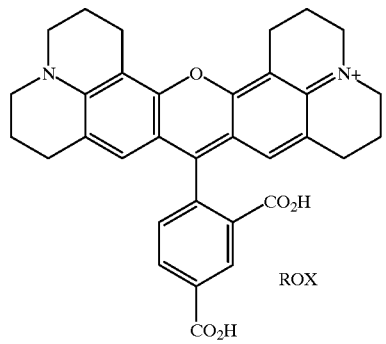
ROX
TABLE 3
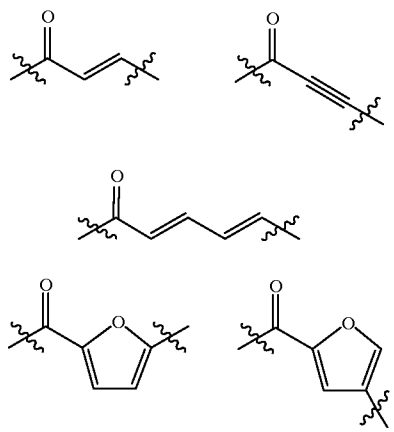

TABLE 3-continued

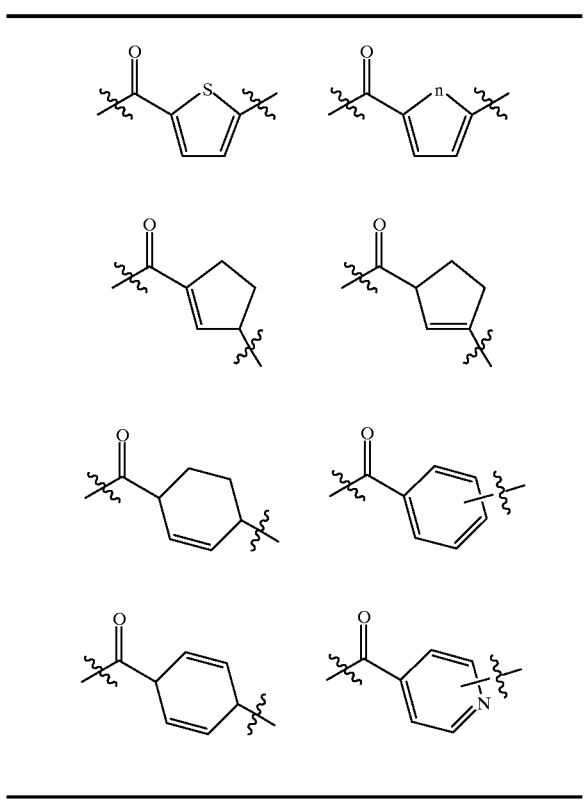

Figure 2:
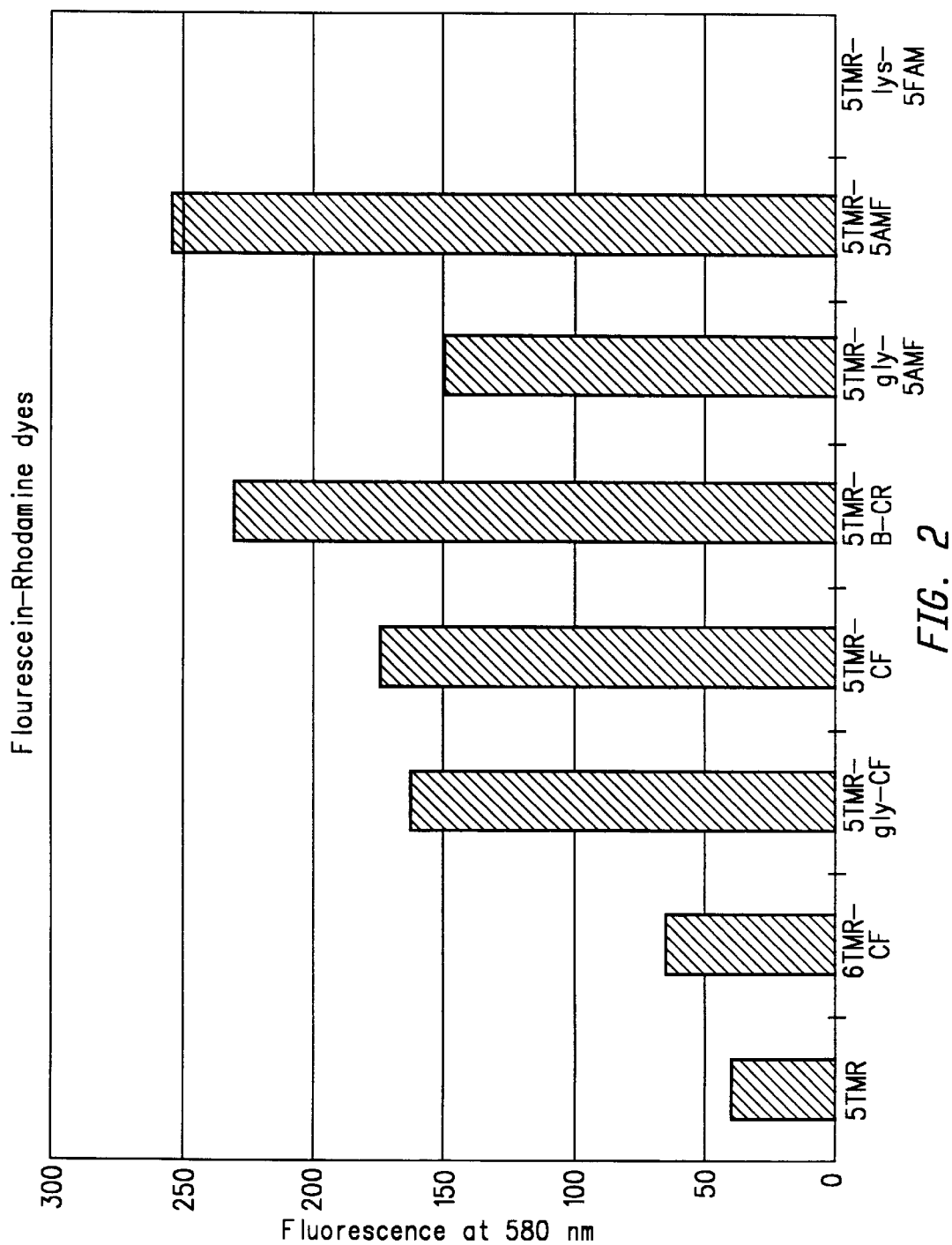
FIG. 2 compares the fluorescence emission strength of a series of energy transfer dyes of the present invention to other energy transfer dyes and the acceptor dye alone.

As illustrated in Example 4 and FIG. 2, energy transfer dyes such as 5-TMR-B-CF, which include a donor, acceptor and linker as specified above exhibit enhanced fluorescence as compared to the acceptor itself and energy transfer fluorescent dyes having the same donor—acceptor pair where the linker between the donor—acceptor pair is different. Without being bound by theory, the enhanced fluorescence intensity observed is believed to be due to an improved energy transfer orientation between the donor and acceptor dye which is achieved and maintained by the relatively rigid $R_{22}$ portion of the linker. As a result, the energy transfer fluorescent dyes of the present invention exhibit enhanced fluorescent strength as compared to the acceptor fluorophore itself and energy transfer fluorescent dyes having the same donor acceptor pair where the linkage between the donor—acceptor pair is different. The enhanced fluorescent strength of these dyes is particularly evident in the presence of 8 M urea which serves to reduce dye stacking.

In one variation of this embodiment, the acceptor is a member of the xanthene class of dyes having the general structure

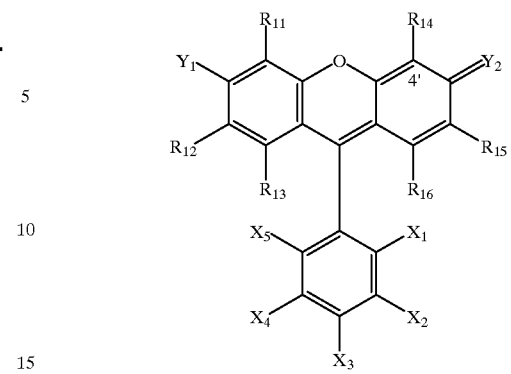

where $Y_1$, $Y_2$, $R_{11}$–$R_{16}$ and $X_1$–$X_5$ are as specified above.

According to this variation, it is preferred that a linker, such as the ones described above, is attached to the acceptor xanthene dye via the $X_3$ or $X_4$ substituent of the acceptor xanthene dye. In a preferred embodiment, as illustrated below, the linker is attached to the $X_3$ substituent of the acceptor xanthene dye.

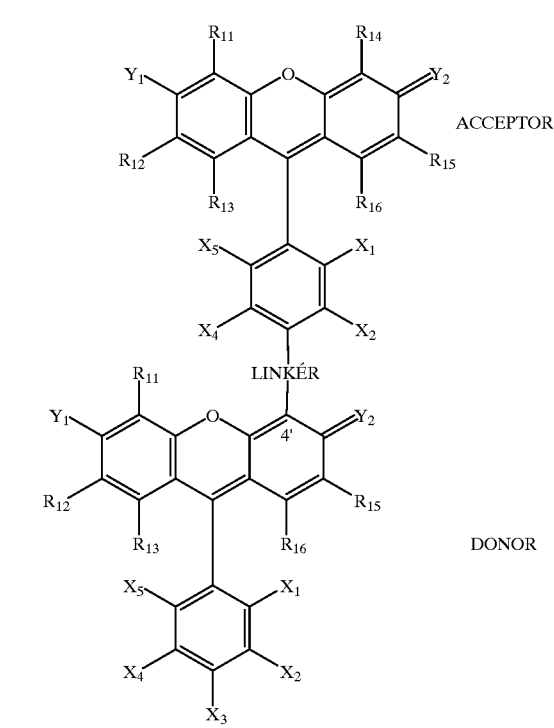

Table 4 provides examples of the above-described energy transfer dyes according to this embodiment of the invention. It is noted that although the dyes illustrated in Table 4 include a 5-carboxyfluorescein donor dye and a TAMRA acceptor dye, it should be understood that a wide variety of other xanthene dyes can be readily substituted as the donor dye. It should also be understood that a wide variety of other xanthene dyes, as well as cyanine, phthalocyanine and squaraine dyes can be readily substituted for the TAMRA acceptor dye, as has been described above, all of these variations with regard to the donor and acceptor dyes falling within the scope of the invention.

TABLE 4

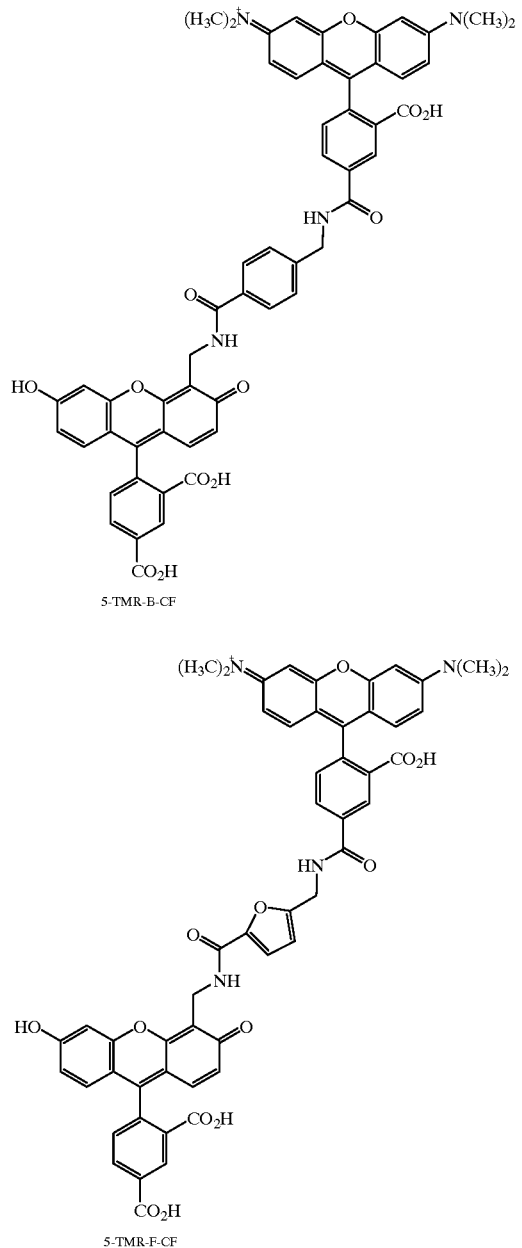

TABLE 4-continued

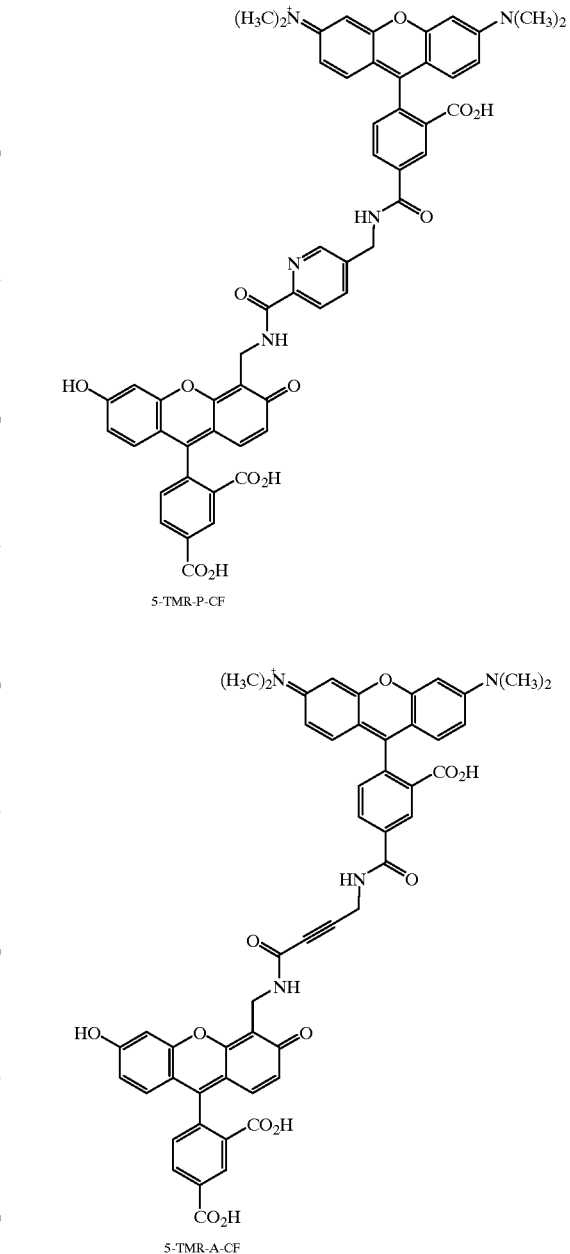

TABLE 4-continued
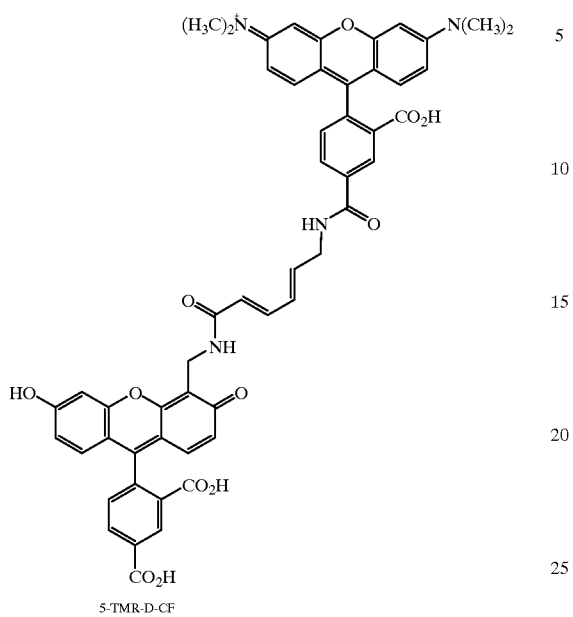
5-TMR-D-CF
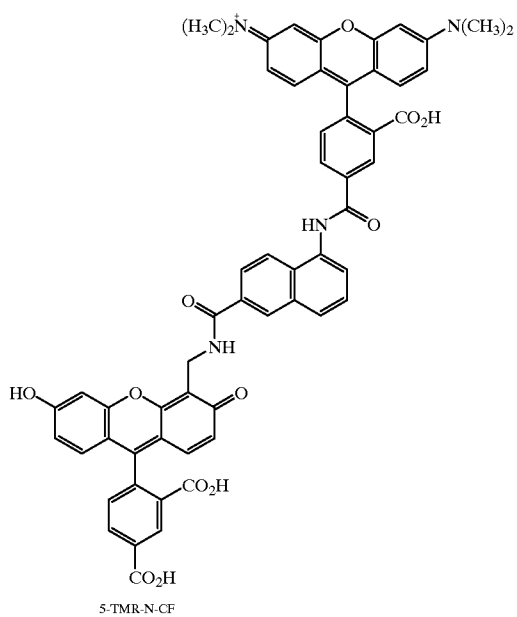
5-TMR-N-CF
TABLE 4-continued
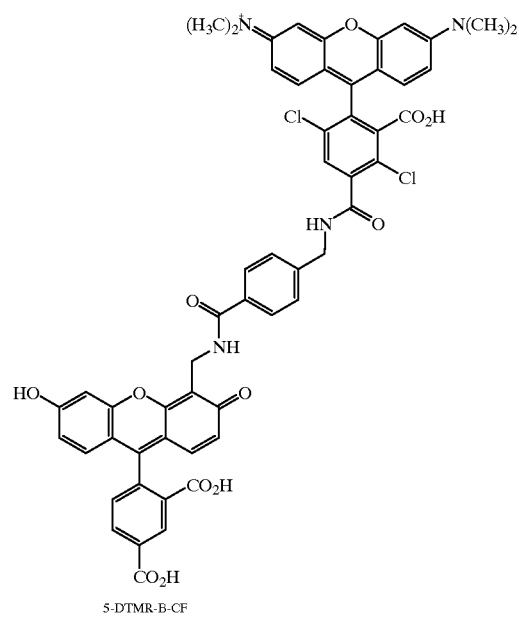
5-DTMR-B-CF
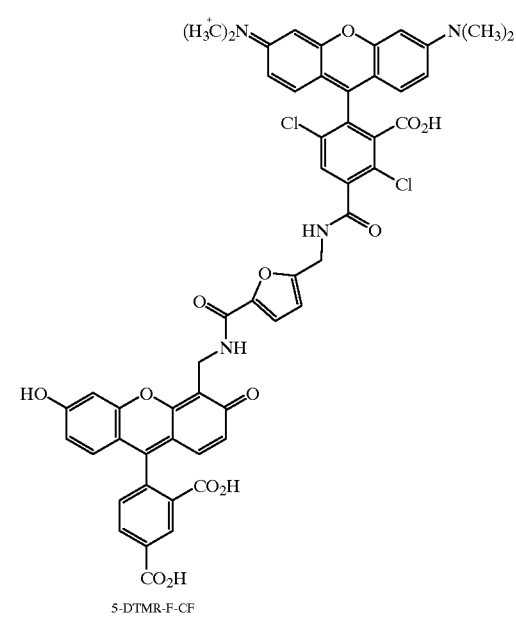
5-DTMR-F-CF TABLE 4-continued
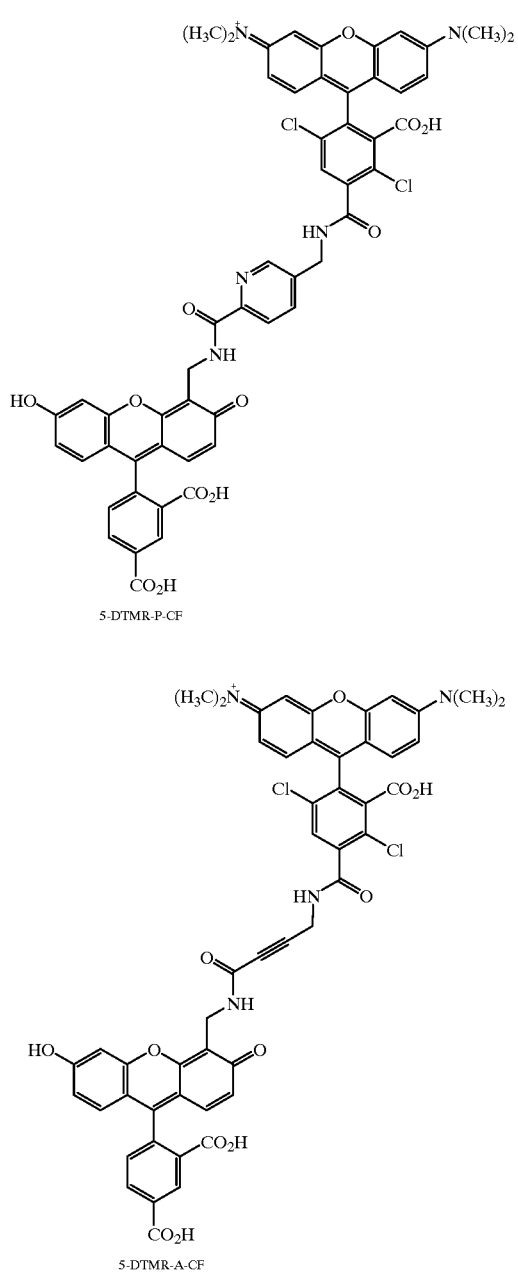
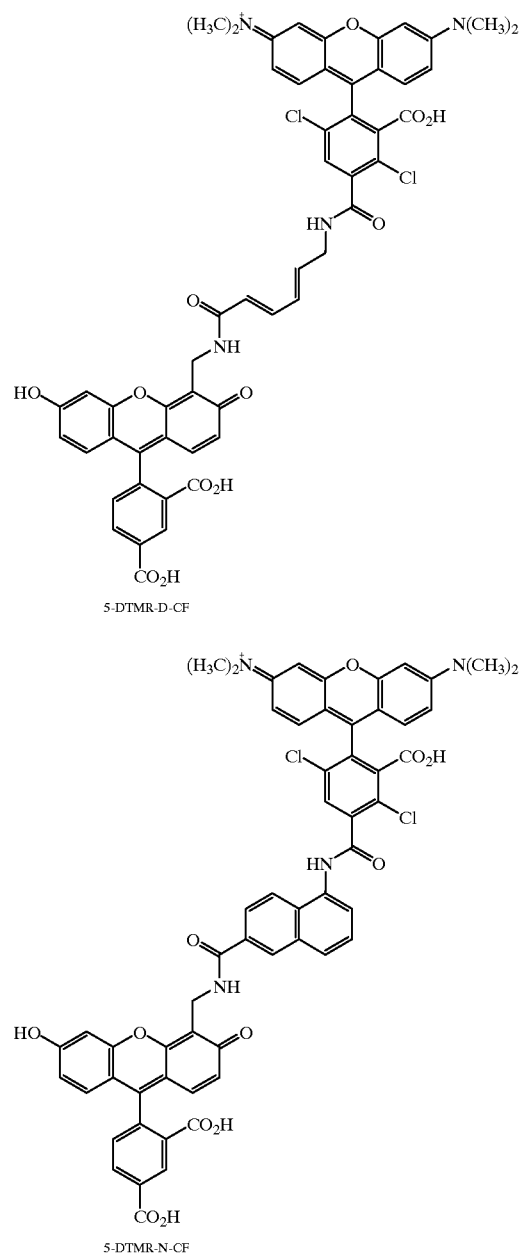
B. Second Class Of Energy Transfer Dyes
The present invention also relates to a second class of energy transfer fluorescent dyes, illustrated below, in which the donor dye and acceptor each are members of the xanthene class of dyes having the general structure

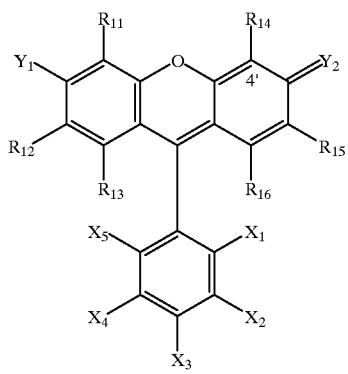

where $Y_1$, $Y_2$, $R_{11}$–$R_{16}$ and $X_1$–$X_5$ are as specified above.

According to this embodiment, the linker is attached to the $X_3$ or $X_4$ substituent of both the donor and acceptor dyes, as illustrated below.

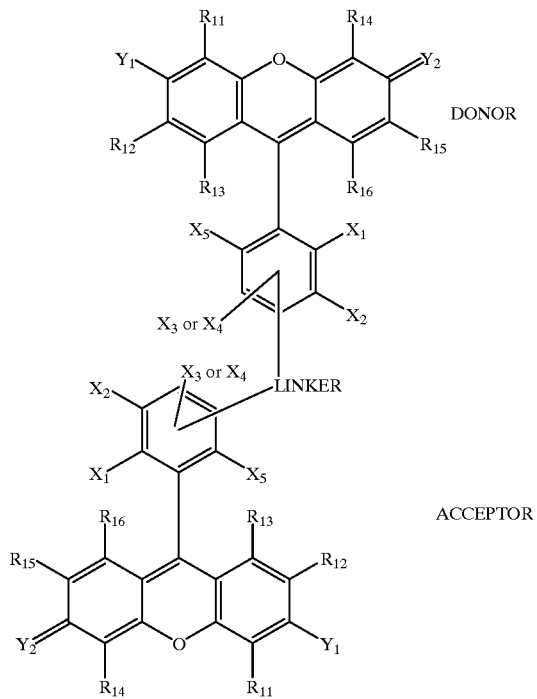

In this embodiment, the linker is preferably short and/or rigid as this has been found to enhance the transfer of energy between the donor and acceptor dyes. For example, in one variation of this embodiment, the linker preferably has a backbone attaching the donor to the acceptor which is less than 9 atoms in length. In another variation of this embodiment, the linker includes a functional group which gives the linker some degree of structural rigidity, such as an alkene, diene, an alkyne, a five and six membered ring having at least one unsaturated bond or a fused ring structure. In yet another variation, the linker has the general formula $R_{25}Z_3C(O)$ or $R_{25}Z_3C(O)R_{26}Z_4C(O)$ where $R_{25}$ is attached to the donor dye, $C(O)$ is a carbonyl group and the terminal carbonyl group is attached to the acceptor dye, $R_{25}$ and $R_{26}$ are each selected from the group of $C_{1-4}$ alkyl, and $Z_3$ and $Z_4$ are each independently either NH, O or S.

Examples of donor and acceptor dyes which may be used in this embodiment include, but are not limited to fluorescein, 5 or 6 carboxyfluorescein, 5 or 6 carboxy-HEX, NAN, Cl-FLAN, TET, JOE, ZOE, 4,7-dichlorofluoresceins, asymmetric benzoxanthene dyes, rhodamine, 5 or 6 carboxyrhodamine, 5 or 6 carboxy-R110, 5 or 6 carboxy-R6G, N,N,N',N'-tetramethyl (5 or 6)-carboxyrhodamine (TAMRA), 5 or 6 carboxy-X-rhodamine (ROX) and 4,7-dichlororhodamines. Illustrated in Table 2 are the structures of these dyes.

In another variation of this embodiment, the linker includes a $R_{27}Z_5C(O)$ group where $R_{27}$ is a $C_{1-5}$ alkyl attached to the donor dye, $Z_5$ is either NH, sulfur or oxygen, and $C(O)$ is a carbonyl group attached to the acceptor dye.

Table 5 provides examples of the second class of energy transfer dyes according to the present invention. It is noted that although the dyes illustrated in Table 5 include a 5-aminomethylfluorescein donor dye, it should be understood that a wide variety of other xanthene dyes can be readily substituted as the donor dye. It should also be understood that a wide variety of other xanthene dyes, as well as cyanine, phthalocyanine and squaraine dyes can be readily substituted for the TAMRA acceptor dye, as has been described above, all of these variations with regard to the donor and acceptor dyes falling within the scope of the invention.

TABLE 5

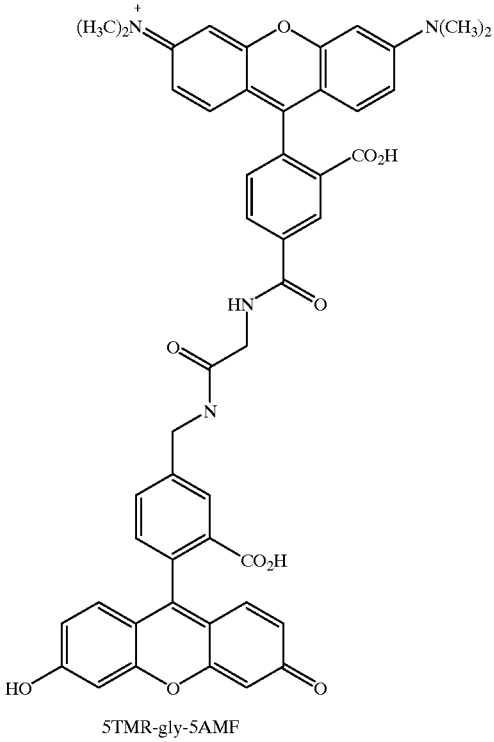

5TMR-gly-5AMF

TABLE 5-continued
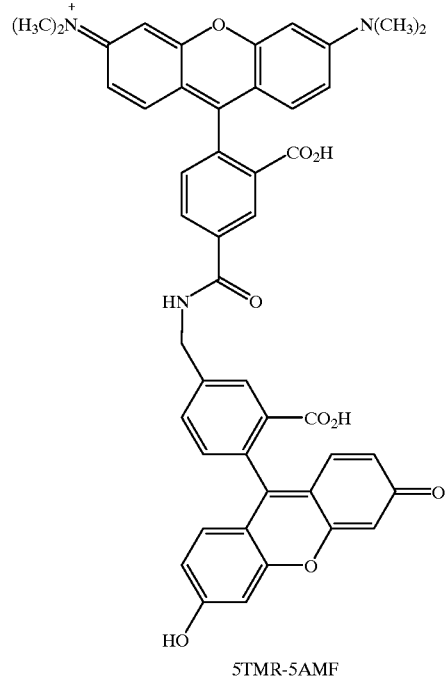
5TMR-5AMF
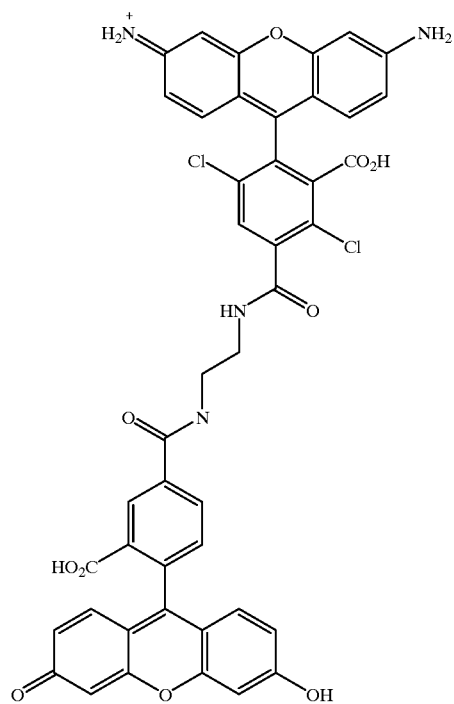
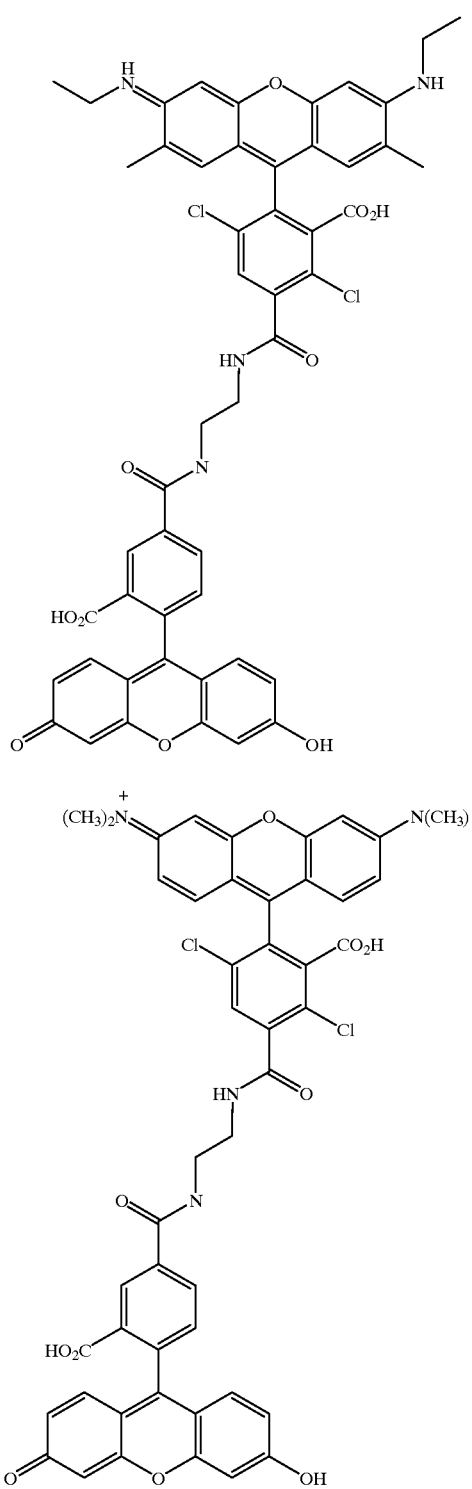

TABLE 5-continued
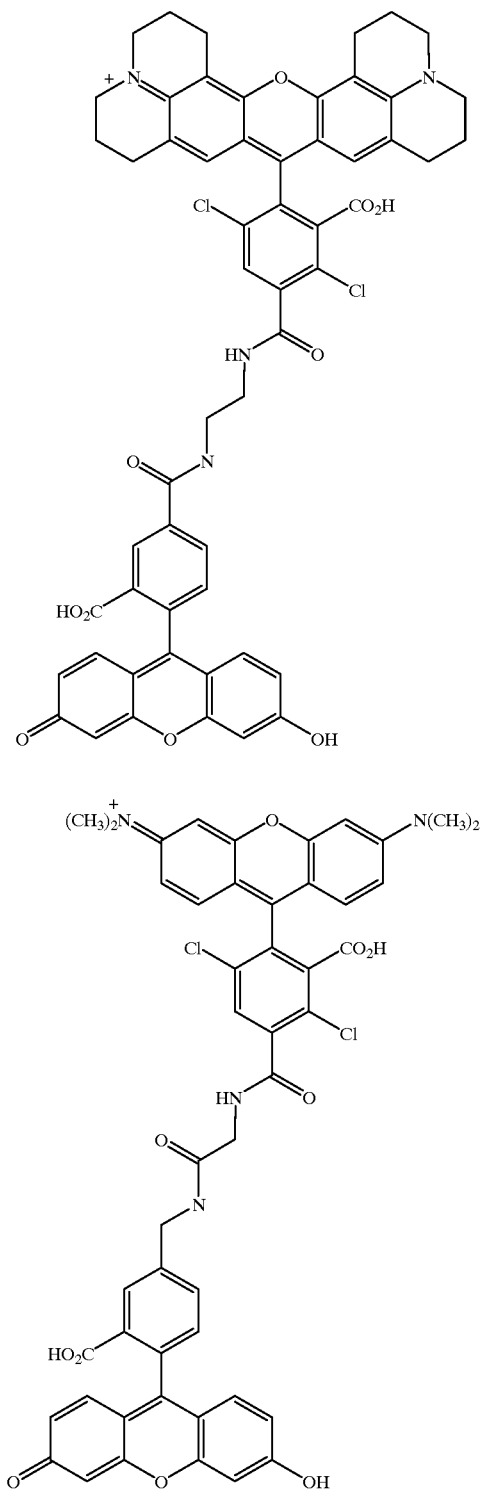
TABLE 5-continued
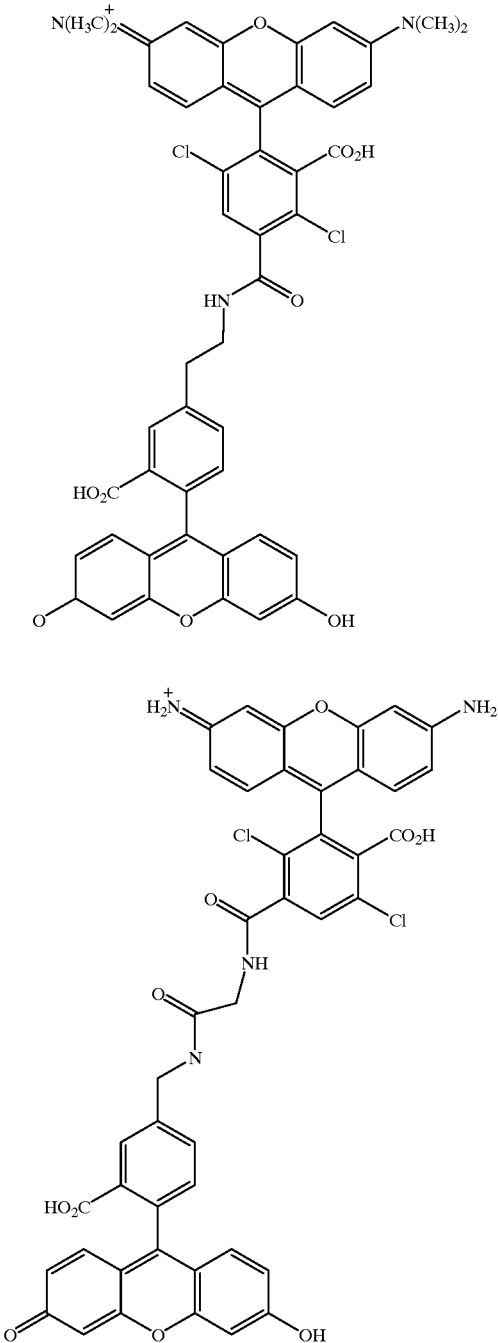

TABLE 5-continued
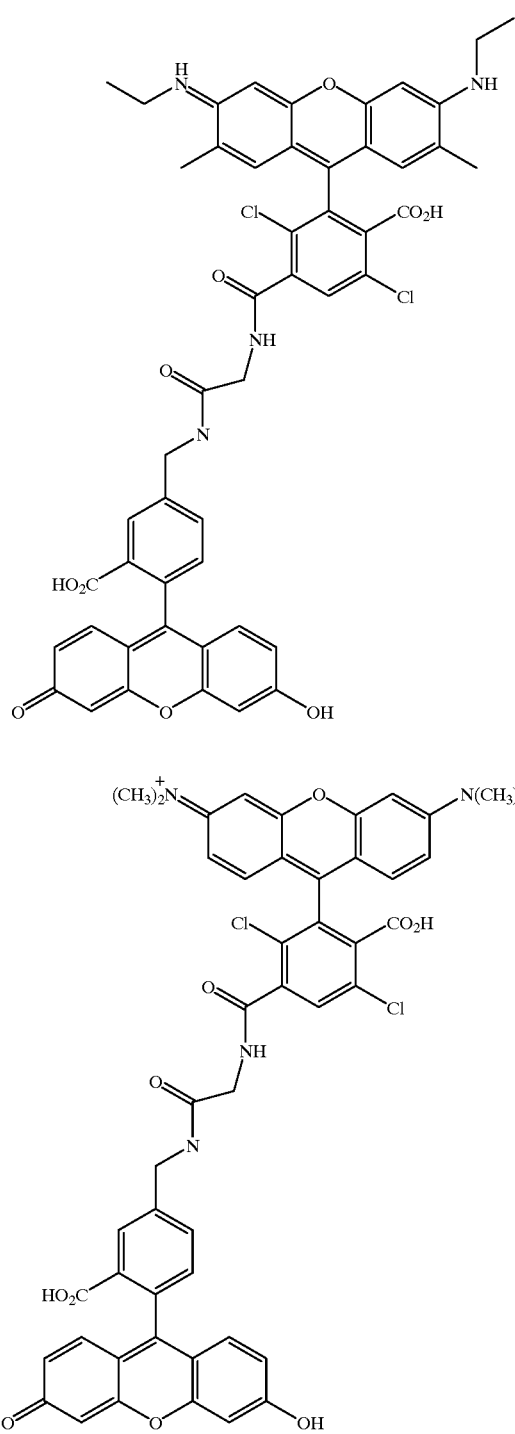
TABLE 5-continued
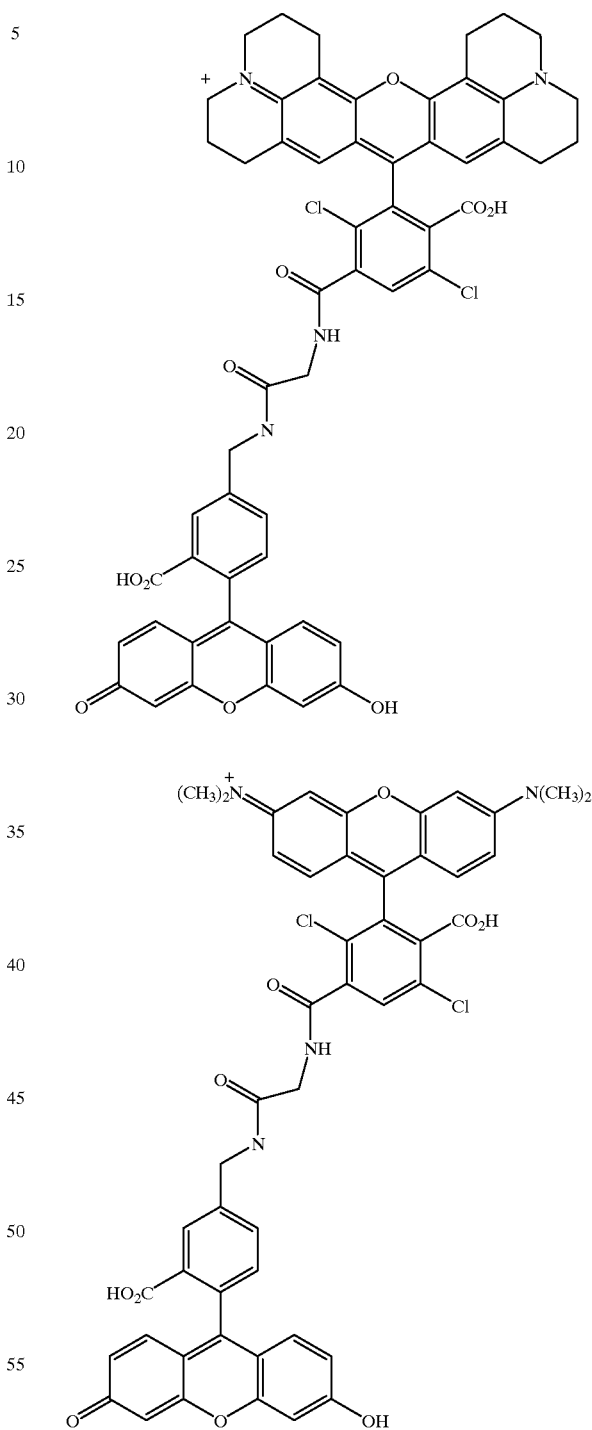

TABLE 5-continued
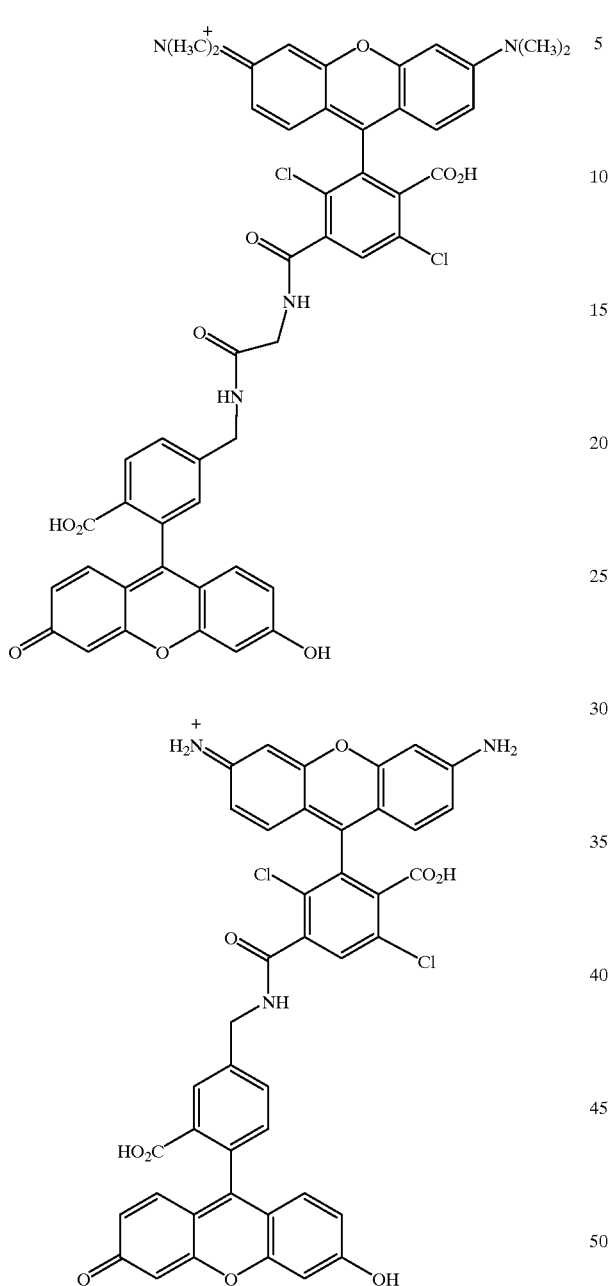
TABLE 5-continued
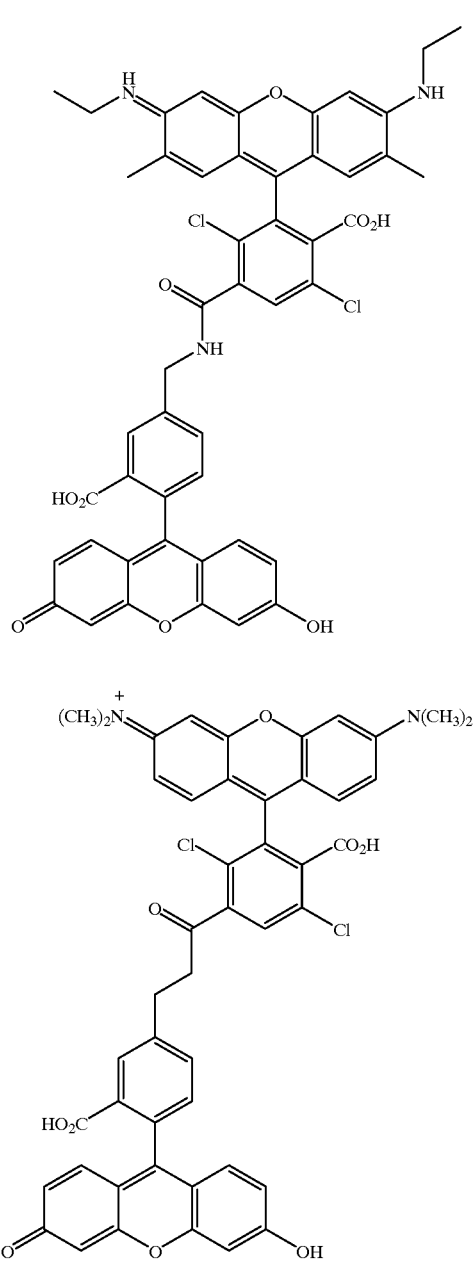

TABLE 5-continued

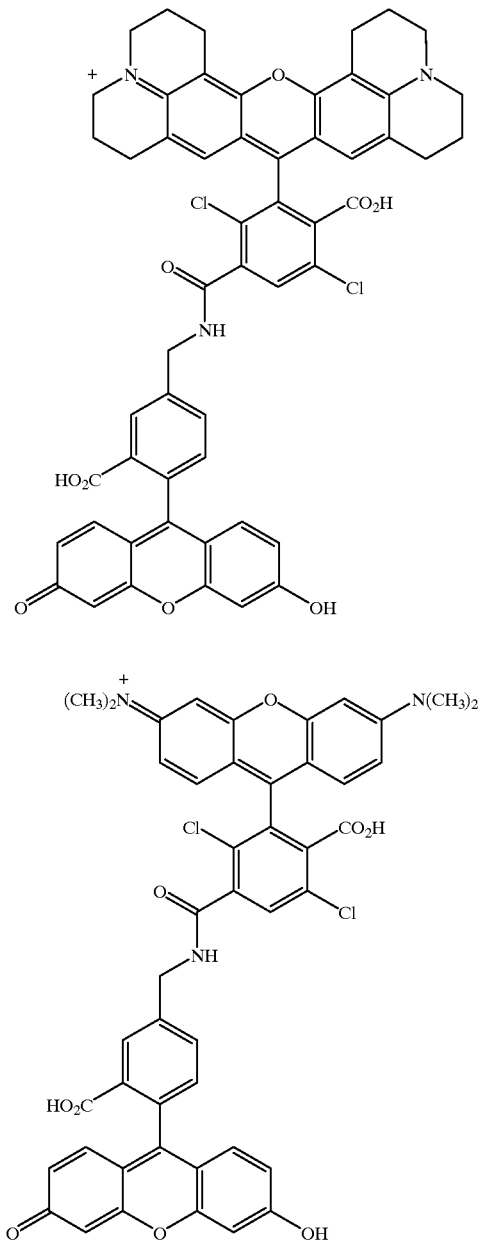

TABLE 5-continued

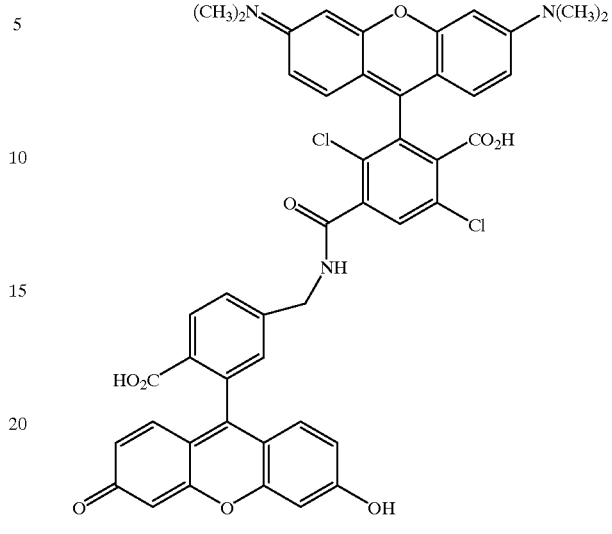

C. Third Class Of Energy Transfer Dyes

The third class of energy transfer fluorescent dyes include a 4,7-dichlororhodamine dye as the acceptor dye and a dye which produces an emission which the 4,7-dichlororhodamine dye can absorb as the donor dye. These dyes exhibit enhanced fluorescence intensity as compared to the acceptor dye alone. In addition, 4,7-dichlororhodamine dyes exhibit a narrower emission spectrum than other rhodamine dyes which facilitates their use in multiple component analyses.

In a preferred embodiment, these energy transfer dyes include those dyes according to the first and second classes of dyes in which the acceptor is a 4,7-dichlororhodamine dye.

1. 4,7-Dichlororhodamine Dyes 4,7-dichlororhodamine dye compounds have the general structure

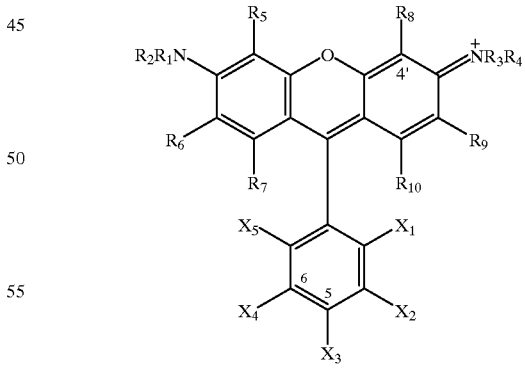

where:

$R_1$–$R_4$ are each independently hydrogen, alkyl or where $R_1$ and $R_5$, $R_2$ and $R_6$, $R_3$ and $R_8$, $R_4$ and $R_9$ are taken together to form a ring, and combinations thereof;

$R_5$–$R_{10}$ are each independently hydrogen, fluorine, chlorine, bromine, iodine, carboxyl, alkyl, alkene, alkyne, sulfonate, sulfone, amino, ammonium, amido, nitrile, alkoxy, phenyl, or substituted phenyl, or where adjacent substituents are taken together to form a ring, and combinations thereof;

$X_1$, $X_3$ and $X_4$ are each independently hydrogen, fluorine, chlorine, bromine, iodine, carboxyl, alkyl, alkene, alkyne, sulfonate, sulfone, amino, ammonium, amido, nitrile, or alkoxy, or where adjacent substituents are taken together to form a ring, and combinations thereof; and $X_2$ and $X_5$ are chlorine.

Dyes falling within the 4,7-dichlororhodamine class of dyes and their synthesis are described in U.S. application Ser. No.: 08/672,196; filed: Jun. 27, 1996; entitled: "4,7-DICHLORORHODAMINE DYES" which is incorporated herein by reference.

With regard to $R_1$–$R_4$, alkyl substituents may include between about 1 to 8 carbon atoms (i.e., methyl, ethyl, propyl, isopropyl, tertbutyl, isobutyl, sec-butyl, neopentyl, tert-pentyl, and the like) and may be straight-chain and branched hydrocarbon moieties. In a preferred embodiment, $R_1$–$R_4$ are each independently either hydrogen, methyl, or ethyl and more preferably either hydrogen or methyl.

With regard to $R_5$–$R_{10}$, alkyl, alkene, alkyne and alkoxy substituents preferably include between about 1 to 8 carbon atoms (i.e., methyl, ethyl, propyl, isopropyl, tert-butyl, isobutyl, sec-butyl, neopentyl, tert-pentyl, and the like) and may be straight-chain and branched hydrocarbon moieties.

With regard to $R_1$–$R_{10}$, $R_1$ and $R_5$, $R_2$ and $R_6$, $R_3$ and $R_8$, $R_4$ and $R_9$ may each independently be taken together to form a 5, 6, or 7 membered ring.

In one embodiment, $R_6$ and $R_7$ is benzo, and/or, $R_9$ and $R_{10}$ is benzo. In a preferred embodiment, $R_5$–$R_{10}$ are each independently either hydrogen, methyl, or ethyl and more preferably either hydrogen or methyl.

With regard to $X_1$, $X_3$ and $X_4$, $X_1$ is preferably a carboxylate and one of $X_3$ and $X_4$ may include a substituent which is used to link the 4,7-dichlororhodamine acceptor dye to a donor dye or to link a nucleotide or an oligonucleotide to the energy transfer dye. The $R_8$ substituent at the 4' ring position may also be used to link the acceptor to either the donor dye or to a biomolecule such as a nucleotide or oligonucleotide.

In one particularly preferred acceptor dye that may be used in the present invention, referred to herein as DR110-2, $R_1$–$R_{10}$ taken separately are hydrogen, $X_1$ is carboxylate, and one of $X_3$ and $X_4$ is a linking group (L), the other being hydrogen. The structure of DR110-2 is shown below.

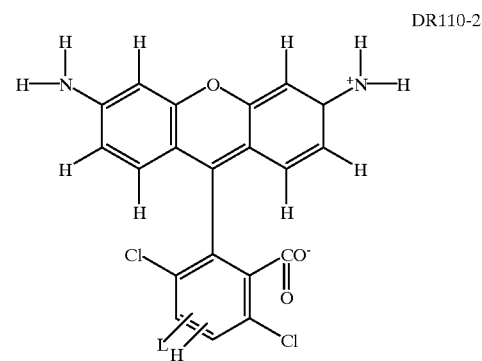

In a second particularly preferred acceptor dye that may be used in the present invention, referred to herein as DR6G-2, one of $R_1$ and $R_2$ is ethyl, the other being hydrogen, one of $R_3$ and $R_4$ is ethyl, the other being hydrogen, $R_5$ and $R_8$ taken separately are methyl, $R_6$, $R_7$, $R_9$, and $R_{10}$ are hydrogen, $X_1$ is carboxylate, and one of $X_3$ and $X_4$ is a linking group, the other being hydrogen. The structure of DR6G-2 is shown below.

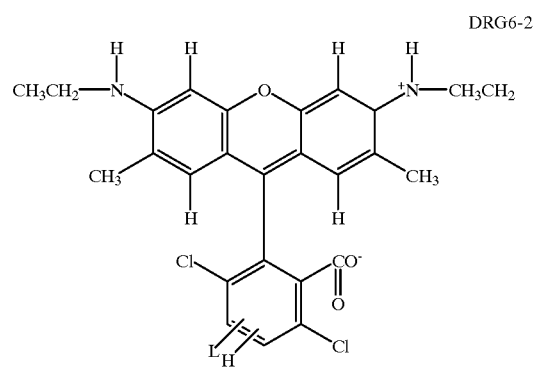

In a third particularly preferred acceptor dye that may be used in the present invention, referred to herein as DTMR, $R_1$–$R_6$ taken separately are hydrogen, $Y_1$–$Y_4$ taken separately are methyl, $X_1$ is carboxylate, and one of $X_2$ and $X_3$ is linking group, the other being hydrogen. The structure of DTMR is shown below.

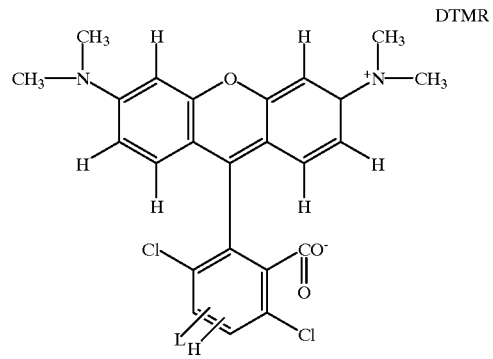

In a fourth particularly preferred acceptor dye that may be used in the present invention, referred to herein as DROX, $R_1$ and $R_6$ are taken together to form a six membered ring, $R_2$ and $R_5$ are taken together to form a six membered ring, $R_3$ and $R_7$ are taken together to form a six membered ring, $R_4$ and $R_8$ are taken together to form a six membered ring, $R_5$ and $R_6$ are hydrogen, $X_1$ is carboxylate, and one of $X_3$ and $X_4$ is a linking group, the other being hydrogen. The structure of DROX is shown below.

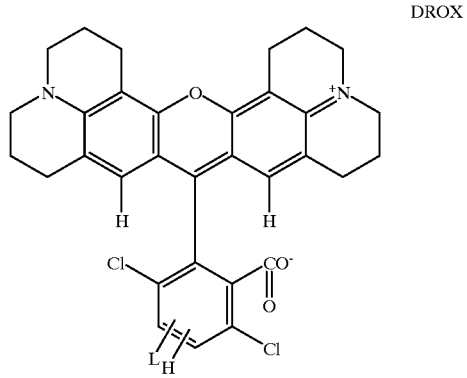

DROX

FIGS. 3A and 3B show several additional preferred embodiments of 4,7-dichlororhodamine dyes which can be used in the energy transfer dyes of the present invention.

In compound 3A-A, one of $R_1$ and $R_2$ is ethyl, the other being hydrogen, $R_3$ and $R_4$ taken separately are hydrogen, $R_6$ is methyl, and $R_7$–$R_{10}$ taken separately are hydrogen, $X_1$ is carboxylate, and one of $X_3$ and $X_4$ is a linking group, the other being hydrogen.

In compound 3A-B, one of $R_1$ and $R_2$ is ethyl, the other being hydrogen, $R_3$ and $R_4$ taken separately are methyl, $R_5$ is methyl, $R_6$–$R_{10}$ taken separately are hydrogen, $X_1$ is carboxylate, and, one of $X_3$ and $X_4$ is a linking group, the other being hydrogen.

In compound 3A-C, $R_1$ and $R_2$ taken separately are methyl, $R_3$ and $R_7$ taken together form a six membered ring, $R_4$ and $R_8$ taken together form a six membered ring, $R_5$, $R_6$, $R_7$, and $R_{10}$ taken separately are hydrogen, $X_1$ is carboxylate, and, one of $X_3$ and $X_4$ is a linking group, the other being hydrogen.

In compound 3B-D, $R_1$ and $R_2$ taken separately are hydrogen, $R_3$ and $R_9$ taken together form a six membered ring, $R_4$ and $R_8$ taken together form a six membered ring, $R_5$, $R_6$, $R_7$, and $R_{10}$ taken separately are hydrogen, $X_1$ is carboxylate, and one of $X_3$ and $X_4$ is a linking group, the other being hydrogen.

In compound 3B-E, one of $R_1$ and $R_2$ is ethyl, the other being hydrogen, $R_3$ and $R_9$ taken together form a six membered ring, $R_4$ and $R_8$ taken together form a six membered ring, $R_5$ is methyl, $R_6$, $R_7$ and $R_{10}$ taken separately are hydrogen, $X_1$ is carboxylate, and, one of $X_3$ and $X_4$ is a linking group, the other being hydrogen.

In compound 3B-F, $R_1$ and $R_2$ taken separately are hydrogen, $R_3$ and $R_4$ taken separately are methyl, $R_5$–$R_{10}$ taken separately are hydrogen, $X_1$ is carboxylate, and, one of $X_3$ and $X_4$ is linking group, the other being hydrogen.

FIGS. 4A and 4B show preferred generalized synthesis schemes for the preparation of 4,7-dichlororhodamine dyes used in the energy transfer dyes of this invention. The variable substituents indicated in each figure are as previously defined.

FIG. 4A shows a generalized synthesis wherein the substituent $X_1$ can be other than carboxylate. In the figure, X' indicates moieties which are precursors to $X_1$. In the method illustrated in FIG. 4A, two equivalents of a 3-aminophenol derivative 4A-A/4A-B, such as 3-dimethylaminophenol, is reacted with one equivalent of a dichlorobenzene derivative 4A-C, e.g., 4-carboxy-3,6,dichloro-2-sulfobenzoic acid cyclic anhydride, i.e., where the $X_1'$ moieties of 4c taken together are,

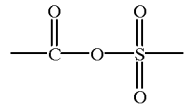

The reactants are then heated for 12 h in a strong acid, e.g., polyphosphoric acid or sulfuric acid, at 180° C. The crude dye 4A-D is precipitated by addition to water and isolated by centrifugation. To form a symmetrical product, the substituents of reactants 4A-A and 4A-B are the same, while to form an asymmetrical product, the substituents are different.

FIG. 4B shows a generalized synthesis wherein the substituent $X_1$ is carboxylate. In the method of FIG. 4B, two equivalents of a 3-aminophenol derivative 4A-A/4A-B, such as 3-dimethylaminophenol, is reacted with one equivalent of a phthalic anhydride derivative 4B-E, e.g. 3,6-dichlorotrimellitic acid anhydride. The reactants are then heated for 12 h in a strong acid, e.g., polyphosphoric acid or sulfuric acid, at 180° C. The crude dye 4A-D is precipitated by addition to water and isolated by centrifugation. To form a symmetrical product, the substituents of reactants 4A-A and 4A-B are the same, while to form an asymmetrical product, the substituents are different.

2. Energy Transfer Dyes With 4,7-Dichlororhodamine As The Acceptor

In general, the energy transfer dyes of the present invention include a donor dye which absorbs light at a first wavelength and emits excitation energy in response, a 4,7-dichlororhodamine acceptor dye which is capable of absorbing the excitation energy emitted by the donor dye and fluorescing at a second wavelength in response, and a linker which attaches the donor dye to the acceptor dye. Prefered examples of this class of dyes which use a 4,7-dichlororhodamine dye as the acceptor dye is illustrated in Table 1.

Examples of acceptor dyes which may be used in this class of dyes include, but are not limited to DR110-2, DR6G-2, DTMR, DROX, as illustrated above, as well as the dyes illustrated in FIGS. 3A–3B.

One subclass of these energy transfer fluorescent dyes are the dyes according to the first class of dyes of the present invention in which the acceptor dye is a 4,7-dichlororhodamine dye. The general structure of these dyes is illustrated below.

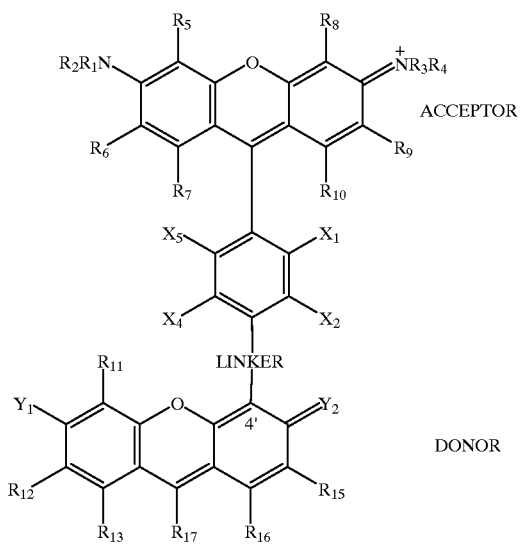

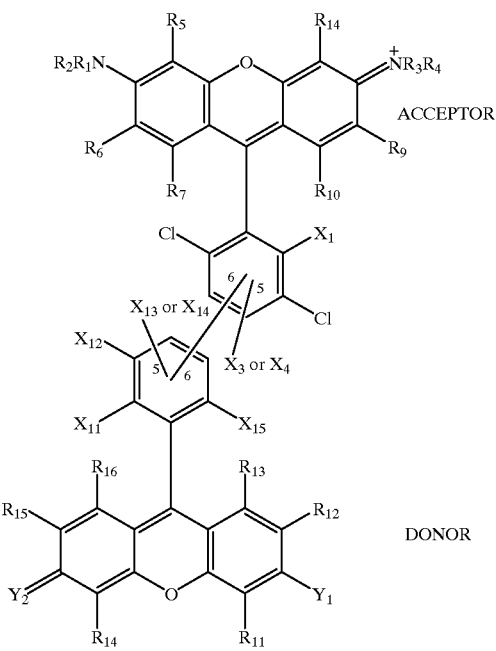

Table 4 provides examples of the energy transfer dyes belonging to the first class of dyes in which a 4,7 dichlororhodamine is used as the acceptor dye. It is noted that although the dyes illustrated in Table 4 include a 5-carboxyfluorescein donor dye and a 5 or 6 carboxy DTMR as the acceptor dye, it should be understood that a wide variety of other xanthene dyes can be readily substituted as the donor dye and a wide variety of other 4,7-dichlororhodamine dyes can be readily substituted for the DTMR acceptor dye, all of these variations with regard to the donor and acceptor dyes being intended to fall within the scope of the invention.

Another subclass of these energy transfer fluorescent dyes are the dyes according to the second class of dyes of the present invention in which the acceptor dye is a 4,7-dichlororhodamine dye. The general structure of these dyes where the donor xanthene dye and acceptor 4,7-dichlororhodamine dye are linked to each other at either the five or six ring positions of the donor and acceptor dyes is illustrated below.

As described above, in this embodiment, the linker attaching the donor to the acceptor dye is preferably short and/or rigid as this has been found to enhance the transfer of energy between the donor and acceptor dyes. The substituent labels shown above correspond to the same groups of substituents as has been specified with regard to the other dyes.

Table 5 provides examples of the second class of energy transfer dyes according to the present invention in which 4,7 dichlororhodamine is used as the acceptor dye. It is noted that although the dyes illustrated in Table 5 include a 5-aminomethylfluorescein donor dye, it should be understood that a wide variety of other xanthene dyes can be readily substituted as the donor dye. It should also be understood that a wide variety of other 4,7-dichlororhodamine dyes can be readily substituted for the acceptor dye shown in Table 5 since, as has been described above, all of these variations with regard to the donor and acceptor dyes are intended to fall within the scope of the invention.

D. Fourth Class Of Energy Transfer Dyes

The present invention also relates to a fourth class of energy transfer fluorescent dyes in which the donor dye is a member of the xanthene class of dyes, and the acceptor dye is a member of the xanthene, cyanine, phthalocyanine or squaraine classes of dyes. Within this class of energy transfer dyes, it is preferred that the donor be a member of the fluorescein class of dyes and the acceptor dye have an emission maximum that is greater than about 600 nm and/or an emission maximum that is at least about 100 nm greater than the absorbance maximum of the donor dye.

The fourth class of dyes of the present invention exhibit unusually large Stoke shifts, as measured by the difference between the absorbance of the donor and the emission of the acceptor. In addition, these dyes exhibit efficient energy transfer in that minimal donor fluorescence is observed. Interestingly, energy is transfered from the donor to the acceptor in some of the dyes belonging to this class even though the absorbance spectrum of the acceptor dye does not overlap with the emission spectrum of the donor dye.

Examples of acceptor dyes which may be used in this embodiment include, but are not limited to 5-carboxy-X-rhodamine (ROX) and Cy5.

The energy transfer dyes of this embodiment also include a linker which attaches the donor to the acceptor. The linker used to attach the donor to the acceptor dye may be any linker according to the first and second classes of dyes. However, it is foreseen that alternate linkers may be used in this class of dyes.

In one embodiment of this class of dyes, the linker is attached to the 4' position of the donor dye's xanthene ring structure. The linker preferably has a general structure $R_{21}Z_1C(O)R_{22}R_{28}$, as described above where $R_{21}$ is a $C_{1-5}$ alkyl which is attached to the 4' ring position of the donor xanthene dye, $Z_1$ is either NH, sulfur or oxygen, C(O) is a carbonyl group, $R_22$ is a substituent which includes an alkene, diene, alkyne, a five and six membered ring having at least one unsaturated bond or a fused ring structure which is attached to the carbonyl carbon, and $R_{28}$ is a functional group which attaches the linker to the acceptor dye. In cases where the acceptor dye is a member of the xanthene class of dyes, the linker is preferably attached to acceptor at the 5 position of the xanthene ring structure.

Table 6 provides examples of the above-described energy transfer dyes according to the present invention. It is noted that although the dyes illustrated in Table 6 include a 5-carboxyfluorescein donor dye it should be understood that a wide variety of other xanthene dyes can be readily substituted as the donor dye. It should also be understood that a wide variety of other xanthene dyes, as well as cyanine, phthalocyanine and squaraine dyes can be readily substituted for the 5-carboxy ROX and Cy5 acceptor dyes, as has been described above, all of these variations with regard to the donor and acceptor dyes falling within the scope of the invention.

Figure 5:
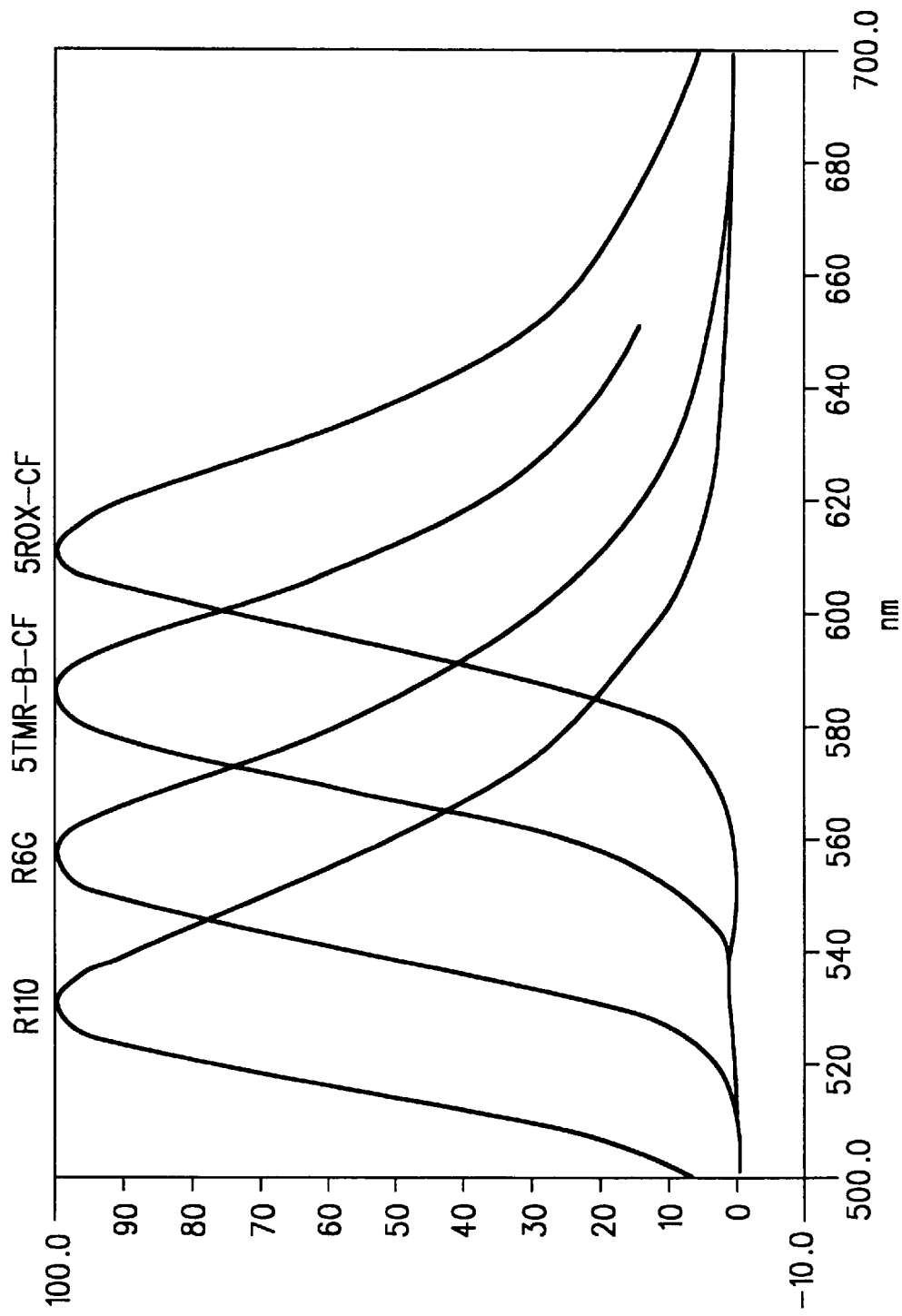
FIG. 5 illustrates a set of four dyes (3-carboxy-R110, 5-carboxy-R6G, 5TMR-B-CF and 5ROX-CF) which are spectrally resolvable from each other.
Figure 6:
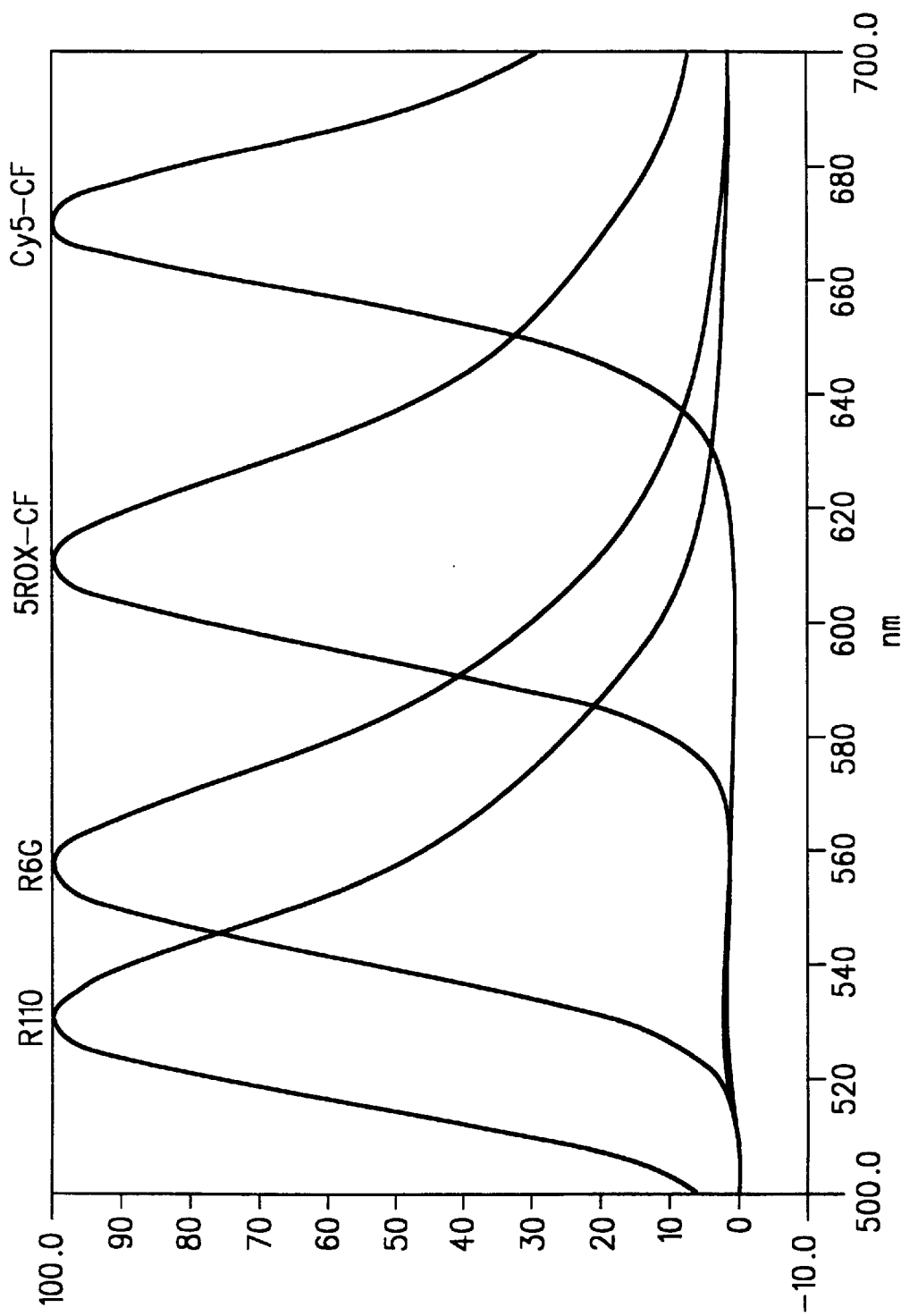
FIG. 6 illustrates a set of four dyes (3-carboxy-R110, 5-carboxy-R6G, 5ROX-CF and Cy5-CF) which are spectrally resolvable from each other.

The energy transfer dyes of this embodiment exhibit unusually large Stoke shifts which make these dyes particularly well suited for use with dyes having smaller Stoke shifts in four dye DNA sequencing. For example, FIGS. 5 and 6 illustrate two sets of four dyes which are spectrally resolvable from each other. Within FIG. 5, 5ROX-CF is a dye falling within the scope of the fourth class of dyes described above. Meanwhile, FIG. 6 includes 6ROX-CF and Cy5-CF which both fall within the scope of the fourth class of dyes described above.

As can be seen from the emission spectra of 5ROX-CF and Cy5-CF illustrated in FIG. 6, very little fluorescence from the donor dye (5-carboxyfluorescein, 520 nm) is observed in these dyes. This is an unexpected result in view of the large difference between the emission maximum of the donor dye (fluorescein) and the absorbance maximum of the acceptor dyes (ROX, 590 nm, Cy5, 640 nm).

TABLE 6

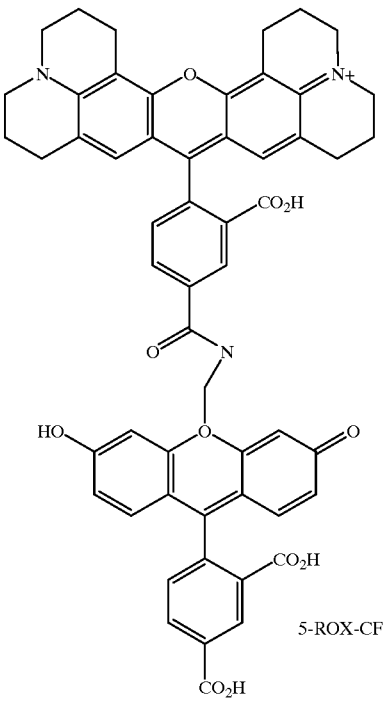

5-ROX-CF

TABLE 6-continued

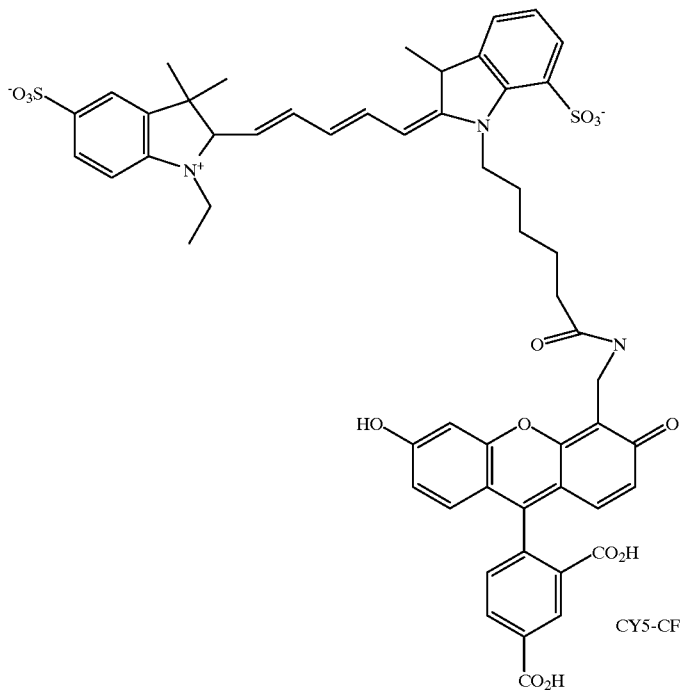

CY5-CF

II. Reagents Including Energy Transfer Dyes Of The Present Invention

The present invention also relates to fluorescent reagents which incorporate an energy transfer fluorescent dye according to the present invention. As described in greater detail in Section III, these reagents may be used in a wide variety of methods for detecting the presence of a component in a sample.

The fluorescent reagents of the present invention include any molecule or material to which the energy transfer dyes of the invention can be attached and used to detect the presence of the reagent based on the fluorescence of the energy transfer dye. Types of molecules and materials to which the dyes of the present invention may be attached to form a reagent include, but are not limited to proteins, polypeptides, polysaccharides, nucleotides, nucleosides, oligonucleotides, oligonucleotide analogs (such as a peptide nucleic acid), lipids, solid supports, organic and inorganic polymers, and combinations and assemblages thereof, such as chromosomes, nuclei, living cells, such as bacteria, other microorganisms, mammalian cells, and tissues.

Preferred classes of reagents of the present invention are nucleotides, nucleosides, oligonucleotides and oligonucleotide analogs which have been modified to include an energy transfer dye of the invention. Examples of uses for nucleotide and nucleoside reagents include, but are not limited to, labeling oligonucleotides formed by enzymatic synthesis, e.g., nucleoside triphosphates used in the context of PCR amplification, Sanger-type oligonucleotide sequencing, and nick-translation reactions. Examples of uses for oligonucleotide reagents include, but are not limited to, as DNA sequencing primers, PCR primers, oligonucleotide hybridization probes, and the like.

One particular embodiment of the reagents are labeled nucleosides (NTP), such as cytosine, adenosine, guanosine, and thymidine, labeled with an energy transfer fluorescent dye of the present invention. These reagents may be used in a wide variety of methods involving oligonucleotide synthesis. Another related embodiment are labeled nucleotides, e.g., mono-, di- and triphosphate nucleoside phosphate esters. These reagents include, in particular, deoxynucleoside triphosphates (dNTP), such as deoxycytosine triphosphate, deoxyadenosine triphosphate, deoxyguanosine triphosphate, and deoxythymidine triphosphate, labeled with an energy transfer fluorescent dye of the present invention. These reagents may be used, for example, as polymerase substrates in the preparation of dye labeled oligonucleotides. These reagents also include labeled dideoxynucleoside triphosphates (ddNTP), such as dideoxycytosine triphosphate, dideoxyadenosine triphosphate, dideoxyguanosine triphosphate, and dideoxythymidine triphosphate, labeled with an energy transfer fluorescent dye of the present invention. These reagents may be used, for example, in dye termination sequencing.

Another embodiment of reagents are oligonucleotides which includes an energy transfer fluorescent dye of the present invention. These reagents may be used, for example, in dye primer sequencing.

As used herein, "nucleoside" refers to a compound consisting of a purine, deazapurine, or pyrimidine nucleoside base, e.g., adenine, guanine, cytosine, uracil, thymine, deazaadenine, deazaguanosine, and the like, linked to a pentose at the 1' position, including 2'-deoxy and 2'-hydroxyl forms, e.g. as described in Kornberg and Baker, *DNA Replication*, 2nd Ed. (Freeman, San Francisco, 1992). The term "nucleotide" as used herein refers to a phosphate ester of a nucleoside, e.g., mono, di and triphosphate esters, wherein the most common site of esterification is the hydroxyl group attached to the C-5 position of the pentose. "Analogs" in reference to nucleosides include synthetic nucleosides having modified base moieties and/or modified sugar moieties, e.g. described generally by Scheit, *Nucleotide Analogs* (John Wiley, New York, 1980). The terms "labeled nucleoside" and "labeled nucleotide" refer to nucleosides and nucleotides which are covalently attached to an energy transfer dye through a linkage.

As used herein, the term "oligonucleotide" refers to linear polymers of natural or modified nucleoside monomers, including double and single stranded deoxyribonucleosides, ribonucleosides, α-anomeric forms thereof, and the like. Usually the nucleoside monomers are linked by phosphodiester linkages, where as used herein, the term "phosphodiester linkage" refers to phosphodiester bonds or analogs thereof including phosphorothioate, phosphorodithioate, phosphoroselenoate, phosphorodiselenoate, phosphoroanilothioate, phosphoranilidate, phosphoramidate, and the like, including associated counterions, e.g., H, NH$_4$, Na, and the like if such counterions are present. The oligonucleotides range in size form a few monomeric units, e.g. 8–40, to several thousands of monomeric units. Whenever an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted.

Nucleoside labeling can be accomplished using any of a large number of known nucleoside labeling techniques using known linkages, linking groups, and associated complementary functionalities. The linkage linking the dye and nucleoside should (i) be stable to oligonucleotide synthesis conditions, (ii) not interfere with oligonucleotide-target hybridization, (iii) be compatible with relevant enzymes, e.g., polymerases, ligases, and the like, and (iv) not quench the fluorescence of the dye.

Preferably, the dyes are covalently linked to the 5-carbon of pyrimidine bases and to the 7-carbon of 7-deazapurine bases. Several suitable base labeling procedures have been reported that can be used with the invention, e.g. Gibson et al, *Nucleic Acids Research*, 14 6455–6467 (1987); Gebeyehu et al, *Nucleic Acids Research*, 15 4513–4535 (1987); Haralambidis et al, *Nucleic Acids Research*, 15 4856–4876 (1987); Nelson et al., *Nucleosides and Nucleotides*, 5(3) 233–241 (1986); Bergstrom, et al., *JACS*, 111 374–375 (1989); U.S. Pat. Nos. 4,855,225, 5,231,191, and 5,449,767, each of which is incorporated herein by reference.

Preferably, the linkages are acetylenic amido or alkenic amido linkages, the linkage between the dye and the nucleotide base being formed by reacting an activated N-hydroxysuccinimide (NHS) ester of the dye with an alkynylamino-, alkynylethoxyamino- or alkenylamino-derivatized base of a nucleotide. More preferably, the resulting linkage is proargyl-1-ethoxyamido (3-(amino)ethoxy-1-propynyl), 3-(carboxy)amino-1-propynyl or 3-amino-1-propyn-1-yl.

Several preferred linkages for linking the dyes of the invention to a nucleoside base are shown below.

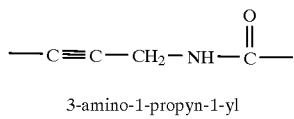

3-amino-1-propyn-1-yl

-continued

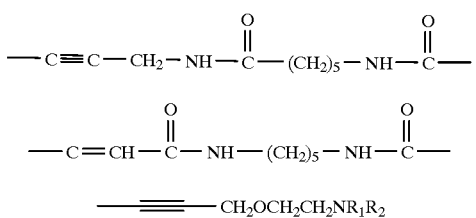

where R$_1$ and R$_2$ taken separately are H, alkyl, a protecting group or a fluorescent dye.

The synthesis of alkynylamino-derivatized nucleosides is taught by Hobbs et al. in European Patent Application No. 87305844.0, and Hobbs et al., *J. Org. Chem.*, 54 3420 (1989), which is incorporated herein by reference. Briefly, the alkynylamino-derivatized nucleotides are formed by placing the appropriate halodideoxynucleoside (usually 5-iodopyrimidine and 7-iodo-7-deazapurine dideoxynucleosides as taught by Hobbs et al. (cited above)) and Cu(I) in a flask, flushing with argon to remove air, adding dry DMF, followed by addition of an alkynylamine, triethyl-amine and Pd(0). The reaction mixture can be stirred for several hours, or until thin layer chromatography indicates consumption of the halodideoxynucleoside. When an unprotected alkynylamine is used, the alkynylamino-nucleoside can be isolated by concentrating the reaction mixture and chromatographing on silica gel using an eluting solvent which contains ammonium hydroxide to neutralize the hydrohalide generated in the coupling reaction. When a protected alkynylamine is used, methanolimethylene chloride can be added to the reaction mixture, followed by the bicarbonate form of a strongly basic anion exchange resin. The slurry can then be stirred for about 45 minutes, filtered, and the resin rinsed with additional methanol/methylene chloride. The combined filtrates can be concentrated and purified by flash-chromatography on silica gel using a methanolmethylene chloride gradient. The triphosphates are obtained by standard techniques.

The synthesis of oligonucleotides labeled with an energy transfer dye of the present invention can be accomplished using any of a large number of known oligonucleotide labeling techniques using known linkages, linking groups, and associated complementary functionalities. For example, labeled oligonucleotides may be synthesized enzymatically, e.g., using a DNA polymerase or ligase, e.g., Stryer, *Biochemistry*, Chapter 24, W.H. Freeman and Company (1981), or by chemical synthesis, e.g., by a phosphoramidite method, a phosphitetriester method, and the like, e.g., Gait, *Oligonucleotide Synthesis*, IRL Press (1990). Labels may be introduced during enzymatic synthesis utilizing labeled nucleoside triphosphate monomers, or introduced during chemical synthesis using labeled non-nucleotide or nucleotide phosphoramidites, or may be introduced subsequent to synthesis.

Generally, if the labeled oligonucleotide is made using enzymatic synthesis, the following procedure may be used. A template DNA is denatured and an oligonucleotide primer is annealed to the template DNA. A mixture of deoxynucleoside triphosphates is added to the reaction including dGTP, dATP, dCTP, and dTTP where at least a fraction of one of the deoxynucleotides is labeled with a dye compound of the invention as described above. Next, a polymerase enzyme is added under conditions where the polymerase enzyme is active. A labeled polynucleotide is formed by the incorporation of the labeled deoxynucleotides during polymerase strand synthesis. In an alternative enzymatic synthesis method, two primers are used instead of one, one primer complementary to the + strand and the other complementary to the − strand of the target, the polymerase is a thermostable polymerase, and the reaction temperature is cycled between a denaturation temperature and an extension temperature, thereby exponentially synthesizing a labeled complement to the target sequence by PCR, e.g., *PCR Protocols,* Innis et al. eds., Academic Press (1990).

Generally, if the labeled oligonucleotide is made using a chemical synthesis, it is preferred that a phosphoramidite method be used. Phosphoramidite compounds and the phosphoramidite method of polynucleotide synthesis are preferred in synthesizing oligonucleotides because of the efficient and rapid coupling and the stability of the starting materials. The synthesis is performed with the growing oligonucleotide chain attached to a solid support, so that excess reagents, which are in the liquid phase, can be easily removed by filtration, thereby eliminating the need for purification steps between cycles.

In view of the utility of phosphoramidite reagents in labeling nucleosides and oligonucleotides, the present invention also relates to phosphoramidite compounds which include an energy transfer dye of the present invention.

Detailed descriptions of the chemistry used to form oligonucleotides by the phosphoramidite method are provided in Caruthers et al., U.S. Pat. No. 4,458,066; Caruthers et al., U.S. Pat. No. 4,415,732; Caruthers et al., *Genetic Engineering,* 41–17 (1982); *Users Manual Model* 392 and 394 *Polynucleotide Synthesizers,* pages 6-1 through 6-22, Applied Biosystems, Part No. 901237 (1991), each of which are incorporated by reference in their entirety.

The following briefly describes the steps of a typical oligonucleotide synthesis cycle using the phosphoramidite method. First, a solid support including a protected nucleotide monomer is treated with acid, e.g., trichloroacetic acid, to remove a 5'-hydroxyl protecting group, freeing the hydroxyl for a subsequent coupling reaction. An activated intermediate is then formed by simultaneously adding a protected phosphoramidite nucleoside monomer and a weak acid, e.g., tetrazole, to the reaction. The weak acid protonates the nitrogen of the phosphoramidite forming a reactive intermediate. Nucleoside addition is complete within 30 s. Next, a capping step is performed which terminates any polynucleotide chains that did not undergo nucleoside addition. Capping is preferably done with acetic anhydride and 1-methylimidazole. The internucleotide linkage is then converted from the phosphite to the more stable phosphotriester by oxidation using iodine as the preferred oxidizing agent and water as the oxygen donor. After oxidation, the hydroxyl protecting group is removed with a protic acid, e.g., trichloroacetic acid or dichloroacetic acid, and the cycle is repeated until chain elongation is complete. After synthesis, the polynucleotide chain is cleaved from the support using a base, e.g., ammonium hydroxide or t-butyl amine. The cleavage reaction also removes any phosphate protecting groups, e.g., cyanoethyl. Finally, the protecting groups on the exocyclic amines of the bases and the hydroxyl protecting groups on the dyes are removed by treating the polynucleotide solution in base at an elevated temperature, e.g., 55° C.

Any of the phosphoramidite nucleoside monomers may be dyelabeled phosphoramidites. If the 5'-terminal position of the nucleotide is labeled, a labeled non-nucleotidic phosphoramidite of the invention may be used during the final condensation step. If an internal position of the oligonucleotide is to be labeled, a labeled nucleotidic phosphoramidite of the invention may be used during any of the condensation steps.

Subsequent to their synthesis, oligonucleotides may be labeled at a number of positions including the 5'-terminus. See *Oligonucleotides and Analogs,* Eckstein ed., Chapter 8, IRL Press (1991) and Orgel et al., *Nucleic Acids Research* 11(18) 6513 (1983); U.S. Pat. No. 5,118,800, each of which are incorporated by reference Oligonucleotides may also be labeled on their phosphodiester backbone (*Oligonucleotides and Analogs,* Eckstein ed., Chapter 9) or at the 3'-terminus (Nelson, *Nucleic Acids Research* 20(23) 6253–6259, and U.S. Pat. Nos. 5,401,837 and 5,141,813, both patents hereby incorporated by reference. For a review of oligonucleotide labeling procedures see R. Haugland in *Excited States of Biopolymers,* Steiner ed., Plenum Press, NY (1983).

In one preferred post-synthesis chemical labeling method an oligonucleotide is labeled as follows. A dye including a carboxy linking group is converted to the n-hydroxysuccinimide ester by reacting with approximately 1 equivalent of 1,3-dicyclohexylcarbodiimide and approximately 3 equivalents of n-hydroxysuccinimide in dry ethyl acetate for 3 hours at room temperature. The reaction mixture is washed with 5% HCl, dried over magnesium sulfate, filtered, and concentrated to a solid which is resuspended in DMSO. The DMSO dye stock is then added in excess (10–20 ×) to an aminohexyl derivatized oligonucleotide in 0.25 M bicarbonate/carbonate buffer at pH 9.4 and allowed to react for 6 hours, e.g., U.S. Pat. No. 4,757,141. The dye labeled oligonucleotide is separated from unreacted dye by passage through a size-exclusion chromatography column eluting with buffer, e.g., 0.1 molar triethylamine acetate (TEM). The fraction containing the crude labeled oligonucleotide is further purified by reverse phase HPLC employing gradient elution.

III. Methods Employing Dyes And Reagents Of The Present Invention

The energy transfer dyes and reagents of the present invention may be used in a wide variety of methods for detecting the presence of a component in a sample by labeling the component in the sample with a reagent containing the dye. In particular, the energy transfer dyes and reagents of the present invention are well suited for use in methods which combine separation and fluorescent detection techniques, particularly methods requiring the simultaneous detection of multiple spatially-overlapping analytes. For example, the dyes and reagents are particularly well suited for identifying classes of oligonucleotides that have been subjected to a biochemical separation procedure, such as electrophoresis, where a series of bands or spots of target substances having similar physiochemical properties, e.g. size, conformation, charge, hydrophobicity, or the like, are present in a linear or planar arrangement. As used herein, the term "bands" includes any spatial grouping or aggregation of analytes on the basis of similar or identical physiochemical properties. Usually bands arise in the separation of dye-oligonucleotide conjugates by electrophoresis.

Classes of oligonucleotides can arise in a variety of contexts. In a preferred category of methods referred to herein as "fragment analysis" or "genetic analysis" methods, labeled oligonucleotide fragments are generated through template-directed enzymatic synthesis using labeled primers or nucleotides, e.g., by ligation or polymerase-directed primer extension; the fragments are subjected to a size-dependent separation process, e.g., electrophoresis or chromatography; and, the separated fragments are detected subsequent to the separation, e.g., by laser-induced fluorescence. In a particularly preferred embodiment, multiple classes of oligonucleotides are separated simultaneously and the different classes are distinguished by spectrally resolvable labels.

One such fragment analysis method is amplified fragment length polymorphisim detection (AmpFLP) and is based on amplified fragment length polymorphisms, i.e., restriction fragment length polymorphisms that are amplified by PCR. These amplified fragments of varying size serve as linked markers for following mutant genes through families. The closer the amplified fragment is to the mutant gene on the chromosome, the higher the linkage correlation. Because genes for many genetic disorders have not been identified, these linkage markers serve to help evaluate disease risk or paternity. In the AmpFLPs technique, the polynucleotides may be labeled by using a labeled oligonucleotide PCR primer, or by utilizing labeled nucleotide triphosphates in the PCR.

Another fragment analysis method is nick translation. Nick translation involves a reaction to replace unlabeled nucleotide triphosphates in a double-stranded DNA molecule with labeled ones. Free 3'-hydroxyl groups are created within the unlabeled DNA by "nicks" caused by deoxyribonuclease I (DNAase I) treatment. DNA polymerase I then catalyzes the addition of a labeled nucleotide to the 3'-hydroxyl terminus of the nick. At the same time, the 5' to 3'-exonuclease activity of this enzyme eliminates the nucleotide unit from the 5'-phosphoryl terminus of the nick. A new nucleotide with a free 3'-OH group is incorporated at the position of the original excised nucteotide, and the nick is shifted along by one nucleotide unit in the 3' direction. This 3' shift will result in the sequential addition of new labeled nucleotides to the DNA with the removal of existing unlabeled nucleotides. The nick-translated polynucleotide is then analyzed using a separation process, e.g., electrophoresis.

Another exemplary fragment analysis method is based on variable number of tandem repeats, or VNTRs. VNTRs are regions of double-stranded DNA that contain adjacent multiple copies of a particular sequence, with the number of repeating units being variable. Examples of VNTR loci are pYNZ22, pMCT118, and Apo B. A subset of VNTR methods are those methods based on the detection of microsatellite repeats, or short tandem repeats (STRs), i.e., tandem repeats of DNA characterized by a short (24 bases) repeated sequence. One of the most abundant interspersed repetitive DNA families in humans is the (dC-dA)n--(dG-dT)n dinucleotide repeat family (also called the (CA)n dinucleotide repeat family). There are thought to be as many as 50,000 to 100,000 (CA)n repeat regions in the human genome, typically with 15–30 repeats per block. Many of these repeat regions are polymorphic in length and can therefore serve as useful genetic markers. Preferably, in VNTR or STR methods, label is introduced into the polynucleotide fragments by using a dye-labeled PCR primer.

Another exemplary fragment analysis method is DNA sequencing. In general, DNA sequencing involves an extension/termination reaction of an oligonucleotide primer. Included in the reaction mixture are deoxynucleoside triphosphates (dNTPs) which are used to extend the primer. Also included in the reaction mixture is at least one dideoxynucleoside triphosphate (ddNTP) which when incorporated onto the extended primer prevents the further extension of the primer. After the extension reaction has been terminated, the different termination products that are formed are separated and analyzed in order to determine the positioning of the different nucleosides.

Fluorescent DNA sequencing may generally be divided into two categories, "dye primer sequencing" and "dye terminator sequencing". In dye primer sequencing, a fluorescent dye is incorporated onto the primer being extended. Four separate extension/termination reactions are then run in parallel, each extension reaction containing a different dideoxynucleoside triphosphate (ddNTP) to terminate the extension reaction. After termination, the reaction products are separated by gel electrophoresis and analyzed. See, for example, Ansorge et al., *Nucleic Acids Res.* 15 4593–4602 (1987).

In one variation of dye primer sequencing, different primers are used in the four separate extension/termination reactions, each primer containing a different spectrally resolvable dye. After termination, the reaction products from the four extension/termination reactions are pooled, electrophoretically separated, and detected in a single lane. See, for example, Smith et al., *Nature* 321 674–679 (1986). Thus, in this variation of dye primer sequencing, by using primers containing a set of spectrally resolvable dyes, products from more than one extension/termination reactions can be simultaneously detected.

In dye terminator sequencing, a fluorescent dye is attached to each of the dideoxynucleoside triphosphates. An extension/termination reaction is then conducted where a primer is extended using deoxynucleoside triphosphates until the labeled dideoxynucleoside triphosphate is incorporated into the extended primer to prevent further extension of the primer. Once terminated, the reaction products for each dideoxynucleoside triphosphate are separated and detected. In one embodiment, separate extension/termination reactions are conducted for each of the four dideoxynucleoside triphosphates. In another embodiment, a single extension/termination reaction is conducted which contains the four dideoxynucleoside triphosphates, each labeled with a different, spectrally resolvable fluorescent dye.

Thus according to one aspect of the invention, a method is provided for conducting dye primer sequencing using one or more oligonucleotide reagents of the present invention. According to this method, a mixture of extended labeled primers are formed by hybridizing a nucleic acid sequence with a fluorescently labeled oligonucleotide primer in the presence of deoxynucleoside triphosphates, at least one dideoxynucleoside triphosphate and a DNA polymerase. The fluorescently labeled oligonucleotide primer includes an oligonucleotide sequence complementary to a portion of the nucleic acid sequence being sequenced, and an energy transfer fluorescent dye attached to the oligonucleotide.

According to the method, the DNA polymerase extends the primer with the deoxynucleoside triphosphates until a dideoxynucleoside triphosphate is incorporated which terminates extension of the primer. After termination, the mixture of extended primers are separated. The sequence of the nucleic acid sequence is then determined by fluorescently detecting the mixture of extended primers formed.

In a further embodiment of this method, four dye primer sequencing reactions are run, each primer sequencing reaction including a different fluorescently labeled oligonucleotide primer and a different dideoxynucleoside triphosphate (ddATP, ddCTP, ddGTP and ddTTP). After the four dye primer sequencing reactions are run, the resulting mixtures of extended primers may be pooled. The mixture of extended primers may then be separated, for example by electrophoresis and the fluorescent signal from each of the four different fluorescently labeled oligonucleotide primers detected in order to determine the sequence of the nucleic acid sequence.

According to a further aspect of the invention, a method is provided for conducting dye terminator sequencing using one or more dideoxynucleoside triphosphates labeled with an energy transfer dye of the present invention. According to this method, a mixture of extended primers are formed by hybridizing a nucleic acid sequence with an oligonucleotide primer in the presence of deoxynucleoside triphosphates, at least one fluorescently labeled dideoxynucleotide triphosphate and a DNA polymerase. The fluorescently labeled dideoxynucleotide triphosphate includes a dideoxynucleoside triphosphate labeled with an energy transfer fluorescent dye of the present invention.

According to this method, the DNA polymerase extends the primer with the deoxynucleoside triphosphates until a fluorescently labeled dideoxynucleoside triphosphate is incorporated into the extended primer. After termination, the mixture of extended primers are separated. The sequence of the nucleic acid sequence is then determined by detecting the fluorescently labeled dideoxynucleoside attached to the extended primer.

In a further embodiment of this method, the step of forming a mixture of extended primers includes hybridizing the nucleic acid sequence with four different fluorescently labeled dideoxynucleoside triphosphates, i.e., a fluorescently labeled dideoxycytosine triphosphate, a fluorescently labeled dideoxyadenosine triphosphate, a fluorescently labeled dideoxyguanosine triphosphate, and a fluorescently labeled dideoxythymidine triphosphate.

In each of the above-described fragment analysis methods, the labeled oligonucleotides are preferably separated by electrophoretic procedures, e.g. Gould and Matthews, cited above; Rickwood and Hames, Eds., *Gel Electrophoresis of Nucleic Acids: A Practical Approach*, (IRL Press Limited, London, 1981); or Osterman, *Methods of Protein and Nucleic Acid Research*, Vol. 1 Springer-Verlag, Berlin, 1984). Preferably the type of electrophoretic matrix is crosslinked or uncrosslinked polyacrylamide having a concentration (weight to volume) of between about 2–20 weight percent. More preferably, the polyacrylamide concentration is between about 4–8 percent. Preferably in the context of DNA sequencing in particular, the electrophoresis matrix includes a strand separating, or denaturing, agent, e.g., urea, formamide, and the like. Detailed procedures for constructing such matrices are given by Maniatis et al., "Fractionation of Low Molecular Weight DNA and RNA in Polyacrylamide Gels Containing 98% Formamide or 7 M Urea," in *Methods in Enzymology*, 65 299–305 (1980); Maniatis et al., "Chain Length Determination of Small Double- and Single-Stranded DNA Molecules by Polyacrylamide Gel Electrophoresis," *Biochemistry*, 14 3787–3794 (1975); Maniatis et al., *Molecular Cloning: A Laboratory Manual* (Cold Spring Harbor Laboratory, New York, 1982), pgs. 179–185; and *ABI PRISM™ 377 DNA Sequencer User's Manual*, Rev. A, January 1995, Chapter 2 (p/n 903433, The Perkin-Elmer Corporation, Foster City, Calif.), each of which are incorporated by reference. The optimal polymer concentration, pH, temperature, concentration of denaturing agent, etc. employed in a particular separation depends on many factors, including the size range of the nucleic acids to be separated, their base compositions, whether they are single stranded or double stranded, and the nature of the classes for which information is sought by electrophoresis. Accordingly application of the invention may require standard preliminary testing to optimize conditions for particular separations. By way of example, oligonucleotides having sizes in the range of between about 20–300 bases have been separated and detected in accordance with the invention in the following matrix: 6 percent polyacrylamide made from 19 parts to 1 part acrylamide to bisacrylamide, formed in a Tris-borate EDTA buffer at pH 8.3.

After electrophoretic separation, the dye-oligonucleotide conjugates are detected by measuring the fluorescence emission from the dye labeled polynucleotides. To perform such detection, the labeled polynucleotides are illuminated by standard means, e.g. high intensity mercury vapor lamps, lasers, or the like. Preferably the illumination means is a laser having an illumination beam at a wavelength between 488 and 550 nm. More preferably, the dye-polynucleotides are illuminated by laser light generated by an argon ion laser, particularly the 488 and 514 nm emission lines of an argon ion laser, or an the 532 emission line of a neodymium solid-state YAG laser. Several argon ion lasers are available commercially which lase simultaneously at these lines, e.g. Cyonics, Ltd. (Sunnyvale, Calif.) Model 2001, or the like. The fluorescence is then detected by a light-sensitive detector, e.g., a photomultiplier tube, a charged coupled device, or the like.

IV. Kits Incorporating The Energy Transfer Dyes

The present invention also relates to kits having combinations of energy transfer fluorescent dyes and/or reagents. In one embodiment, the kit includes at least two spectrally resolvable energy transfer dyes according to the present invention. In this kit, the energy transfer dyes preferably include the same donor dye so that a single light source is needed to excite the dyes.

In another embodiment, the kit includes dideoxycytosine triphosphate, dideoxyadenosine triphosphate, dideoxyguanosine triphosphate, and dideoxythymidine triphosphate, each dideoxynucleotide triphosphate labeled with an energy transfer dye according to the present invention. In one embodiment, each energy transfer dye is spectrally resolvable from the other energy transfer dyes attached to the other dideoxynucleotide triphosphates. In this kit, the energy transfer dyes preferably include the same first xanthene dye.

In yet another embodiment, the kit includes at least two oligonucleotides, each oligonucleotide including an energy transfer dye according to the present invention. In one embodiment, each oligonucleotide contains an energy transfer dye which is spectrally resolvable from the energy transfer dyes attached to the other oligonucleotides. In another embodiment, the kit includes at least four oligonucleotides which each contain a spectrally resolvable energy transfer dye.

The energy transfer fluorescent dyes and their use in DNA sequencing is illustrated by the following examples. Further objectives and advantages other than those set forth above will become apparent from the examples.

EXAMPLES

1. Synthesis of 5TMR-B-CF

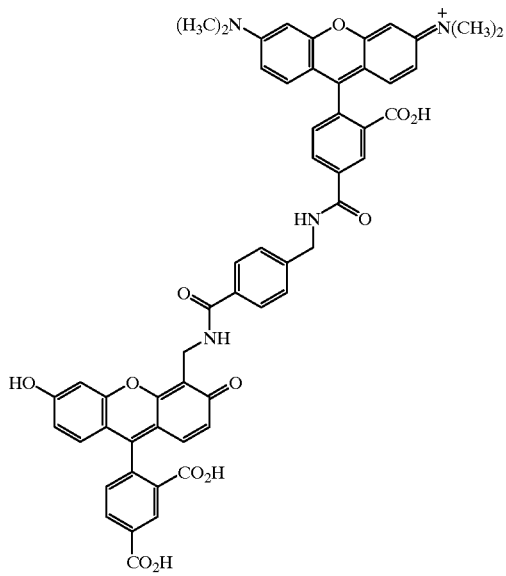

5TMR-B-CF was synthesized from 5-TMR NHS and 4'-aminomethyl-5-carboxyfluorescein according to the reaction sequences described in Examples 1A–C. 5TMR-B-CF was then converted to 5TMR-B-CF-NHS according to the reaction sequence described in 1D so that the dye could be coupled to a nucleoside, nucleotide or oligonucleotide primer.

A. Synthesis of 5-TMR-B

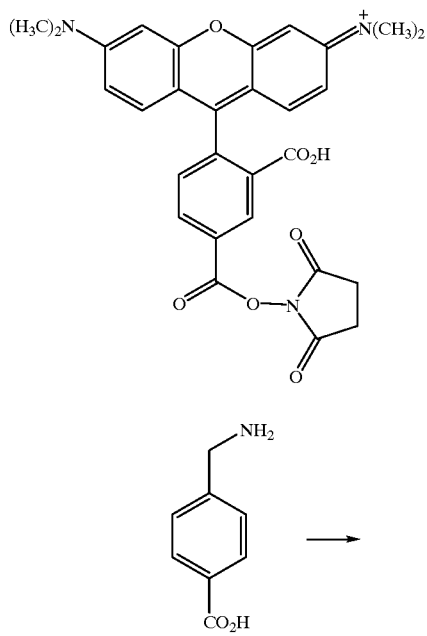

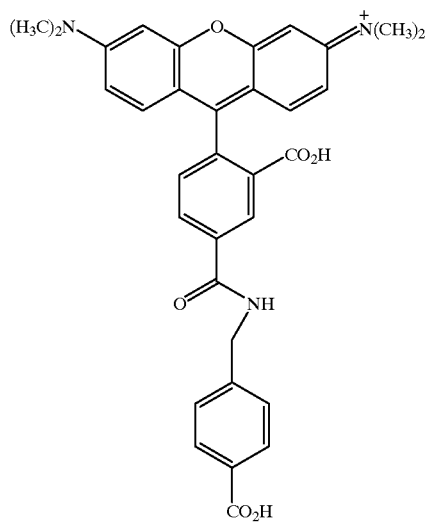

A mixture of 4-aminomethylbenzoic acid (3 mg, 19 μmol), 5-TMR NHS (5 mg, 9 μmol) and triethylamine (20 μL) was suspended in dimethylformamide (DMF, 200 μL) in a 1.5-mL eppendorf tube. The mixture was heated to 60° C. for 10 minutes. Reaction progress was monitored by thin layer chromatography (TLC) on silica gel with elution with a 400/30/10 mixture of dichloromethane, methanol and acetic acid. The insoluble 4-aminomethylbenzoic acid was separated by centrifugation and the DMF solution was decanted into 5% HCl (1 mL). The insoluble 5TMR-B was separated by centrifugation, washed with 5% HCl (2×1 mL) and dried in a vacuum centrifuge. The product was dissolved in DMF (200 μL) and used to prepare 5TMR-B-NHS.

B. Synthesis of 5-TMR-B-NHS

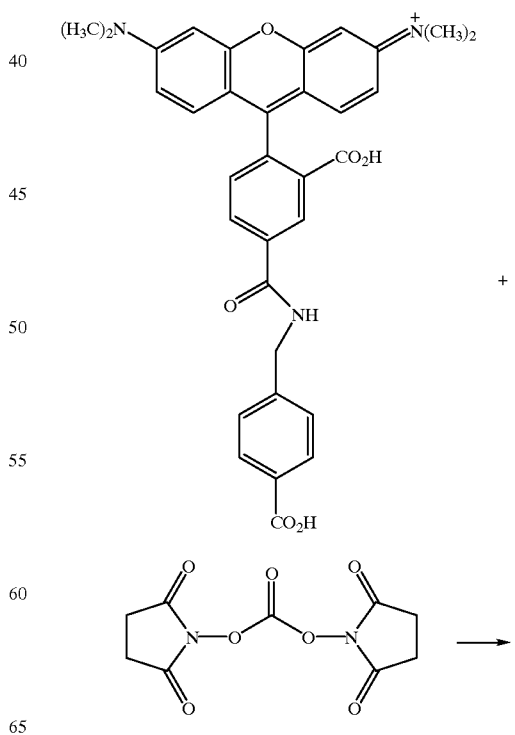

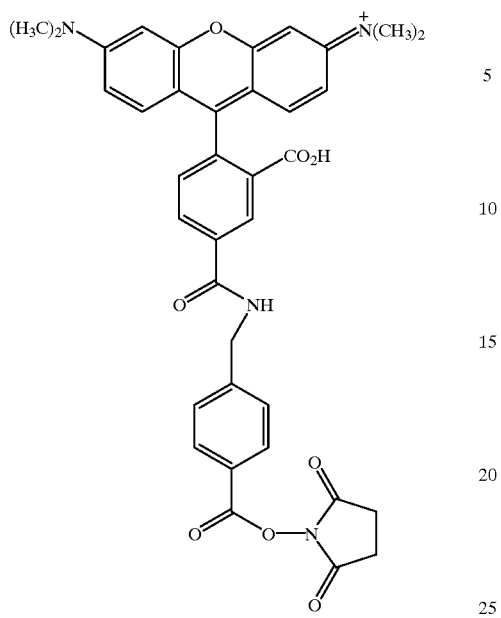

A solution of 5TMR-B in DMF (125 μL), diisopropylethylamine (10 μL) and disuccinimidylcarbonate (10 mg) was combined in a 1.5-mL eppendorf tube and heated to 60° C. The reaction progress was monitored by TLC on silica gel with elution with a 600/60/16 mixture of dichloromethane, methanol and acetic acid. After five minutes, the reaction appeared to be complete. The solution was diluted into methylene chloride (3 mL) and washed with 250 mM carbonate/bicarbonate buffer (pH 9, 4×1 mL), dried ($Na_2SO_4$) and concentrated to dryness on a vacuum centrifuge. The solid was dissolved in DMF (100 μL). The yield was determined by diluting an aliquot into pH 9 buffer and measuring the absorbance at 552 nm. Using an extinction coefficient of 50,000 $cm^{-1}$ $M^{-1}$, the concentration of 5TMR-B-NHS was 4.8 mM. Yield from 5TMR NHS was 8%.

C. Synthesis of 5TMR-B-CF

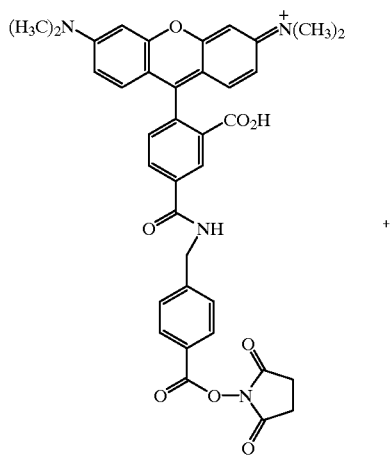

+

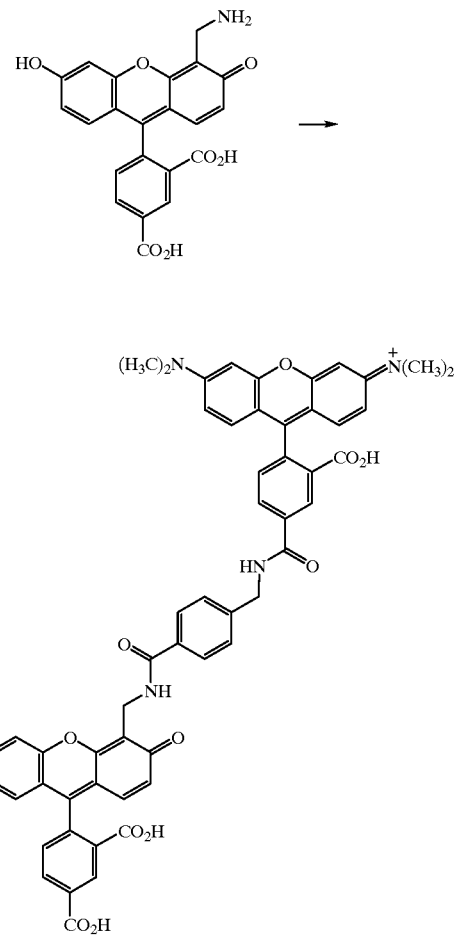

A solution of 5TMR-B-NHS (1 μmol in 250 μL DMF) was combined with a solution of 4'-aminomethyl-5-carboxyfluorescein (CF, 2.2 μmol in 100 μL DMSO) and triethylamine (20 μL) in a 1.5-mL eppendorf tube. The reaction was monitored by HPLC using a C8 reverse-phase column with a gradient elution of 15% to 35% acetonitrile vs. 0.1M triethylammonium acetate. HPLC analysis indicated the 5TMR-B-NHS was consumed, leaving the excess, unreacted CF. The reaction was diluted with 5% HCl (1 mL) and the product separated by centrifugation, leaving the unreacted CF in the aqueous phase. The solid was washed with 5% HCl (4×1 mL), dried in a vacuum centrifuge and taken up in DMF (300 μL). The yield was quantitative.

D. Synthesis of 5-TMR-B-CF-NHS

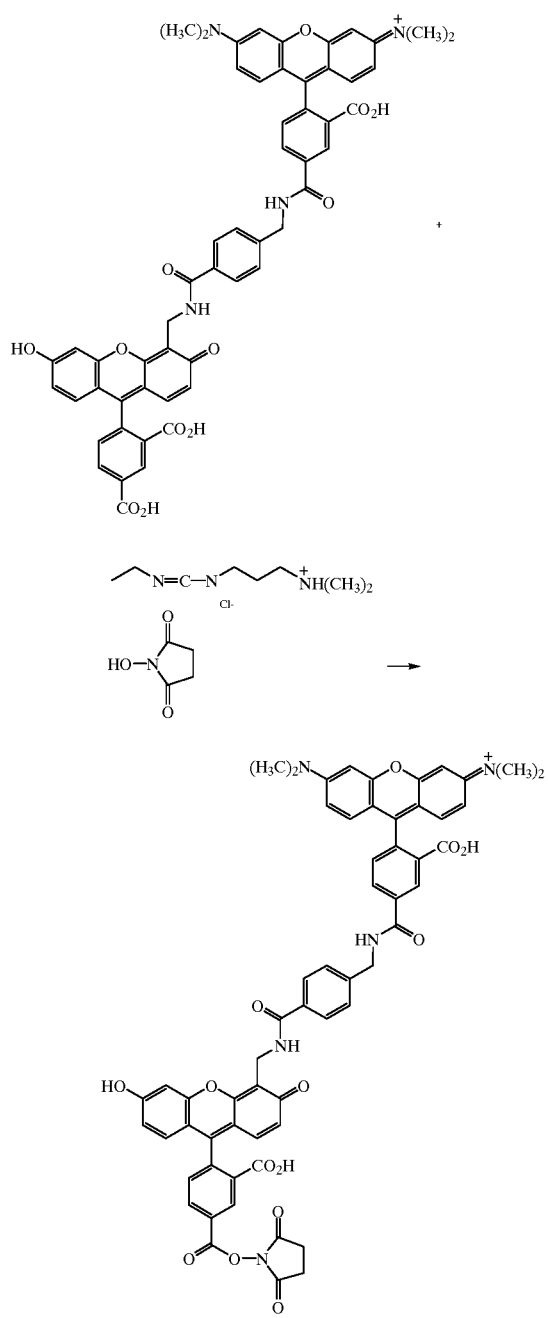

A solution of 5TMR-B-CF (0.6 μmol in 100 μL DMF), 1-(3-dimethylaminopropyl)-3-ethylcarbodiimide hydrochloride (DEC, 2 mg) and N-hydroxysuccinimide (4 mg) were combined in a 1.5-mL eppendorf tube. The mixture was sonicated briefly and heated to 60° C. The reaction was monitored by TLC on silica gel with elution with a 600/60/16 mixture of dichloromethane, methanol and acetic acid. The reaction was complete in 30 minutes and diluted with 5% HCl. The product was separated by centrifugation and dried in a vacuum centrifuge. The activated dye was dissolved in DMF (20 μL).

2. Synthesis of 5ROX-CF

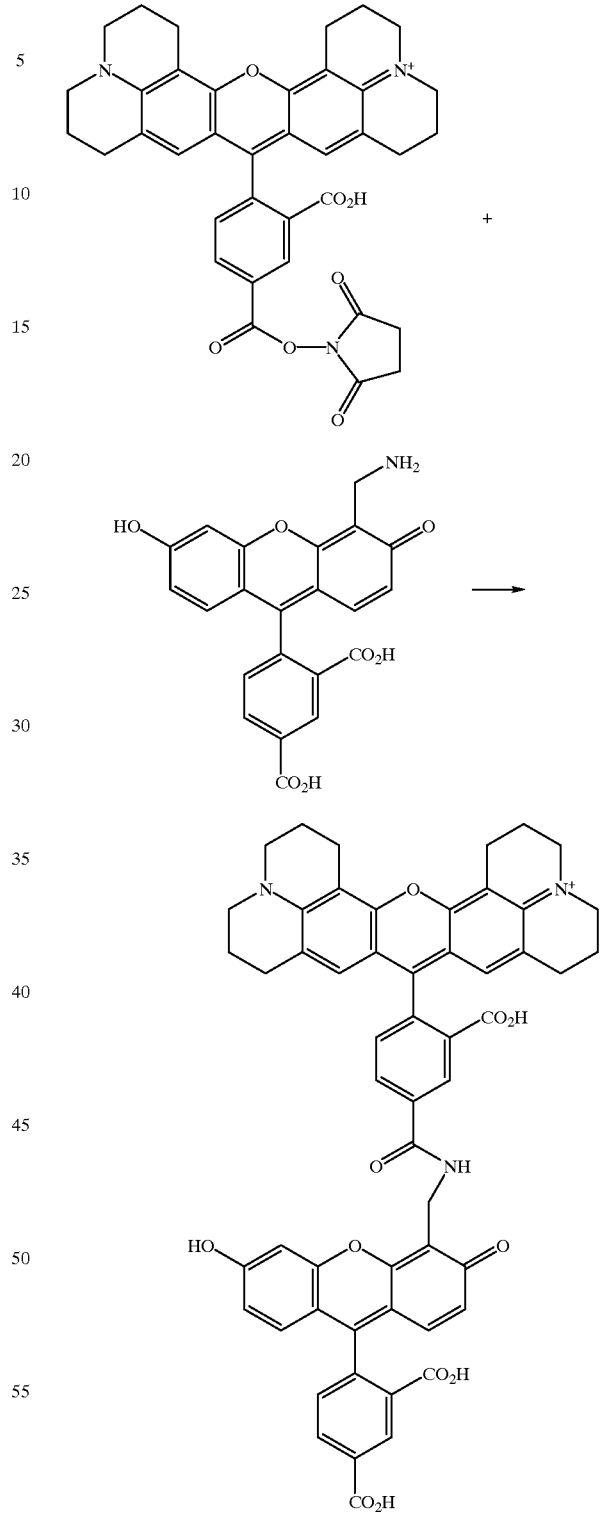

A solution of 5ROX NHS (2 μmol in 100 μL DMSO) was mixed with CF (2 μmol in 100 μL DMSO) and triethylamine (10 μL). The reaction was followed by HPLC on a C8 reverse phase column using a gradient elution of 20% to 40% acetonitrile vs. 0.1M TEM. The reaction was diluted into 5% HCl (1 mL) and the product collected by centrifugation, washed with 5% HCl (1×1 mL) and dried in a vacuum centrifuge. The product was taken up in DMF (200 μL).

3. Synthesis of Cy5-CF was diluted into 5% HCl (1 mL) and the product collected by centrifugation, washed with 5% HCl (1×1 mL) and dried in a vacuum centrifuge. The product was taken up in DMF (100 μL).

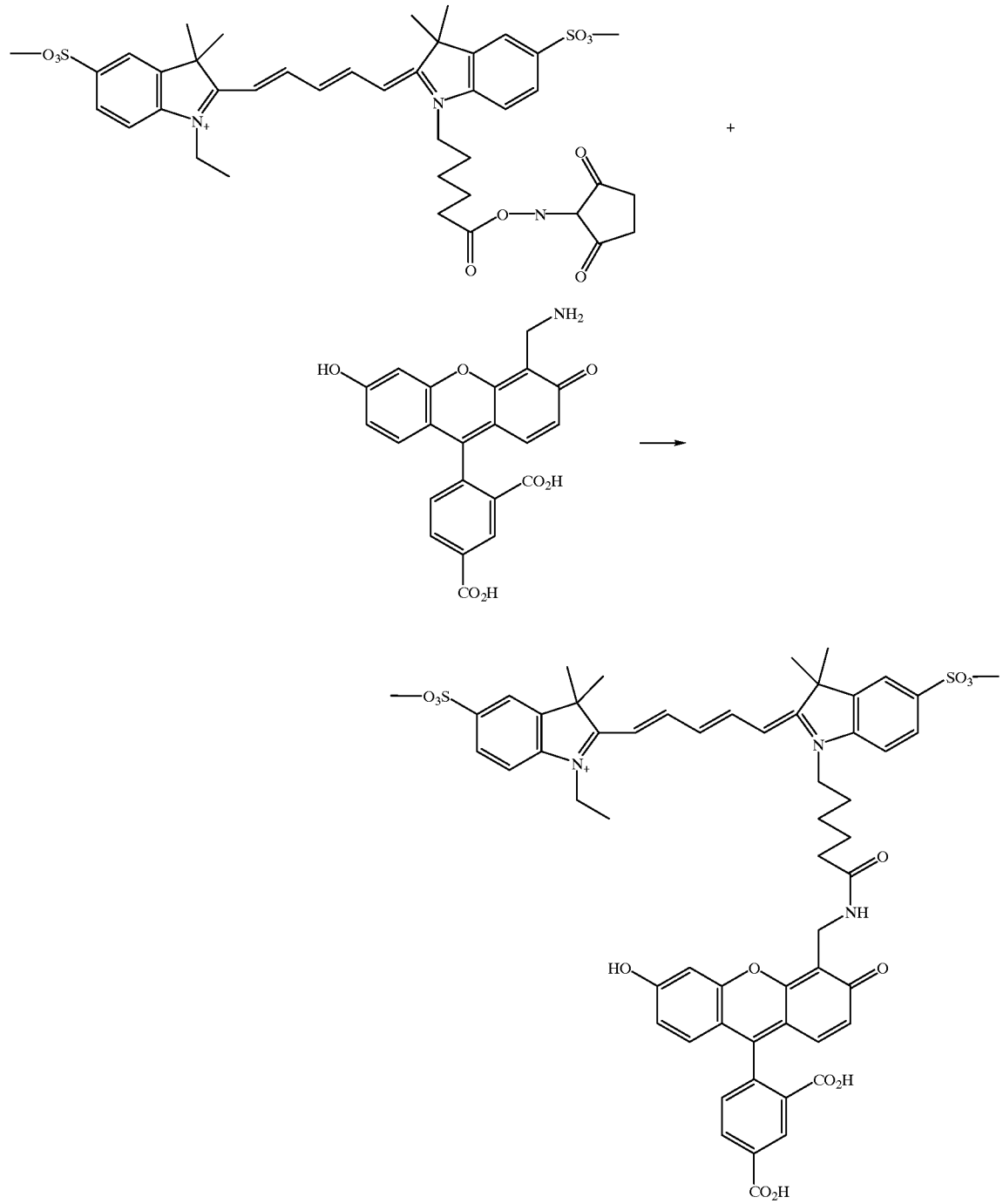

A solution of CF (0.4 μmol in 20 μL CMSO) and triethylamine (2 μL) was added to monoCy5 NHS (approximately 0.3 μmol). The reaction was followed by HPLC on a C8 reverse phase column using a gradient elution of 10% to 30% acetonitrile vs. 0.1M TEAA. The reaction 4. Comparison Of Fluorescence Strength of Energy Transfer Dyes The following example compares the fluorescence emission strength of a series of energy transfer dyes according to the present invention. Dye solutions of 5TMR, 6TMR-CF, 5TMRgly-CF, 5TMR-CF, 5TMR-B-CF, 5TMRgly-5AMF, 5TMR-5AMF and 5TMR-lys-5FAM were measured in 1xTBE/8M urea. Each dye solution had an optical density of 0.1 at 560 nm and was excited at 488 nm.
TABLE 7
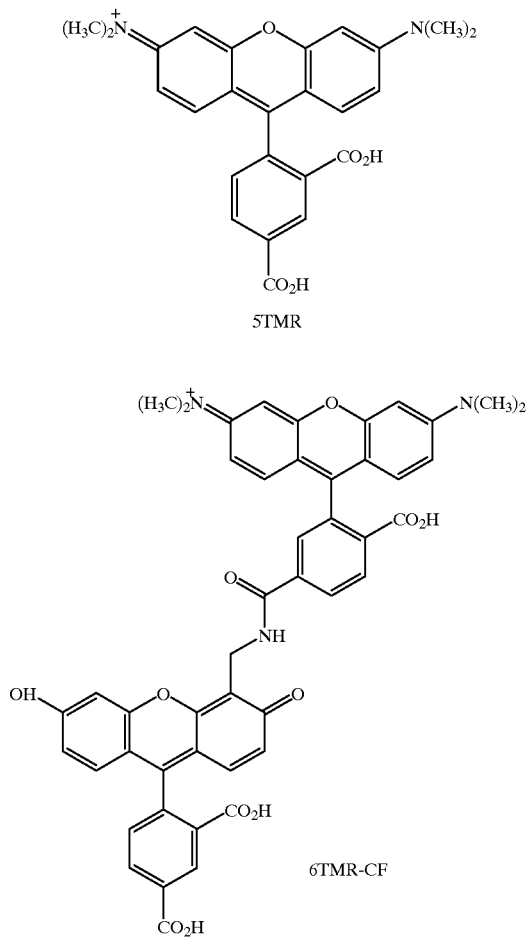
TABLE 7-continued
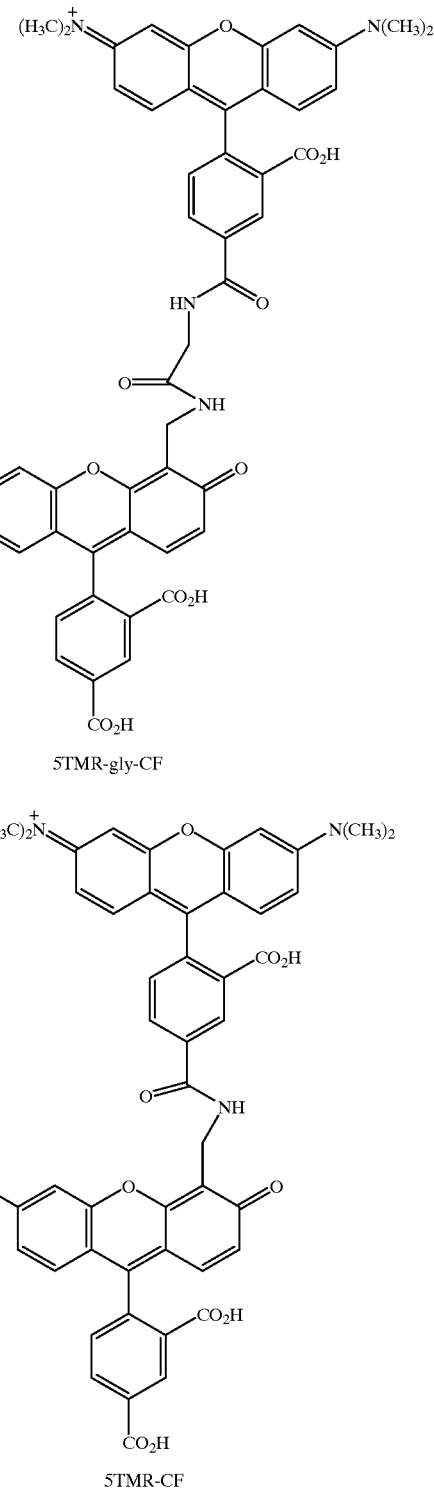

TABLE 7-continued
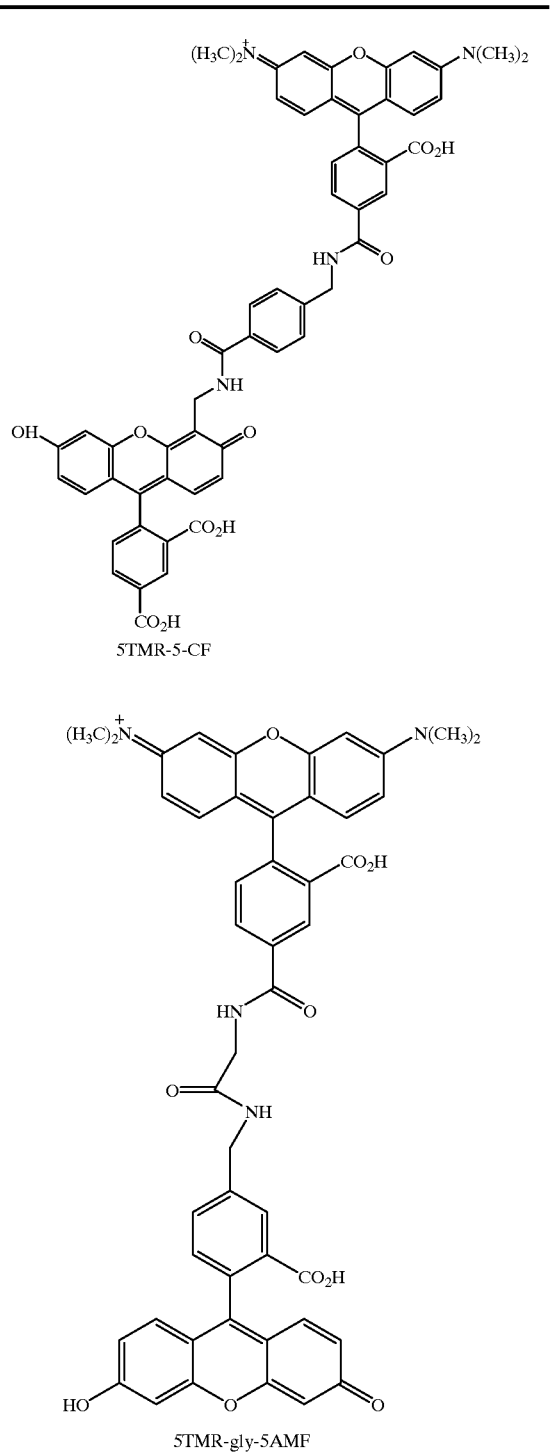
5TMR-5-CF
5TMR-gly-5AMF
TABLE 7-continued
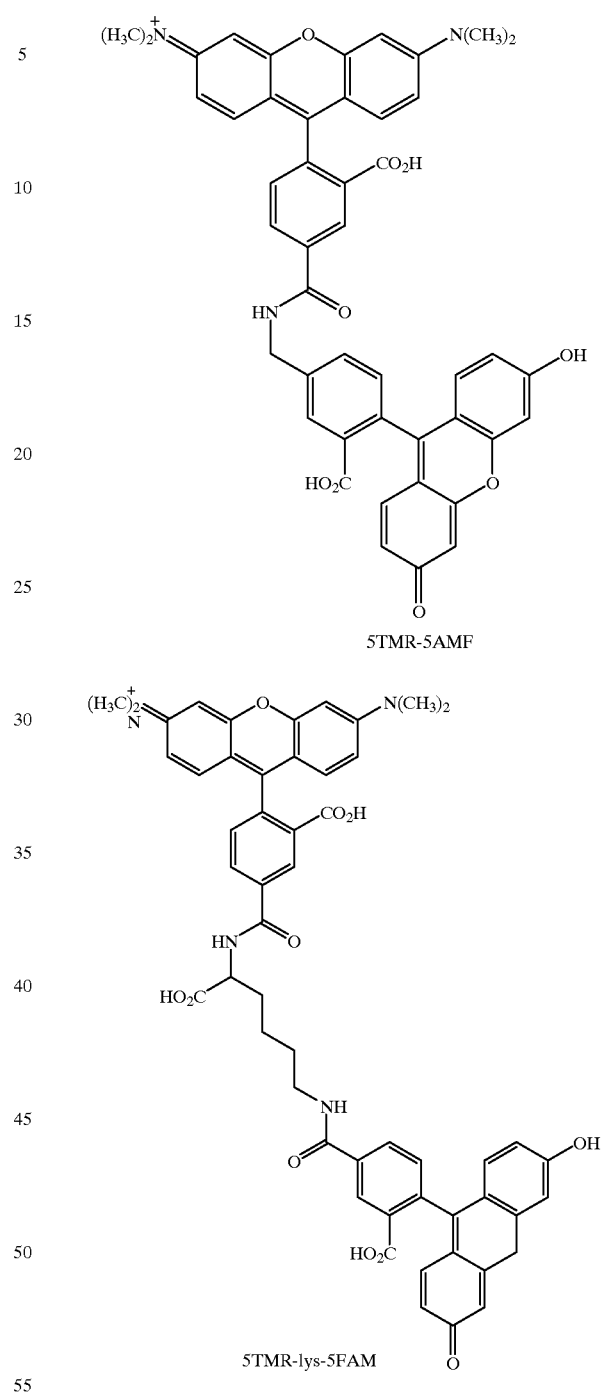
5TMR-5AMF
5TMR-lys-5FAM
The structures of each of these dyes is illustrated in Table 7. FIG. 2 provides a bar graph of the relative fluorescence of each of these dyes.

As can be seen from FIG. 2, energy transfer dyes where the linker is attached to the acceptor at the 5 ring position (5TMR-CF and 5-TMR-B-CF were found to exhibit significantly stronger fluorescence than the acceptor dye itself or when the acceptor dye is linked at the 6 ring position (6TMR-CF). As also can be seen from FIG. 2, energy transfer dyes where the linker has the formula $R_1XC(O)R_2$ where $R_2$ is benzene (5TMR-B-CF) were found to have significantly enhanced fluorescence as compared to the dye where the linker has the formula —$CH_2NHCO$—(5TMR-CF) or —$CH_2NHCOCH_2NHCO$— (5TMR-gly-5AMF).

As can also be seen from FIG. 2, energy transfer dyes where the linker is attached to both the donor and acceptor at the 5 ring position (5TMR-5AMF and 5TMR-gly-5AMF) were found to have significant fluorescence. Interestingly, the use of a lysine linker was found not to result in appreciable energy transfer between the donor and acceptor.

5. Dye Primer Sequencing Using Energy Transfer Dye

Figure 7:
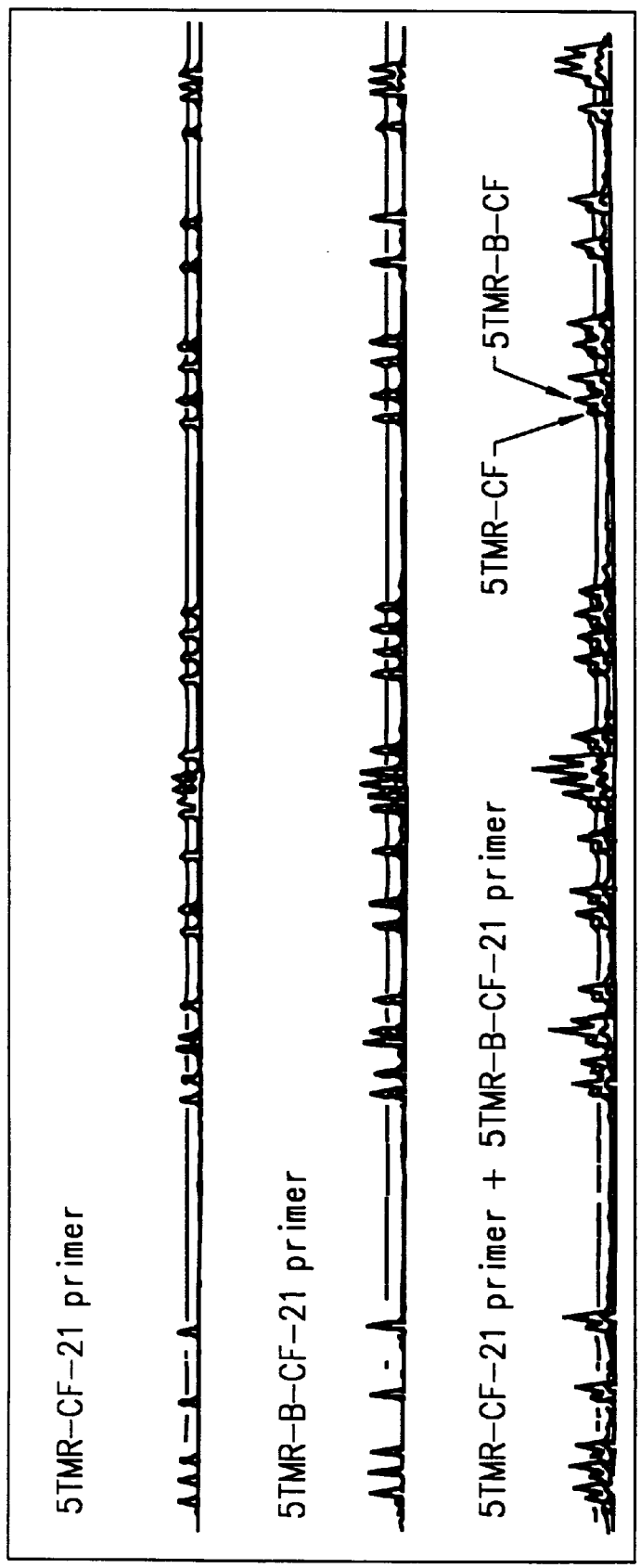
FIG. 7 is a plot of a mixture of labeled oligonucleotides generated during dye primer sequencing using 5TMR-CF and 5TMR-BCF labeled primers.

In this example, dye primer sequencing was performed on M13 (SEQ. ID. NO.: 1) in order to compare the relative brightness of 5TMR-CF and 5TMR-B-CF labeled oligonucelotides. In this example, dye primer sequencing was performed according to the *ABI PRISM™ 377 DNA Sequencer User's Manual, Rev. B,* January 1995, Chapter 2 (p/n 402114, The Perkin-Elmer Corporation, Foster City, Calif.). 5TMR-CF and 5TMR-B-CF were each attached to the 5' end of M13–21 primer (SEQ. ID. NO.:2). Equimolar solutions of each primer were mixed with the M13 (SEQ. ID. NO.: 1) and sequenced with a single dideoxy nucleotide mixture (ddA/dNTP) and Taq FS. A plot of the resulting mixture of oligonucleotides that were detected using 5TMR-CF and 5TMR-B-CF labeled primers is presented in FIG. 7. As can be seen from FIG. 7, oligonucleotides labeled with 5TMR-B-CF are brighter than oligonucleotides labeled with 5TMR-CF. As can also be seen from FIG. 7, the mobility of oligonucleotides labeled with 5TMR-B-CF are about one nucleotide slower than the oligonucleotides labeled with 5TMR-CF.

6. Dye Primer Sequencing Using Four Dyes

Figure 8:
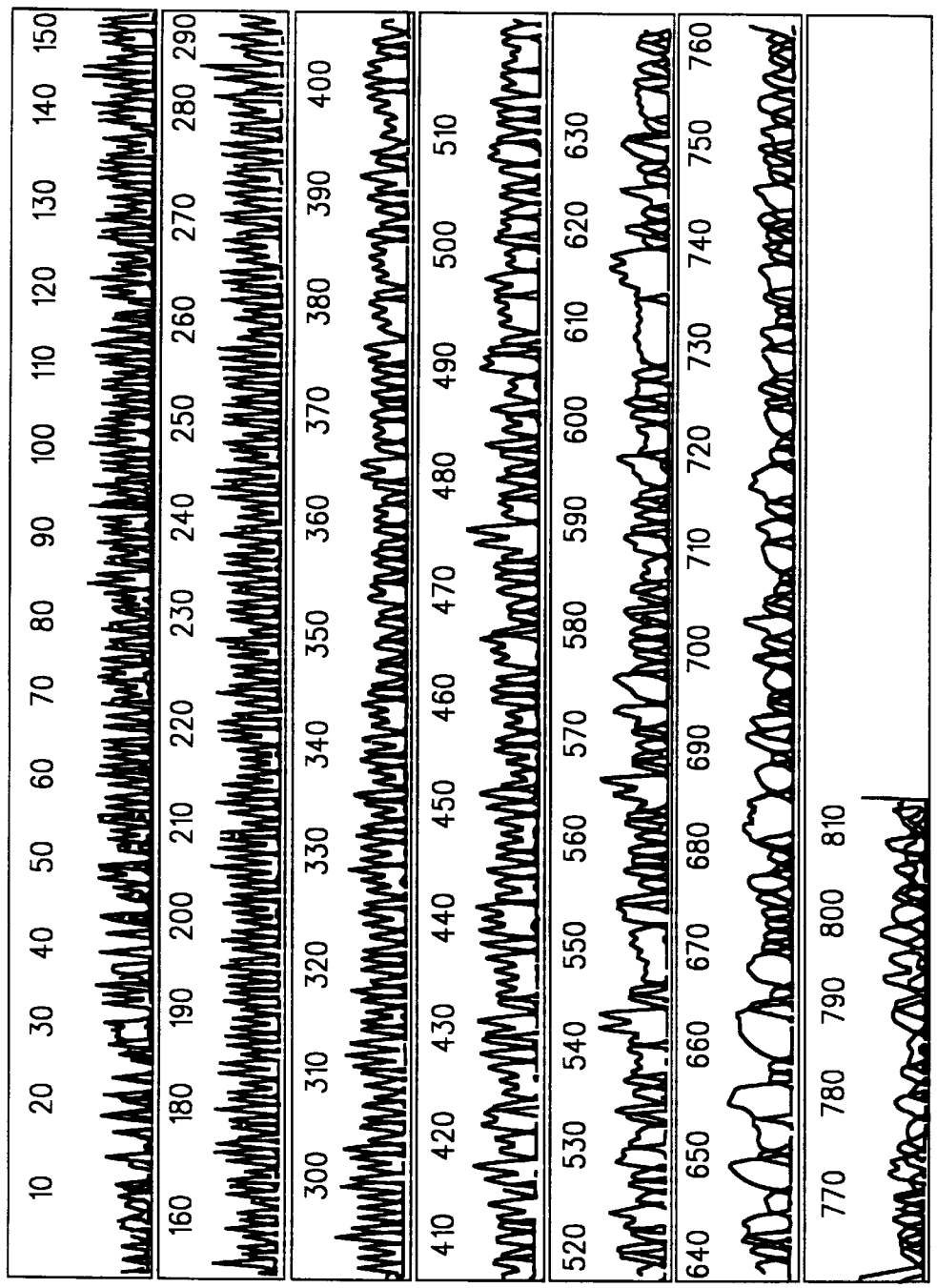
FIG. 8 is a four color plot of dye primer sequencing using a four dye set including 3-carboxy-R110, 5-carboxy-R6G, 5TMR-CF and 5TMR-B-CF.

Dye primer sequencing was performed on the M13 (SEQ. ID. NO.: 1) using a set of four dyes attached to the M13–21 primer (SEQ. ID. NO. 2) as described in Example 5. FIG. 8 is a four color plot of the dye labeled oligonucleotides produced from the sequencing. The peak for cytosine corresponds to the fluorescence of 5-carboxy-R110. The peak for adenosine corresponds to the fluorescence of 5-carboxy-R6G. The peak for guanosine corresponds to the fluorescence of TMR-B-CF. The peak for thymidine corresponds to the fluorescence of ROX-CF.

As can be seen from FIG. 8, each of the dye labeled oligonucleotides exhibit significant fluorescence intensity. In addition, the different dye labeled oligonucleotides exhibit sufficiently similar mobility so that good resolution of the series of peaks is achieved.

7. Synthesis of 6-CFB-DTMR-2-NHS

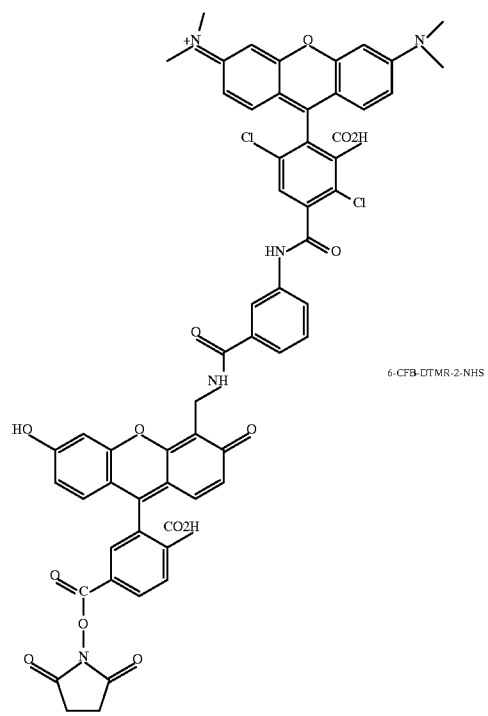

6-CFB-DTMR-2 was synthesized from DTMR-2 and 6-CFB according to the reaction sequences described in Examples 1A–B. 6-CFB-DTMR-2 was then converted to 6-CFB-DTMR-2-NHS according to the reaction sequence described in 1C so that the dye could be coupled to a nucleoside, nucleotide or oligonucleotide primer.

A. Synthesis of DTMR-2-NHS

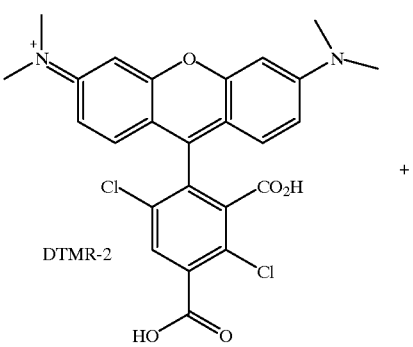

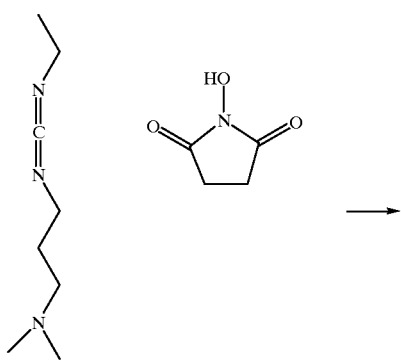

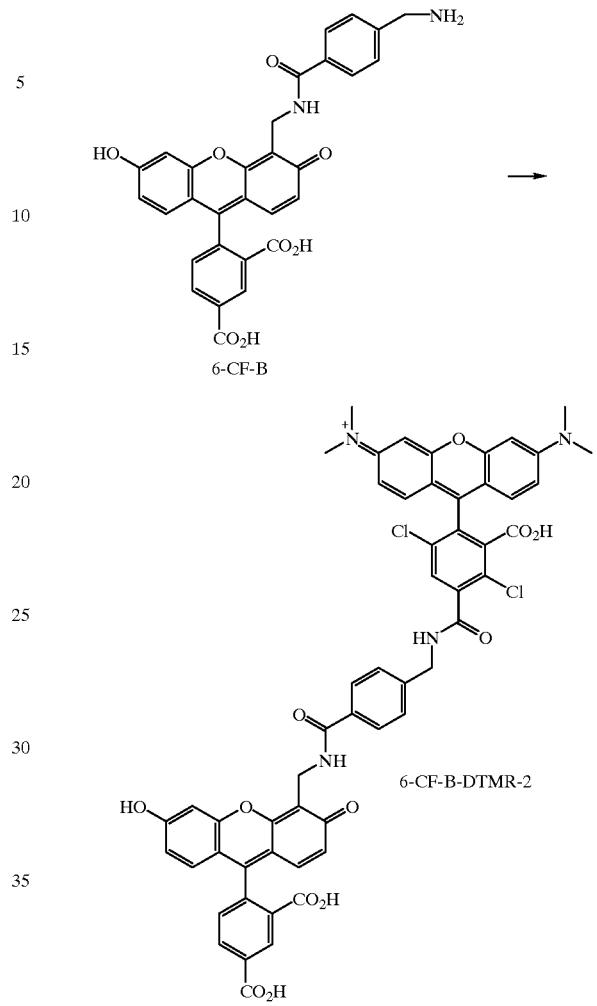

A solution of DTMR-2 in DMF, N-hydroxysuccinimide and 1-(3-dimethylaminopropyl)-3-ethylcarbodiimide hydrochloride were combined in an eppendorf tube and heated to 60° C. The reaction progress was monitored by TLC on silica gel. After the reaction appeared to be complete, the solution was diluted into methylene chloride and washed with 250 mM carbonate/bicarbonate buffer (pH 9, 4×1 mL), and then with an HCl solution (5%, 1×1 mL), dried ($Na_2SO_4$) and concentrated to dryness on a vacuum centrifuge.

B. Synthesis of 6-CF-B-DTMR-2

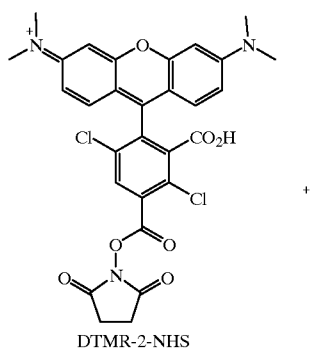

A solution of 6-CFB in dimethylsulfoxide (100 μL, 11 mM) was combined with a solution of DTMR-2 succidimidyl ester in dimethylformamide (100 μL, 22 mM) and triethylamine (20 μL). The reaction was added to a solution of hydrochloric acid (5%, 1 mL) and the solid separated by centrifugation. The red solid was dissolved in carbonate/bicarbonate buffer (250 mM, pH 9, 100 μL) and reprecipitated with dilute HCl. The solid was dried in a vacuum centrifuge and dissolved in dimethylformamide (200 μL). The concentration of the dye solution was determined by diluting an aliquot into 40% acetonitrile/0.1M triethylammonium acetate buffer (pH 7). Assuming an extinction coefficient of 80,000 $cm^{-1}m^{-1}$ for fluorescein, the 6-CF-B-DTMR-2 solution was found to be 4 mM (70% yield).

C. Synthesis of 6-CF-B-DTMR-NHS

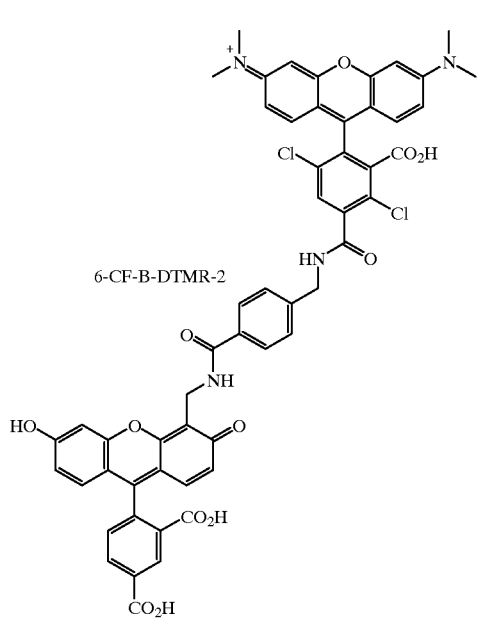

6-CF-B-DTMR-2

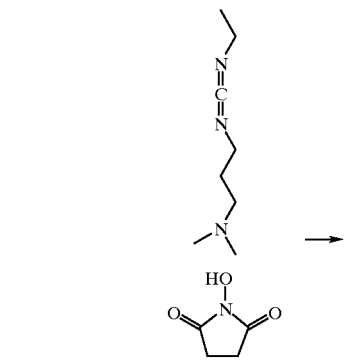

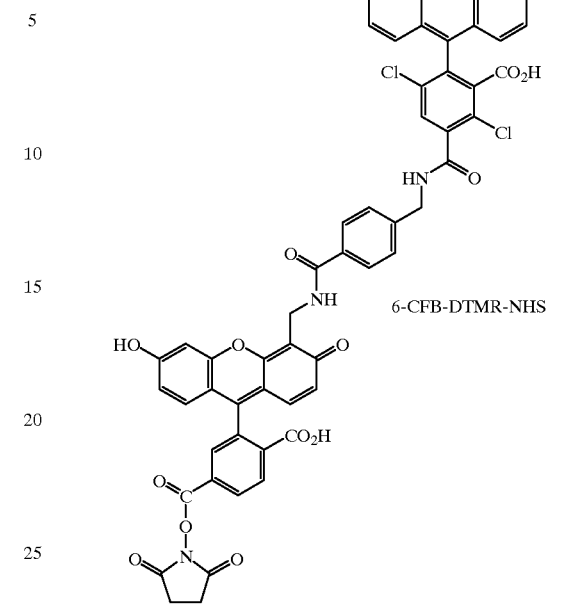

6-CFB-DTMR-NHS

A solution of 6-CF-B-DTMR-2 in dimethylformamide (200 μL, 4 mM) was added N-hydroxysuccinimide (10 mg) and 1-(3-dimethylaminopropyl)-3-ethylcarbodiimide hydrochloride (5 μg). Additional N-hydroxysuccinimide (10 mg) was added. The reaction progress was monitored by thin-layer chromatography on silica gel with elution with dichloromethane: methanol: acetic acid in a 600:60:16 mixture. When the reaction was complete, dilute HCl (5%, 1 mL) was added and the product separated by centrifugation. The solid was dried in a vacuum centrifuge and dissolved in dimethylformamide (100 μL). The concentration of the dye solution was determined by diluting an aliquot into 40% acetonitrile/ 0.1M triethylammonium acetate buffer (pH 7). Assuming an extinction coefficient of 80,000 cm$^{-1}$m$^{-1}$ for fluorescein, the 6-CF-B-DTMR-NHS solution was found to be 5.4 mM (68% yield).

8. Comparison Of Fluorescence Strength of Dyes

Figure 9A:
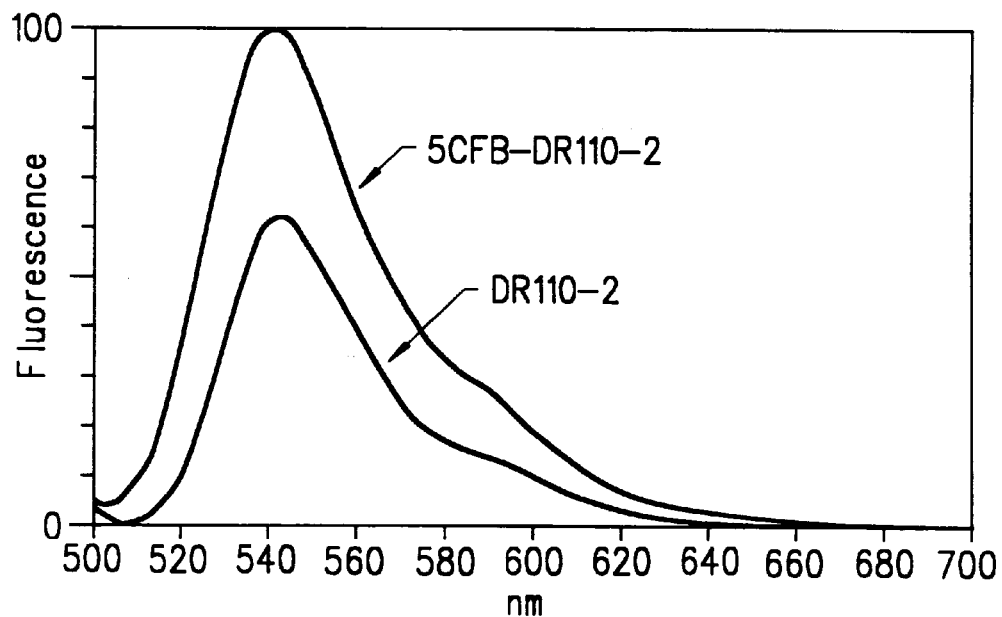
FIGS. 9A–D compare the fluorescence emission strength of a series of energy transfer dyes of the present invention to the corresponding acceptor dye alone.
Figure 9B:
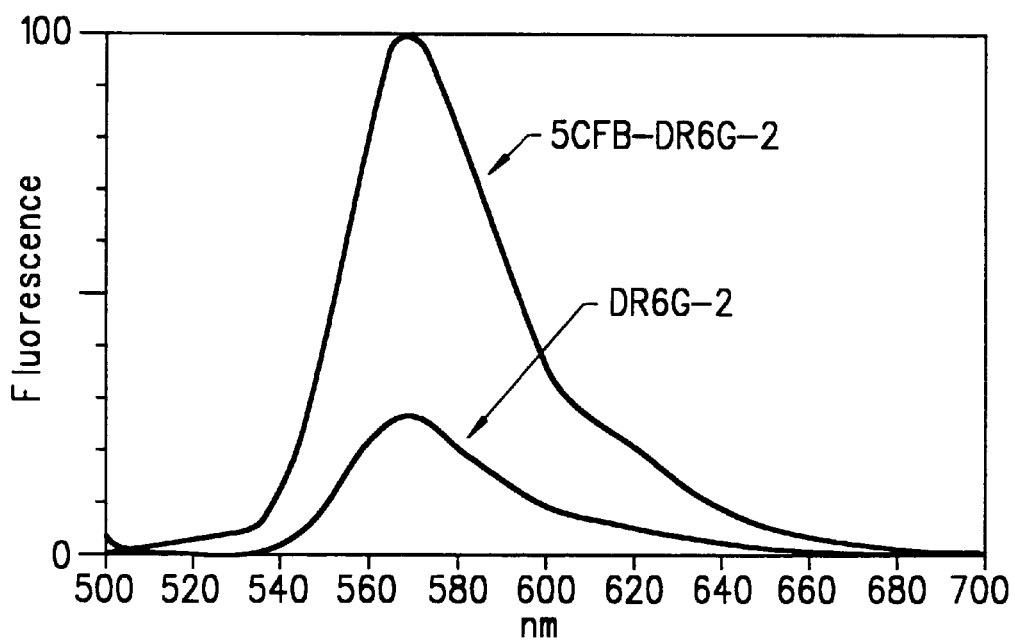
Figure 9C:
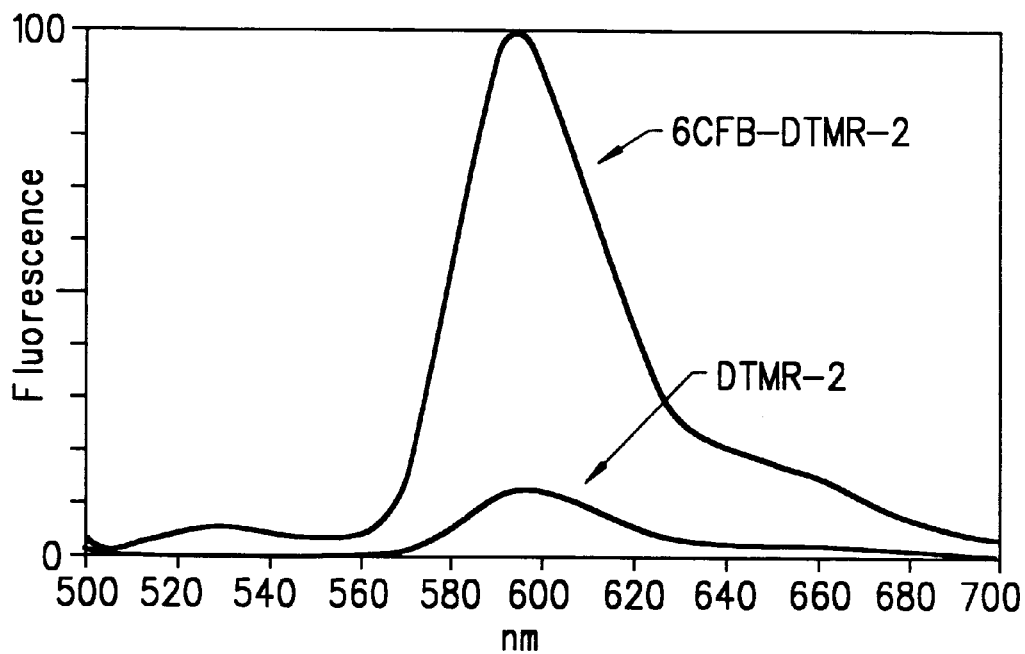
Figure 9D:
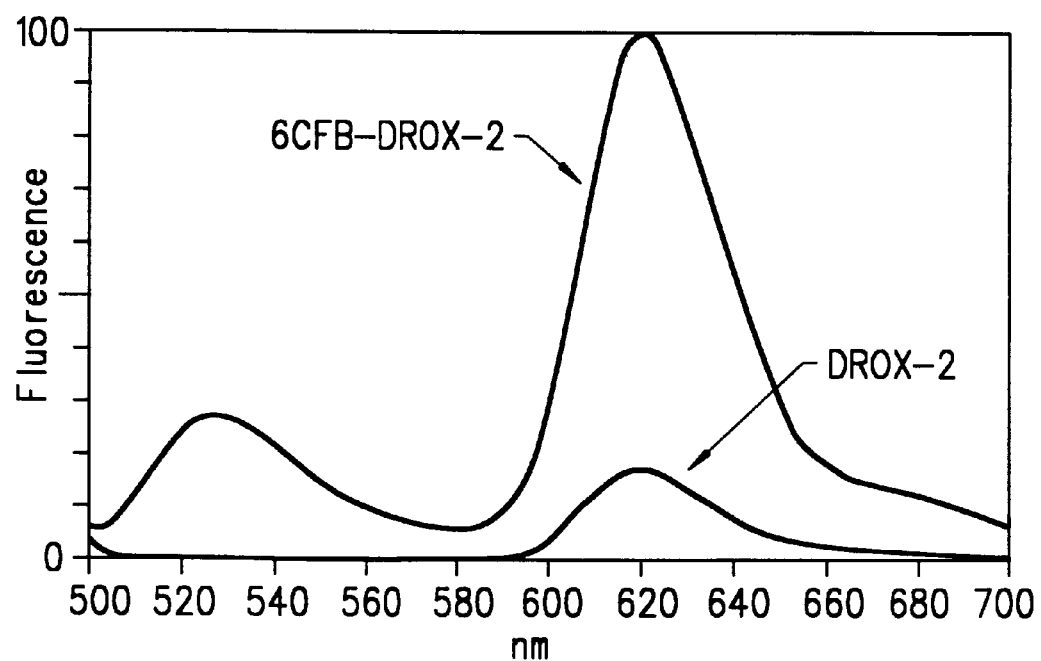

The following example compares the fluorescence emission strength of a series of energy transfer dyes according to the present invention to the corresponding acceptor dye. According to this example, each dye was attached to a 21 primer sequence (5'-TGTAAAACGACGGCCAGT) (SEQ. ID. NO.: 1) with an aminohexyl linkage at the 5' end. The oligonucleotides were quantitated based on the absorbance at 260 nm, assuming an extinction coefficient of 180,000 cm$^{-1}$ M$^{-1}$. Spectra were obtained at a primer concentration of 0.4 μM in 8M urea, 1X Tris/Borate/EDTA (TBE) buffer with 488 nm excitation. FIG. 9A provides the overlaid spectra of 5-CFB-DR110-2 and DR110-2. FIG. 9B provides the overlaid spectra of 5-CFB-DR6G-2 and DR6G-2. FIG. 9C provides the overlaid spectra of 6-CFB-DTMR-2 and DTMR-2. FIG. 9D provides the overlaid spectra of 6CFB-DROX-2 and DROX-2.

The structures of each of these dyes is illustrated in Table 1. As can be seen from FIGS. 9A–D, energy transfer dyes were found to exhibit significantly stronger fluorescence than the acceptor dye itself.

Figure 10:
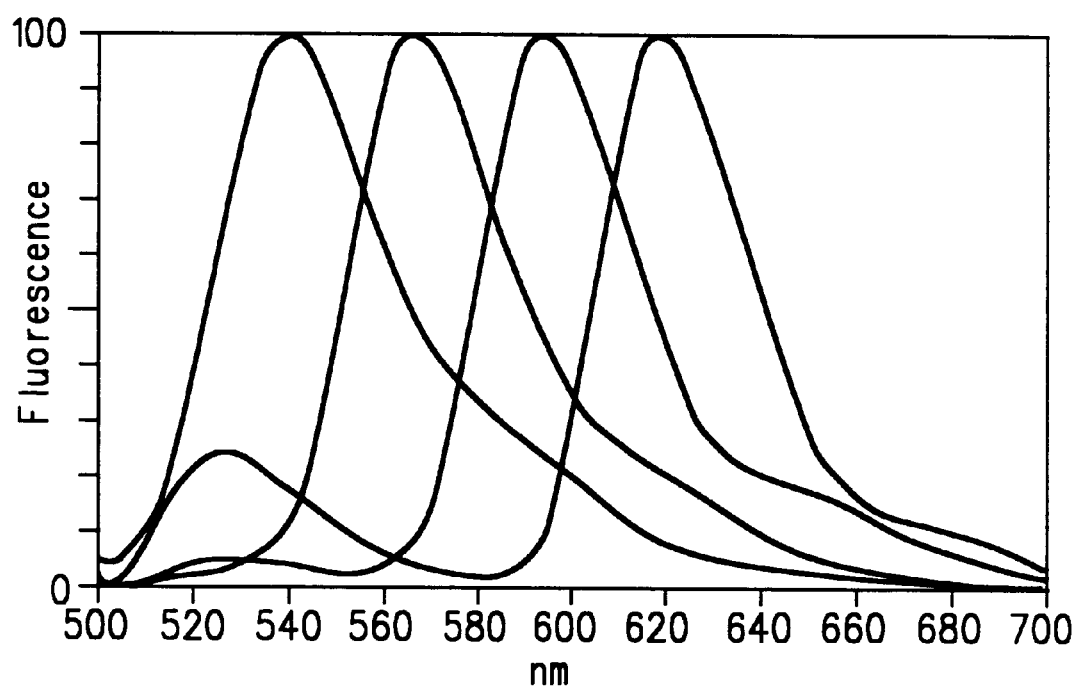
FIG. 10 illustrates a set of four dyes (5-CFB-DR110-2, 5-CFBDR6G-2, 6-CFB-DTMR-2, and 6-CFB-DROX-2) which are spectrally resolvable from each other.

FIG. 10 shows the normalized fluorescence emission spectra of four dye-labeled oligonucleotides. Spectra were obtained at a primer concentration of 0.4 μM in 8M urea, 1X Tris/Borate/EDTA (TBE) buffer with 488 nm excitation. The dyes shown in FIG. 10 include 5-CFB-DR110-2, 5-CFB-DR6G-2, 6-CFB-DTMR-2, and 6-CFB-DROX-2. As can be seen from FIG. 10, all four energy transfer dyes are well resolved relative to each other.

9. Dye Primer Sequencing Using Energy Transfer Dye

Figure 11:
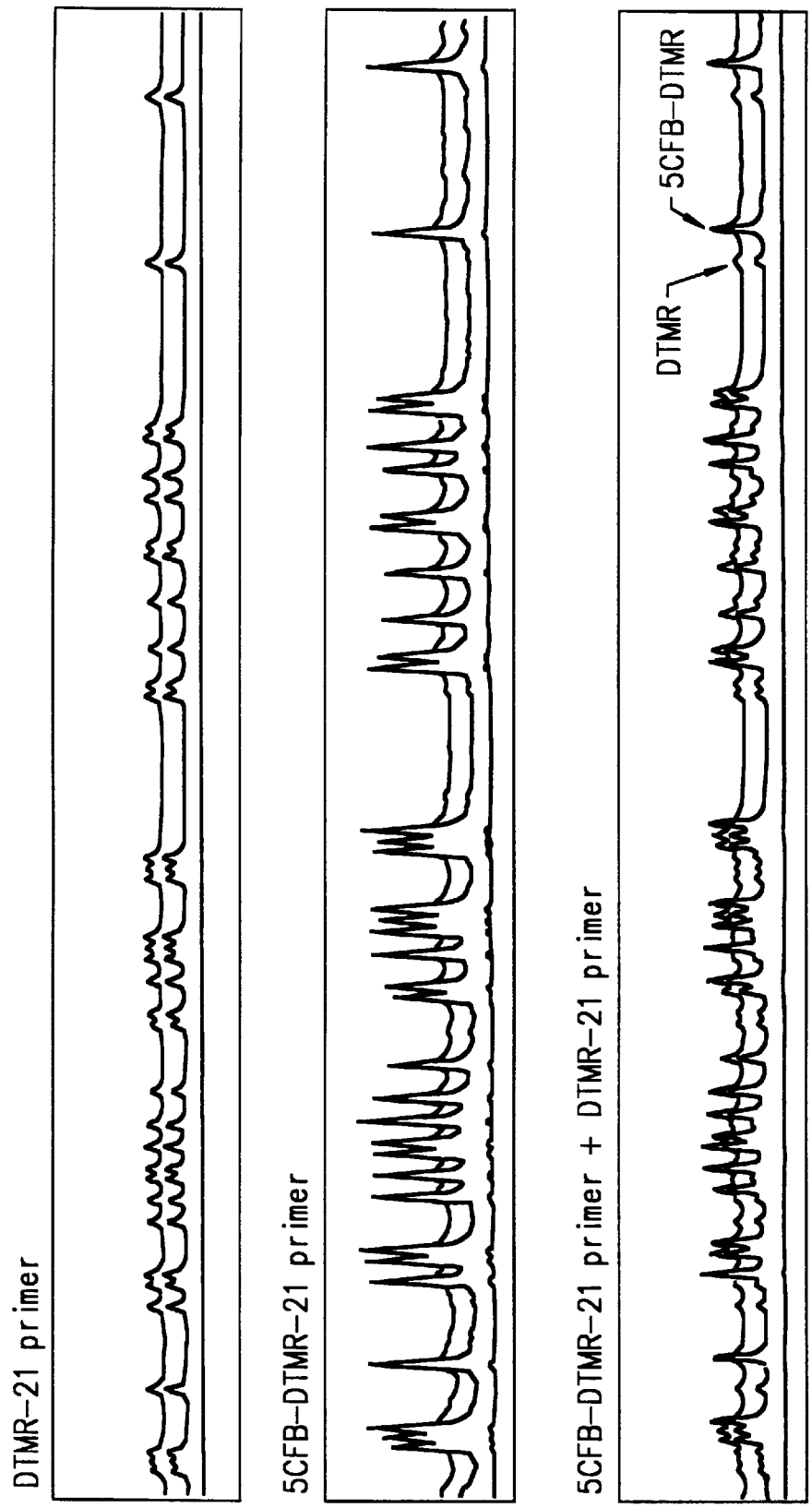
FIG. 11 is a plot of a mixture of labeled oligonucleotides generated during dye primer sequencing using 6-CFB-DTMR-2 and DTMR-2 labeled primers.

In this example, dye primer sequencing was performed on M13 (SEQ. ID. NO.: 2) using 5-CF-TMR-2, 5-CF-B-TMR-2, 6-CF-B-DTMR-2 and DTMR-2 labeled primers. In this example, dye primer sequencing was performed according to the *ABI PRISM™ 377 DNA Sequencer User's Manual, Rev. B,* January 1995, Chapter 2 (p/n 402114, The Perkin-Elmer Corporation, Foster City, Calif.). The dye was attached to the 5' end of M13–21 primer (SEQ. ID. NO.:3). Equimolar solutions of each primer were mixed with the M13 (SEQ. ID. NO.: 2) and sequenced with a single dideoxy nucleotide mixture (ddA/dNTP) and Taq FS. Plots of the resulting mixtures of oligonucleotides that were detected using 5-CF-TMR-2 and 5-CF-B-TMR-2 labeled primers are presented in FIG. 11. As can be seen from this figure, 5-CF-B-TMR-2 provides a significantly stronger signal than 5-CF-TMR-2, showing the fluorescence enhancement provided by the linker used in 5-CF-B-TMR-2.

Figure 12:
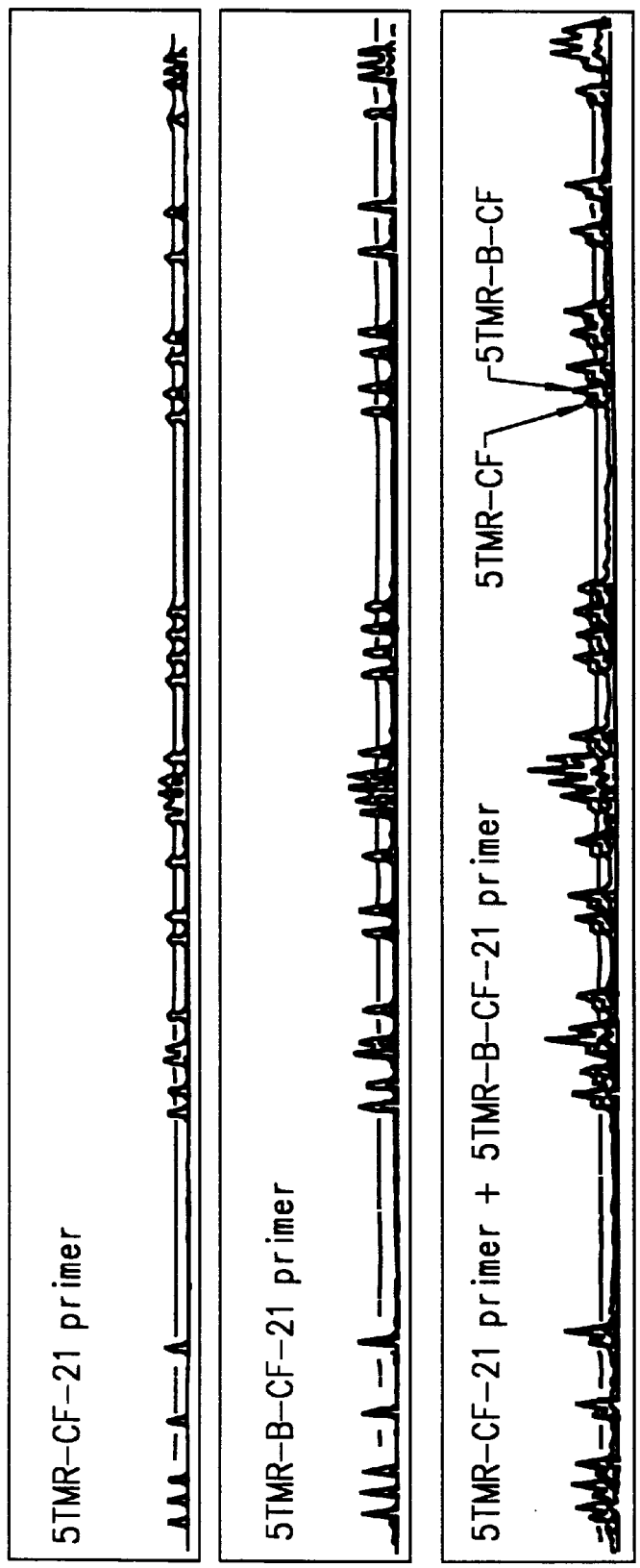
FIG. 12 is a plot of a mixture of labeled oligonucleotides generated during dye primer sequencing using 5-CF-TMR-2 and 5-CFB-TMR-2 labeled primers.

Plots of the resulting mixtures of oligonucleotides that were detected using 6-CF-B-DTMR-2 and DTMR-2 labeled primers are presented in FIG. 12. As can be seen from this figure, 6-CF-B-DTMR-2 provides a significantly stronger signal than DTMR-2, showing the fluorescence enhancement provided by the energy transfer dye.

10. Dye Primer Sequencing Using Four Dyes

Figure 13:
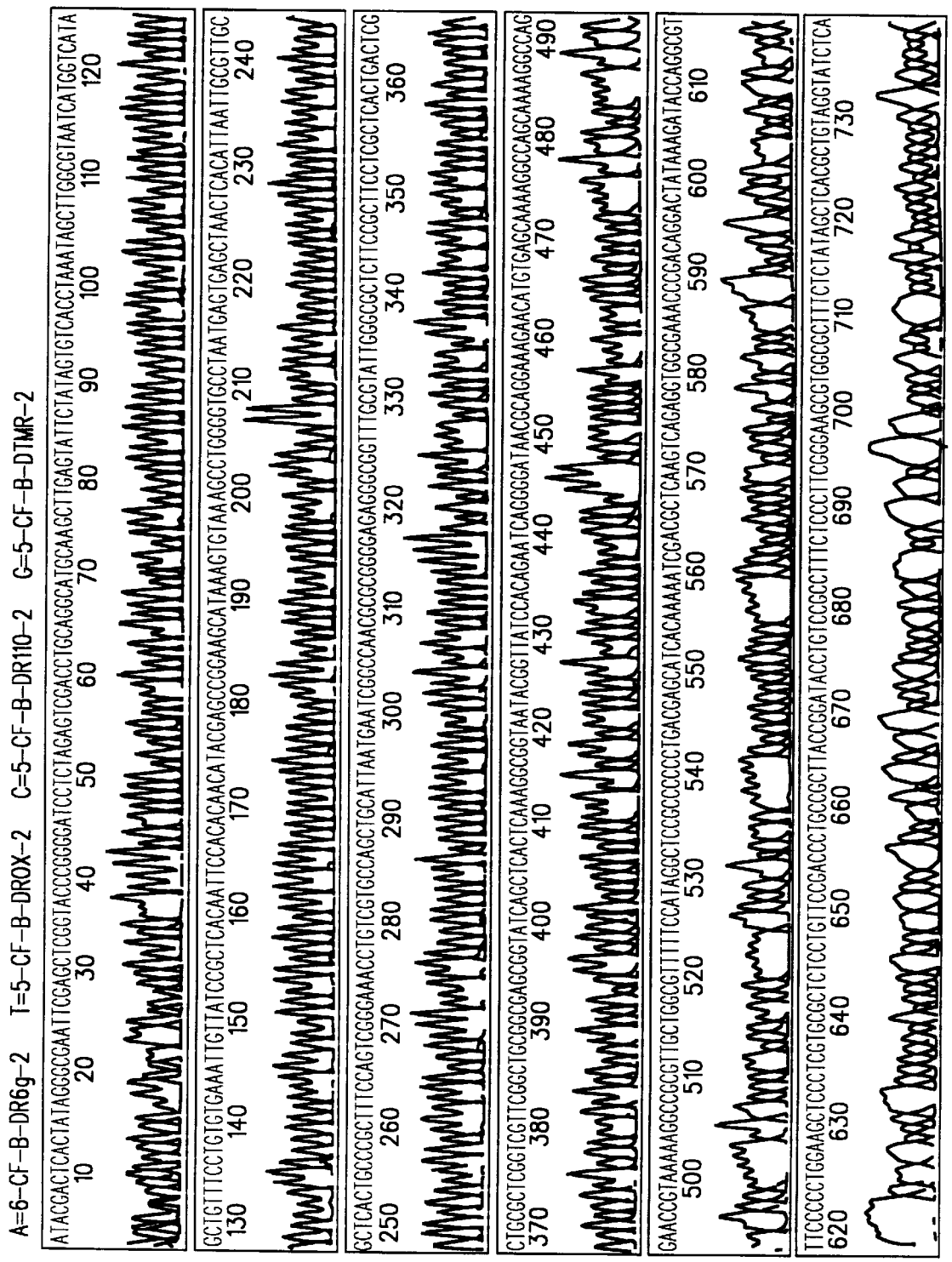
FIG. 13 is a four color plot of dye primer sequencing using a four dye set including 5-CFB-DR110-2, 6-CFB-DR6g-2, 5-CFB-DTMR-2, and 5-CFB-DROX-2.

Dye primer sequencing was performed on the PGEM (SEQ. ID. NO.: 3) using a set of four dyes attached to the M13–21 primer (SEQ. ID. NO. 2) as described in Example 5. FIG. 13 is a four color plot of the dye labeled oligonucleotides produced from the sequencing. The peak for cytosine corresponds to the fluorescence of 5-CFB-DR110-2. The peak for adenosine corresponds to the fluorescence of 6-CFB-DR6g-2. The peak for guanosine corresponds to the fluorescence of 5-CFBD-TMR-2. The peak for thymidine corresponds to the fluorescence of 5-CFB-DROX-2.

As can be seen from FIG. 13, each of the dye labeled oligonucleotides exhibit significant fluorescence intensity. In addition, the different dye labeled oligonucleotides exhibit sufficiently similar mobility so that good resolution of the series of peaks is achieved.

The foregoing description of preferred embodiments of the invention has been presented for purposes of illustration and description. It is not intended to be exhaustive or to limit the invention to the precise forms disclosed. Obviously, many modifications and variations will be apparent to practitioners skilled in this art and are intended to fall within the scope of the invention.

What is claimed is:

1. An energy transfer dye having the structure

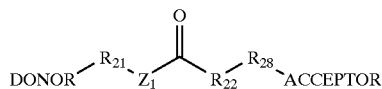

where

DONOR is a dye capable of absorbing light at a first wavelength and emitting excitation energy in response;

ACCEPTOR is dye which is capable of absorbing the excitation energy emitted by the donor dye and fluorescing at a second wavelength in response;

$Z_1$ is selected from the group consisting of NH, sulfur and oxygen;

$R_{21}$ is a $C_{1-5}$ alkyl attached to the donor dye;

$R_{22}$ includes a functional group selected from the group consisting of an alkene, diene, alkyne, a five and six membered ring having at least one unsaturated bond or a fused ring structure which is attached to the carbonyl carbon; and $R_{28}$ includes a functional group which attaches the linker to the acceptor dye.

2. The energy transfer dye according to claim 1 wherein $R_{22}$ includes a five or six membered ring selected from the group consisting of cyclopentene, cyclohexene, cyclopentadiene, cyclohexadiene, furan, thiofuran, pyrrole, isopyrole, isoazole, pyrazole, isoimidazole, pyran, pyrone, benzene, pyridine, pyridazine, pyrimidine, pyrazine oxazine, indene, benzofuran, thionaphthene, indole and naphthalene.

3. The energy transfer dye according to claim 1 wherein the dye has the structure

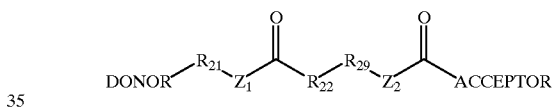

wherein $Z_2$ is selected from the group consisting of NH, sulfur and oxygen; and $R_{29}$ is a $C_{15}$ alkyl.

4. The energy transfer dye according to claim 1 wherein the donor dye is a member of the xanthene class of dyes.

5. The energy transfer dye according to claim 4 wherein the acceptor dye is a member of a class of dyes selected from the group consisting of xanthene, cyanine, phthalocyanine and squaraine dyes.

6. The energy transfer dye according to claim 1 wherein the donor dye is a member of a class of dyes selected from the group consisting of fluorescein, rhodamine and asymmetric benzoxanthene dyes.

7. The energy transfer dye according to claim 6 wherein the acceptor dye is a member of a class of dyes selected from the group consisting of xanthene, cyanine, phthalocyanine and squaraine dyes.

8. The energy transfer dye according to claim 1 wherein the donor dye is selected from the group consisting of carboxyfluoresceins, 4,7-dichlorofluorescein dyes, asymmetric benzoxanthene dyes, rhodamine, 4,7-dichlororhodamine dyes, carboxyrhodamines, N,N,N',N'-tetramethyl carboxyrhodamines, carboxy R110, and carboxy R6G.

9. The energy transfer dye according to claim 1 wherein the acceptor dye is selected from the group consisting of 4,7-dichlorofluorescein dyes, asymmetric benzoxanthene dyes, rhodamine, 4,7-dichlororhodamine dyes, carboxyrhodamines, N,N, N', N'-tetramethyl carboxyrhodamines, carboxy R110, carboxy R6G, carboxy-X-rhodamines and Cy5.

10. The energy transfer dye according to claim 1 wherein the acceptor dye is selected from the group consisting DR110-2, DR6G-2, DTMR and DROX.

11. An energy transfer dye having the structure

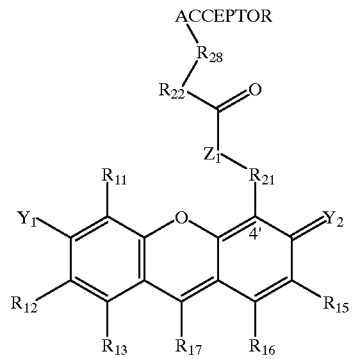

where $Y_1$ and $Y_2$ are each independently selected from the group consisting of hydroxyl, oxygen, iminium and amine;

$Z_1$ is selected from the group consisting of NH, sulfur and oxygen;

$R_{11}$–$R_{13}$ and $R_{15}$–$R_{17}$ are each independently selected from the group consisting of hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof;

$R_{21}$ is a $C_{1-5}$ alkyl;

$R_{22}$ includes a functional group selected from the group consisting of an alkene, diene, alkyne, a five and six membered ring having at least one unsaturated bond or a fused ring structure which is attached to the carbonyl carbon;

$R_{28}$ includes a functional group which attaches the linker to the acceptor dye; and ACCEPTOR is dye which is capable of absorbing excitation energy emitted by a member of the xanthene class of dyes.

12. The energy transfer dye according to claim 11 wherein $R_{22}$ includes a five or six membered ring selected from the group consisting of cyclopentene, cyclohexene, cyclopentadiene, cyclohexadiene, furan, thiofuran, pyrrole, isopyrole, isoazole, pyrazole, isoimidazole, pyran, pyrone, benzene, pyridine, pyridazine, pyrimidine, pyrazine oxazine, indene, benzofuran, thionaphthene, indole and naphthalene.

13. The energy transfer dye according to claim 11 wherein the dye has the structure

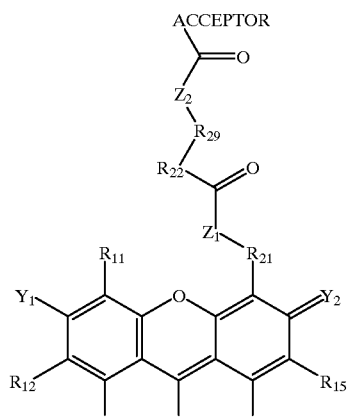

wherein $Z_2$ is selected from the group consisting of NH, sulfur and oxygen; and $R_{29}$ is a $C_{1-5}$ alkyl.

14. The energy transfer dye according to claim 11 wherein the acceptor dye is a member of a class of dyes selected from the group consisting of xanthene, cyanine, phthalocyanine and squaraine dyes.

15. The energy transfer dye according to claim 11 wherein the donor dye is a member of a class of dyes selected from the group consisting of fluorescein, rhodamine and asymmetric benzoxanthene dyes.

16. The energy transfer dye according to claim 11 wherein the acceptor dye is a member of a class of dyes selected from the group consisting of xanthene, cyanine, phthalocyanine and squaraine dyes.

17. The energy transfer dye according to claim 11 wherein the donor dye is selected from the group consisting of carboxyfluoresceins, 4,7-dichlorofluorescein dyes, asymmetric benzoxanthene dyes, rhodamine, carboxyrhodamines, N,N,N',N'-tetramethyl carboxyrhodamines, carboxy R110 and carboxy R6G.

18. The energy transfer dye according to claim 17 wherein the acceptor dye is a member of a class of dyes selected from the group consisting of xanthene, cyanine, phthalocyanine and squaraine dyes.

19. The energy transfer dye according to claim 11 wherein the acceptor dye is selected from the group consisting of 4,7-dichlorofluorescein dyes, asymmetric benzoxanthene dyes, rhodamine, 4,7-dichlororhodamine dyes, carboxyrhodamines, N, N,N',N'-tetramethyl carboxyrhodamines, carboxy R110, carboxy R6G, carboxy-X-rhodamines and Cy5.

20. The energy transfer dye according to claim 11 wherein the acceptor has the general structure

93

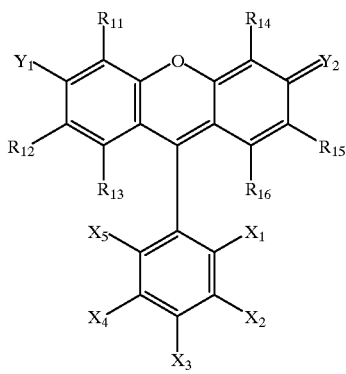

wherein:
Y₁ and Y₂ are each independently selected from the group consisting of hydroxyl, oxygen, iminium and amine;
R₁₁–R₁₆ are each independently selected from the group consisting of hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof;
X₁–X₅ are each independently selected from the group consisting of hydrogen, fluorine, chlorine, bromine, iodine, carboxyl, alkyl, alkene, alkyne, sulfonate, amino, ammonium, amido, nitrile, alkoxy, where adjacent substituents are taken together to form a ring, and combinations thereof; and
one of X₃ and X₄ is attached to the R₂₈ group.

21. The energy transfer dye according to claim 11 wherein the acceptor dye has the general structure

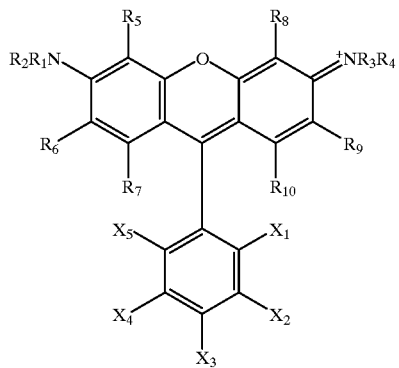

wherein:
R₁–R₄ are each independently selected from the group consisting of hydrogen, and alkyl or where one or more of the groups of R₁ and R₅, R₂ and R₆, R₃ and R₈, R₄ and R₉ are taken together to form a ring;
R₅–R₁₀ are each independently selected from the group consisting of hydrogen, fluorine, chlorine, bromine, iodine, carboxyl, alkyl, alkene, alkyne, sulfonate, sulfone, amino, ammonium, amido, nitrile, alkoxy, phenyl, and substituted phenyl, or where two or more of R₅–R₁₀ are taken together to form one or more rings;
X₁, X₃ and X₄ are each independently selected from the group consisting of hydrogen, fluorine, chlorine, bromine, iodine, carboxyl, alkyl, alkene, alkyne, sulfonate, sulfone, amino, ammonium, amido, nitrile, or alkoxy;

94

X₂ and X₅ are chlorine; and
one of X₃ and X₄ are attached to R₂₈.

22. The energy transfer dye according to claim 21 wherein the rings formed by substituents R₅–R₁₀ are 5, 6 or 7 membered rings.

23. The energy transfer dye according to claim 21 wherein one or more of the groups of R₁ and R₅, R₂ and R₆, R₃ and R₈, R₄ and R₉ are taken together to form a 5, 6 or 7 membered ring.

24. The energy transfer dye according to claim 21 wherein R₁–R₁₀, X₁, X₃ and X₄ are selected to correspond to a dye selected from the group consisting of DR110-2, DR6G-2, DTMR-2, and DROX-2.

25. An energy transfer fluorescent dye having the general structure

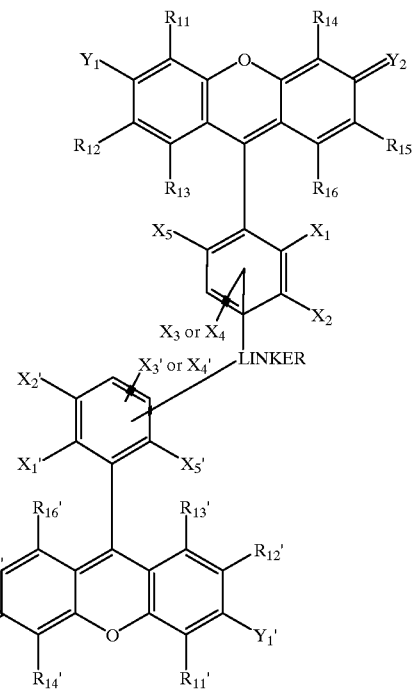

wherein:
Y₁, Y₁', Y₂', and Y₂' are each independently selected from the group consisting of hydroxyl, oxygen, iminium and amine,
R₁₁–R₁₆ and R₁₁'–R₁₆' are each independently selected from the group consisting of hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof, and
X₁–X₅ and X₁'–X₅' are each independently selected from the group consisting of hydrogen, fluorine, chlorine, bromine, iodine, carboxyl, alkyl, alkene, alkyne, sulfonate, amino, ammonium, amido, nitrile, alkoxy, where adjacent substituents are taken together to form a ring, and combinations thereof;
Y₁, Y₂, R₁₁–R₁₆, and X₁–X₅ are selected to correspond to a donor dye capable of absorbing light at a first wavelength and emitting excitation energy in response;
Y₁', Y₂', R₁₁'–R₁₆', and X₁'–X₅' are selected to correspond to an acceptor dye which is capable of absorbing the excitation energy emitted by the donor dye and fluorescing at a second wavelength in response; and one of $X_3$ and $X_4$ and one of $X_3'$ and $X_4'$ are taken together to form a linker having the general formula $R_{25}Z_3C(O)R_{37}$ where $R_{25}$ is a $C_{1-4}$ alkyl attached to the donor dye at the $X_3$ or $X_4$ substituent, $Z_3$ is either NH, O or S, C(O) is a carbonyl group and $R_{37}$ is a substituent attached to the acceptor dye at the $X_3'$ or $X_1'$ substituent.

26. A fluorescently labeled reagent comprising:

a reagent selected from the group consisting of a nucleoside, nucleoside monophosphate, nucleoside diphosphate, nucleoside triphosphate, oligonucleotide and oligonucleotide analog, modified to be linked to an energy transfer fluorescent dye; and an energy transfer fluorescent dye attached to the reagent, the energy transfer fluorescent dye including a dye having the structure

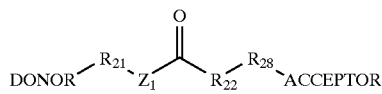

where

DONOR is a dye capable of absorbing light at a first wavelength and emitting excitation energy in response;

ACCEPTOR is dye which is capable of absorbing the excitation energy emitted by the donor dye and fluorescing at a second wavelength in response;

$Z_1$ is selected from the group consisting of NH, sulfur and oxygen;

$R_{21}$ is a $C_{1-5}$ alkyl attached to the donor dye;

$R_{22}$ includes a functional group selected from the group consisting of an alkene, diene, alkyne, a five and six membered ring having at least one unsaturated bond or a fused ring structure which is attached to the carbonyl carbon; and $R_{28}$ includes a functional group which attaches the linker to the acceptor dye.

27. The fluorescently labeled reagent according to claim 26 wherein $R_{22}$ includes a five or six membered ring selected from the group consisting of cyclopentene, cyclohexene, cyclopentadiene, cyclohexadiene, furan, thiofuran, pyrrole, isopyrole, isoazole, pyrazole, isoimidazole, pyran, pyrone, benzene, pyridine, pyridazine, pyrimidine, pyrazine oxazine, indene, benzofuran, thionaphthene, indole and naphthalene.

28. The fluorescently labeled reagent according to claim 26 wherein the dye has the structure

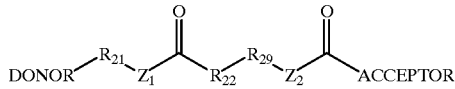

wherein $Z_2$ is selected from the group consisting of NH, sulfur and oxygen; and $R_{29}$ is a $C_{1-5}$ alkyl.

29. The fluorescently labeled reagent according to claim 26 wherein the donor dye is a member of the xanthene class of dyes.

30. The fluorescently labeled reagent according to claim 29 wherein the acceptor dye is a member of a class of dyes selected from the group consisting of xanthene, cyanine, phthalocyanine and squaraine dyes.

31. The fluorescently labeled reagent according to claim 26 wherein the donor dye is a member of a class of dyes selected from the group consisting of fluorescein, rhodamine and asymmetric benzoxanthene dyes.

32. The fluorescently labeled reagent according to claim 26 wherein the donor dye is selected from the group consisting of carboxyfluoresceins, 4,7-dichlorofluorescein dyes, asymmetric benzoxanthene dyes, rhodamine, 4,7-dichlororhodamine dyes, carboxyrhodamines, N,N,N',N'-tetramethyl carboxyrhodamines, carboxy R110, and carboxy R6G.

33. The fluorescently labeled reagent according to claim 26 wherein the acceptor dye is selected from the group consisting of 4,7-dichlorofluorescein dyes, asymmetric benzoxanthene dyes, rhodamine, 4,7-dichlororhodamine dyes, carboxyrhodamines, N, N, N', N'-tetramethyl carboxyrhodamines, carboxy R110, carboxy R6G, carboxy-X-rhodamines and Cy5.

34. The fluorescently labeled reagent according to claim 26 wherein the acceptor dye is selected from the group consisting DR110-2, DR6G-2, DTMR and DROX.

35. The fluorescently labeled reagent according to claim 26 wherein the reagent is selected from the group consisting of deoxynucleoside, deoxynucleoside monophosphate, deoxynucleoside diphosphate and deoxynucleoside triphosphate.

36. The fluorescently labeled reagent according to claim 35 wherein the deoxynucleotides are selected from the group consisting of deoxycytosine, deoxyadenosine, deoxyguanosine, and deoxythymidine.

37. The fluorescently labeled reagent according to claim 26 wherein the reagent is selected from the group consisting of dideoxynucleoside, dideoxynucleoside monophosphate, dideoxynucleoside diphosphate and dideoxynucleoside triphosphate.

38. The fluorescently labeled reagent according to claim 26 wherein the dideoxynucleotides are selected from the group consisting of deoxycytosine, deoxyadenosine, deoxyguanosine, and deoxythymidine.

39. The fluorescently labeled reagent according to claim 35 wherein the reagent is an oligonucleotide.

40. The fluorescently labeled reagent according to claim 39 wherein the oligonucleotide has a 3' end which is extendable by using a polymerase.

41. A fluorescently labeled reagent comprising:

a reagent selected from the group consisting of a nucleoside, nucleoside monophosphate, nucleoside diphosphate, nucleoside triphosphate, oligonucleotide and oligonucleotide analog, modified to be linked to an energy transfer fluorescent dye; and an energy transfer fluorescent dye attached to the reagent, the energy transfer fluorescent dye including a dye having the structure

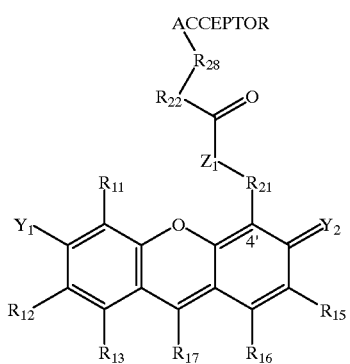

where
- $Y_1$ and $Y_2$ are each independently selected from the group consisting of hydroxyl, oxygen, iminium and amine;
- $Z_1$ is selected from the group consisting of NH, sulfur and oxygen;
- $R_{11}$–$R_{17}$ are each independently selected from the group consisting of hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof;
- $R_{21}$ is a $C_{1-5}$ alkyl;
- $R_{22}$ includes a functional group selected from the group consisting of an alkene, diene, alkyne, a five and six membered ring having at least one unsaturated bond or a fused ring structure which is attached to the carbonyl carbon;
- $R_{28}$ includes a functional group which attaches the linker to the acceptor dye; and
- ACCEPTOR is dye which is capable of absorbing excitation energy emitted by a member of the xanthene class of dyes.

42. The fluorescently labeled reagent according to claim 41 wherein $R_{22}$ includes a five or six membered ring selected from the group consisting of cyclopentene, cyclohexene, cyclopentadiene, cyclohexadiene, furan, thiofuran, pyrrole, isopyrole, isoazole, pyrazole, isoimidazole, pyran, pyrone, benzene, pyridine, pyridazine, pyrimidine, pyrazine oxazine, indene, benzofuran, thionaphthene, indole and naphthalene.

43. The fluorescently labeled reagent according to claim 41 wherein the acceptor dye is a member of a class of dyes selected from the group consisting of xanthene, cyanine, phthalocyanine and squaraine dyes.

44. The fluorescently labeled reagent according to claim 41 wherein the donor dye is a member of a class of dyes selected from the group consisting of fluorescein, rhodamine and asymmetric benzoxanthene dyes.

45. The fluorescently labeled reagent according to claim 44 wherein the acceptor dye is a member of a class of dyes selected from the group consisting of xanthene, cyanine, phthalocyanine and squaraine dyes.

46. The fluorescently labeled reagent according to claim 41 wherein the donor dye is selected from the group consisting of carboxyfluoresceins, 4,7-dichlorofluorescein dyes, asymmetric benzoxanthene dyes, rhodamine, carboxyrhodamines, N,N,N',N'-tetramethyl carboxyrhodamines, carboxy R110, and carboxy R6G.

47. The fluorescently labeled reagent according to claim 41 wherein the acceptor dye is selected from the group consisting of 4,7-dichlorofluorescein dyes, asymmetric benzoxanthene dyes, rhodamine, 4,7-dichlororhodamine dyes, carboxyrhodamines, N,N,N',N'-tetramethyl carboxyrhodamines, carboxy R110, carboxy R6G, carboxy-X-rhodamines and Cy5.

48. The fluorescently labeled reagent according to claim 41 wherein the acceptor has the general structure

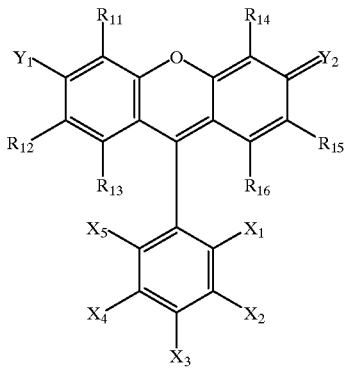

wherein:
- $Y_1$ and $Y_2$ are each independently selected from the group consisting of hydroxyl, oxygen, iminium and amine;
- $R_{11}$–$R_{16}$ are each independently selected from the group consisting of hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof;
- $X_1$–$X_5$ are each independently selected from the group consisting of hydrogen, fluorine, chlorine, bromine, iodine, carboxyl, alkyl, alkene, alkyne, sulfonate, amino, ammonium, amido, nitrile, alkoxy, where adjacent substituents are taken together to form a ring, and combinations thereof; and
- one of $X_3$ and $X_4$ is attached to the $R_{28}$ group.

49. The fluorescently labeled reagent according to claim 41 wherein the acceptor dye has the general structure

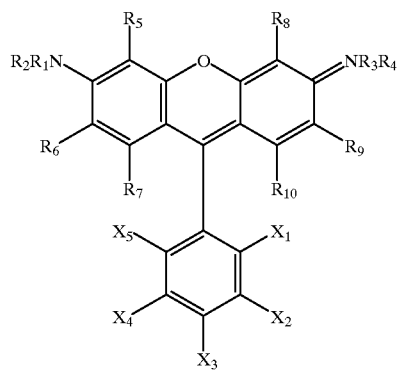

wherein:
- $R_1$–$R_4$ are each independently selected from the group consisting of hydrogen, and alkyl or where one or more of the groups of $R_1$ and $R_5$, $R_2$ and $R_6$, $R_3$ and $R_7$, $R_4$ and $R_8$ are taken together to form a ring;
- $R_5$–$R_{10}$ are each independently selected from the group consisting of hydrogen, fluorine, chlorine, bromine, iodine, carboxyl, alkyl, alkene, alkyne, sulfonate, sulfone, amino, ammonium, amido, nitrile, alkoxy, phenyl, and substituted phenyl, or where two or more of $R_5$–$R_{10}$ are taken together to form one or more rings;

$X_1$, $X_3$ and $X_4$ are each independently selected from the group consisting of hydrogen, fluorine, chlorine, bromine, iodine, carboxyl, alkyl, alkene, alkyne, sulfonate, sulfone, amino, ammonium, amido, nitrile, or alkoxy;

$X_2$ and $X_5$ are chlorine; and one Of $X_3$ and $X_4$ are attached to $R_{28}$.

50. The fluorescently labeled reagent according to claim 49 wherein $R_1$–$R_{10}$, $X_1$, $X_3$ and $X_4$ are selected to correspond to a dye selected from the group consisting of DR110-2, DR6G-2, DTMR-2, and DROX-2.

51. The fluorescently labeled reagent according to claim 41 wherein the reagent is selected from the group consisting of deoxynucleoside, deoxynucleoside monophosphate, deoxynucleoside diphosphate and deoxynucleoside triphosphate.

52. The fluorescently labeled reagent according to claim 51 wherein the deoxynucleotides are selected from the group consisting of deoxycytosine, deoxyadenosine, deoxyguanosine, and deoxythymidine.

53. The fluorescently labeled reagent according to claim 41 wherein the reagent is selected from the group consisting of dideoxynucleoside, dideoxynucleoside monophosphate, dideoxynucleoside diphosphate and dideoxynucleoside triphosphate.

54. The fluorescently labeled reagent according to claim 41 wherein the dideoxynucleotides are selected from the group consisting of deoxycytosine, deoxyadenosine, deoxyguanosine, and deoxythymidine.

55. The fluorescently labeled reagent according to claim 41 wherein the reagent is an oligonucleotide.

56. The fluorescently labeled reagent according to claim 55 wherein the oligonucleotide has a 3' end which is extendable by using a polymerase.

57. A fluorescently labeled reagent comprising:

a reagent selected from the group consisting of a nucleoside, nucleoside monophosphate, nucleoside diphosphate, nucleoside triphosphate, oligonucleotide and oligonucleotide analog, modified to be linked to an energy transfer fluorescent dye; and an energy transfer fluorescent dye attached to the reagent, the energy transfer fluorescent dye including a dye having the structure

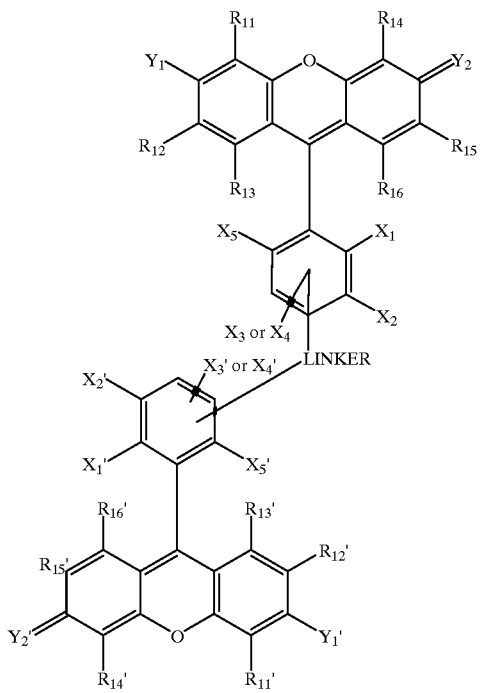

wherein:

$Y_1$, $Y_1'$, $Y_2$ and $Y_2'$ are each independently selected from the group consisting of hydroxyl, oxygen, iminium and amine, $R_{11}$–$R_{16}$ and $R_{11}'$–$R_{16}'$ are each independently selected from the group consisting of hydrogen, fluorine, chlorine, bromine, iodine, carboxyl, alkyl, alkene, alkyne, sulfonate, amino, ammonium, amido nitrile alkoxy, phenyl, substituted phenyl, where adjacent substituents are taken together to form a ring, and combinations thereof, and $X_1$–$X_5$ and $X_1'$–$X_5'$ are each independently selected from the group consisting of hydrogen, fluorine, chlorine, bromine, iodine, carboxyl, alkyl, alkene, alkyne, sulfonate, amino, ammonium, amido, nitrile, alkoxy, where adjacent substituents are taken together to form a ring, and combinations thereof;

$Y_1$, $Y_2$, $R_{11}$–$R_{16}$, and $X_1$–$X_5$ are selected to correspond to a donor dye capable of absorbing light at a first wavelength and emitting excitation energy in response;

$Y_1'$, $Y_2'$, $R_{11}'$–$R_{16}'$, and $X_1'$–$X_5'$ are selected to correspond to an acceptor dye which is capable of absorbing the excitation energy emitted by the donor dye and fluorescing at a second wavelength in response; and one of $X_3$ and $X_4$ and one of $X_3'$ and $X_4'$ are taken together to form a linker one of $X_3$ and $X_4$ and one of $X_3'$ and $X_4'$ are taken together to form a linker having the general formula $R_{25}Z_3C(O)R_{37}$ where $R_{25}$ is a $C_{1-4}$ alkyl attached to the donor dye at the $X_3$ or $X_4$ substituent, $Z_3$ is either NH, O or S, C(O) is a carbonyl group and $R_{37}$ is a substituent attached to the acceptor dye at the $X_3'$ or $X_1'$ substituent.

58. A method for sequencing a nucleic acid sequence comprising:

forming a mixture of extended labeled primers by hybridizing a nucleic acid sequence with a fluorescently labeled oligonucleotide primer in the presence of deoxynucleoside triphosphates, at least one dideoxynucleoside triphosphate and a DNA polymerase, the DNA polymerase extending the primer with the deoxynucleoside triphosphates until a dideoxynucleoside triphosphate is incorporated which terminates extension of the primer;

separating the mixture of extended primers; and determining the sequence of the nucleic acid sequence by fluorescently measuring the mixture of extended primers formed;

the fluorescently labeled oligonucleotide primer including an oligonucleotide sequence complementary to a portion of the nucleic acid sequence being sequenced and having a 3' end extendable by a polymerase, and an energy transfer fluorescent dye attached to the oligonucleotide, the energy transfer fluorescent dye having the structure

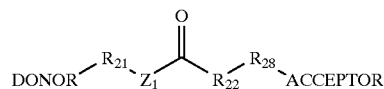

where

DONOR is a dye capable of absorbing light at a first wavelength and emitting excitation energy in response;

ACCEPTOR is dye which is capable of absorbing the excitation energy emitted by the donor dye and fluorescing at a second wavelength in response;

$Z_1$ is selected from the group consisting of NH, sulfur and oxygen;

$R_{21}$ is a $C_{1-5}$ alkyl attached to the donor dye;

$R_{22}$ includes a functional group selected from the group consisting of an alkene, diene, alkyne, a five and six membered ring having at least one unsaturated bond or a fused ring structure which is attached to the carbonyl carbon; and $R_{28}$ includes a functional group which attaches the linker to the acceptor dye.

59. A method for sequencing a nucleic acid sequence comprising:

forming a mixture of extended labeled primers by hybridizing a nucleic acid sequence with a fluorescently labeled oligonucleotide primer in the presence of deoxynucleoside triphosphates, at least one dideoxynucleoside triphosphate and a DNA polymerase, the DNA polymerase extending the primer with the deoxynucleoside triphosphates until a dideoxynucleoside triphosphate is incorporated which terminates extension of the primer;

separating the mixture of extended primers; and determining the sequence of the nucleic acid sequence by fluorescently measuring the mixture of extended primers formed;

the fluorescently labeled oligonucleotide primer including an oligonucleotide sequence complementary to a portion of the nucleic acid sequence being sequenced and having a 3' end extendable by a polymerase, and an energy transfer fluorescent dye attached to the oligonucleotide, the energy transfer fluorescent dye having the structure

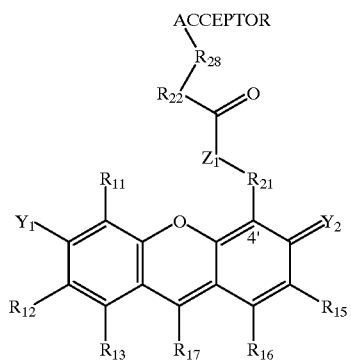

where $Y_1$ and $Y_2$ are each independently selected from the group consisting of hydroxyl, oxygen, iminium and amine;

$Z_1$ is selected from the group consisting of NH, sulfur and oxygen;

$R_{11}$–$R_{17}$ are each independently selected from the group consisting of hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof;

$R_21$ is a $C_{1-5}$ alkyl;

$R_{22}$ includes a functional group selected from the group consisting of an alkene, diene, alkyne, a five and six membered ring having at least one unsaturated bond or a fused ring structure which is attached to the carbonyl carbon;

$R_{28}$ includes a functional group which attaches the linker to the acceptor dye; and ACCEPTOR is dye which is capable of absorbing excitation energy emitted by a member of the xanthene class of dyes.

60. A method for sequencing a nucleic acid sequence comprising:

forming a mixture of extended primers by hybridizing a nucleic acid sequence with a primer in the presence of deoxynucleoside triphosphates, at least one fluorescently labeled dideoxynucleoside triphosphate and a DNA polymerase, the DNA polymerase extending the primer with the deoxynucleoside triphosphates until a fluorescently labeled dideoxynucleoside triphosphate is incorporated onto the extended primer which terminates extension of the primer;

separating the mixture of extended primers; and determining the sequence of the nucleic acid sequence by detecting the fluorescently labeled dideoxynucleotide attached to the separated mixture of extended primers;

the fluorescently labeled dideoxynucleoside triphosphate including a dideoxynucleoside triphosphate, and an energy transfer fluorescent dye attached to the dideoxynucleoside triphosphate, the energy transfer dye having the structure

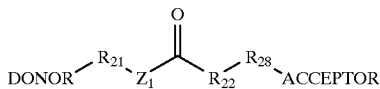

where

DONOR is a dye capable of absorbing light at a first wavelength and emitting excitation energy in response;

ACCEPTOR is dye which is capable of absorbing the excitation energy emitted by the donor dye and fluorescing at a second wavelength in response;

$Z_1$ is selected from the group consisting of NH, sulfur and oxygen;

$R_{21}$ is a $C_{1-5}$ alkyl attached to the donor dye;

$R_{22}$ includes a functional group selected from the group consisting of an alkene, diene, alkyne, a five and six membered ring having at least one unsaturated bond or a fused ring structure which is attached to the carbonyl carbon; and $R_{28}$ includes a functional group which attaches the linker to the acceptor dye.

61. A method for sequencing a nucleic acid sequence comprising:

forming a mixture of extended primers by hybridizing a nucleic acid sequence with a primer in the presence of deoxynucleoside triphosphates, at least one fluorescently labeled dideoxynucleoside triphosphate and a DNA polymerase, the DNA polymerase extending the primer with the deoxynucleoside triphosphates until a fluorescently labeled dideoxynucleoside triphosphate is incorporated onto the extended primer which terminates extension of the primer;

separating the mixture of extended primers; and determining the sequence of the nucleic acid sequence by detecting the fluorescently labeled dideoxynucleotide attached to the separated mixture of extended primers;

the fluorescently labeled dideoxynucleoside triphosphate including a dideoxynucleoside triphosphate, and an energy transfer fluorescent dye attached to the dideoxynucleoside triphosphate, the dye having the structure

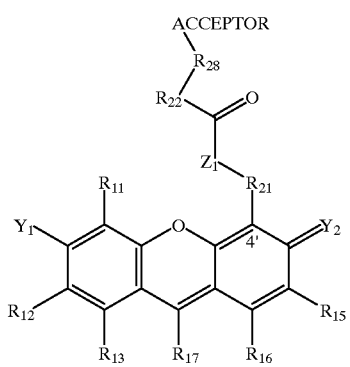

where $Y_1$ and $Y_2$ are each independently selected from the group consisting of hydroxyl, oxygen, iminium and amine;

$Z_1$ is selected from the group consisting of NH, sulfur and oxygen;

$R_{11}$–$R_{17}$ are each independently selected from the group consisting of hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof;

$R_{21}$ is a $C_{1-5}$ alkyl;

$R_{22}$ includes a functional group selected from the group consisting of an alkene, diene, alkyne, a five and six membered ring having at least one unsaturated bond or a fused ring structure which is attached to the carbonyl carbon;

$R_{28}$ includes a functional group which attaches the linker to the acceptor dye; and ACCEPTOR is dye which is capable of absorbing excitation energy emitted by a member of the xanthene class of dyes.

62. An energy transfer fluorescent dye comprising:

a donor dye which absorbs light at a first wavelength and emits excitation energy in response;

an acceptor dye selected from the group consisting of xanthene, cyanine and phthalocyanine dyes which is capable of absorbing the excitation energy emitted by the donor dye and fluorescing at a second wavelength in response, the acceptor having an emission maximum that is greater than about 600 nm; and a linker attaching the donor dye to the acceptor dye which has a sufficiently short length that the acceptor dye absorbs substantially all of the excitation energy emitted by the donor dye.

63. The energy transfer dye according to claim 61 wherein the acceptor dye has a rhodamine ring structure.

64. An energy transfer fluorescent dye comprising:

a donor dye which absorbs light at a first wavelength and emits excitation energy in response;

an acceptor dye selected from the group consisting of xanthene, cyanine and phthalocyanine dyes which is capable of absorbing the excitation energy emitted by the donor dye and fluorescing at a second wavelength in response, the acceptor having an emission maximum at least about 100 nm greater than the absorbance maximum of the donor dye; and a linker attaching the donor dye to the acceptor dye which has a sufficiently short length that the acceptor dye absorbs substantially all of the excitation energy emitted by the donor dye.

65. The energy transfer dye according to claim 64 wherein the acceptor dye has a rhodamine ring structure.

66. An energy transfer dye comprising:

a donor dye capable of absorbing light at a first wavelength and emitting excitation energy in response;

an acceptor dye capable of absorbing the excitation energy emitted by the donor dye and fluorescing at a second wavelength in response; and a linker linking the donor dye to the acceptor dye such that the acceptor dye absorbs substantially all of the excitation energy emitted by the donor dye, the linker including a functional group selected from the group consisting of an alkene, diene, alkyne, a five and six membered ring having at least one unsaturated bond or a fused ring structure.

67. The energy transfer dye according to claim 66 wherein the energy transfer dye has the structure:

105

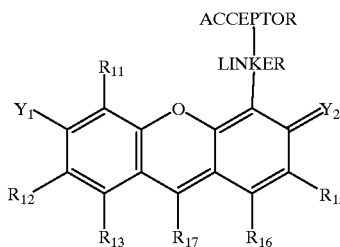

wherein
  $Y_1$ and $Y_2$ are each independently selected from the group consisting of hydroxyl, oxygen, iminium and amine; and
  $R_{11}$–$R_{13}$ and $R_{15}$–$R_{17}$ are each independently selected from the group consisting of hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof.

68. The energy transfer dye according to claim 66 wherein the energy transfer dye has the structure:

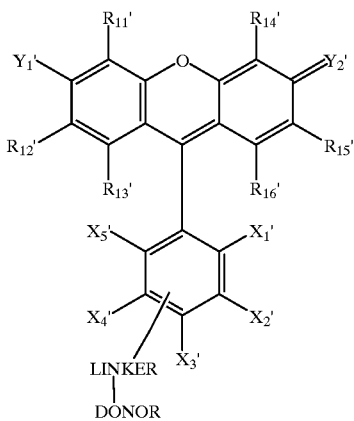

wherein
  $Y_1'$ and $Y_2'$ are each independently selected from the group consisting of hydroxyl, oxygen, iminium and amine;
  $R_{11}'$–$R_{16}'$ are each independently selected from the group consisting of hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof;
  $X_1'$–$X_5'$ are selected to correspond to an acceptor dye which is capable of absorbing the excitation energy emitted by the donor dye and fluorescing at a second wavelength in response; and

106 one of $X_3'$ and $X_4'$ includes the linker.

69. The energy transfer dye according to claim 66 wherein the energy transfer dye has the structure:

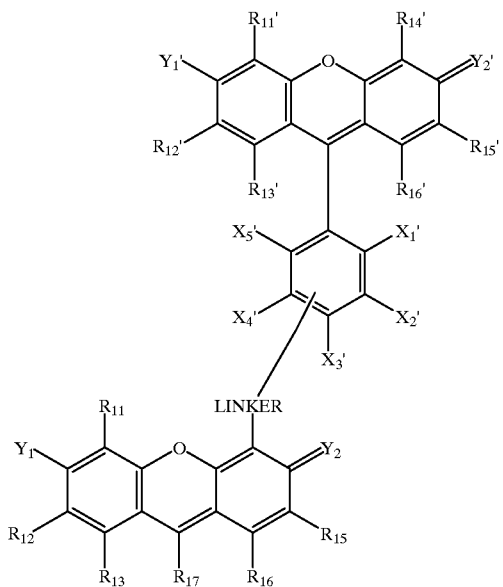

wherein:
  $Y_1$, $Y_1'$, $Y_2$ and $Y_2'$ are each independently selected from the group consisting of hydroxyl, oxygen, iminium and amine;
  $R_{11}$–$R_{13}$, $R_{15-R17}$ and $R_{11}'$–$R_{16}'$ are each independently selected from the group consisting of hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof;
  $X_1'$–$X_5'$ are each independently selected from the group consisting of hydrogen, fluorine, chlorine, bromine, iodine, carboxyl, alkyl, alkene, alkyne, sulfonate, amino, ammonium, amido, nitrile, alkoxy, where adjacent substituents are taken together to form a ring, and combinations thereof;
  $Y_1$, $Y_2$, $R_{11}$–$R_{13}$, and $R_{15}$–$R_{17}$ are selected to correspond to a donor dye capable of absorbing light at a first wavelength and emitting excitation energy in response;
  $Y_1'$, $Y_2'$, $R_{11}'$–$R_{16}'$, and $X_1'$–$X_5'$ are selected to correspond to an acceptor dye which is capable of absorbing the excitation energy emitted by the donor dye and fluorescing at a second wavelength in response; and
  one of $X_3'$ and $X_4'$ includes the linker.

70. The energy transfer dye according to claim 66 wherein the energy transfer dye has the structure:

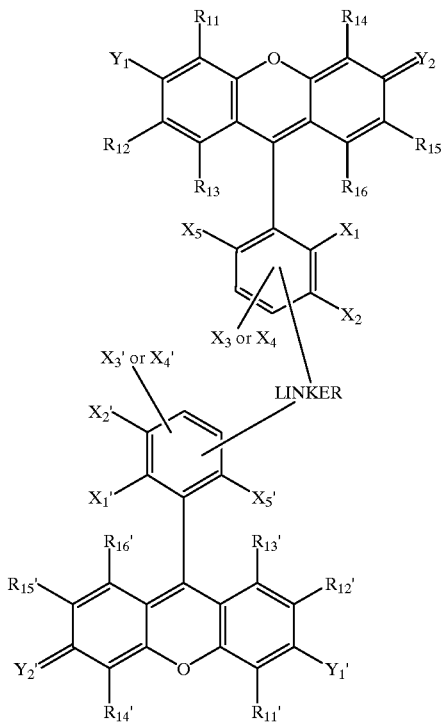

wherein:
- $Y_1$, $Y_1'$, $Y_2$ and $Y_2'$ are each independently selected from the group consisting of hydroxyl, oxygen, iminium and amine;
- $R_{11}$–$R_{16}$ and $R_{11}'$–$R_{16}'$ are each independently selected from the group consisting of hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof;
- $X_1$–$X_5$ and $X_1'$–$X_5'$ are each independently selected from the group consisting of hydrogen, fluorine, chlorine, bromine, iodine, carboxyl, alkyl, alkene, alkyne, sulfonate, amino, ammonium, amido, nitrile, alkoxy, where adjacent substituents are taken together to form a ring, and combinations thereof;
- $Y_1$, $Y_2$, $R_{11}$–$R_{16}$ and $X_1$–$X_5$ are selected to correspond to a donor dye capable of absorbing light at a first wavelength and emitting excitation energy in response;
- $Y_1'$, $Y_2'$, $R_{11}'$–$R_{16}'$, and $X_1'$–$X_5'$ are selected to correspond to an acceptor dye which is capable of absorbing the excitation energy emitted by the donor dye and fluorescing at a second wavelength in response; and
- one of $X_3$ and $X_4$ and one of $X_3'$ and $X_4'$ are taken together to form the linker.

71. The energy transfer dye according to claim 65 wherein the linker functional group is a five or six membered ring selected from the group consisting of cyclopentene, cyclohexene, cyclopentadiene, cyclohexadiene, furan, thiofuran, pyrrole, isopyrole, isoazole, pyrazole, isoimidazole, pyran, pyrone, benzene, pyridine, pyridazine, pyrimidine, pyrazine oxazine, indene, benzofuran, thionaphthene, indole and naphthalene.

72. The energy transfer dye according to claim 66 wherein the acceptor dye is a member of a class of dyes selected from the group consisting of xanthene, cyanine, phthalocyanine and squaraine dyes.

73. The energy transfer dye according to claim 66 wherein the donor dye is a member of the xanthene class of dyes.

74. The energy transfer dye according to claim 73 wherein the acceptor dye is a member of a class of dyes selected from the group consisting of xanthene, cyanine, phthalocyanine and squaraine dyes.

75. The energy transfer dye according to claim 66 wherein the donor dye is a member of a class of dyes selected from the group consisting of fluorescein, rhodamine and asymmetric benzoxanthene dyes.

76. The energy transfer dye according to claim 75 wherein the acceptor dye is a member of a class of dyes selected from the group consisting of xanthene, cyanine, phthalocyanine and squaraine dyes.

77. The energy transfer dye according to claim 66 wherein the donor dye is selected from the group consisting of carboxyfluoresceins, 4,7-dichlorofluorescein dyes, asymmetric benzoxanthene dyes, rhodamine, 4,7-dichlororhodamine dyes, carboxyrhodamines, N,N,N',N'-tetramethyl carboxyrhodamines, carboxy R110s, and carboxy R6Gs.

78. The energy transfer dye according to claim 66 wherein the acceptor dye is selected from the group consisting of 4,7-dichlorofluorescein dyes, asymmetric benzoxanthene dyes, rhodamine, 4,7-dichlororhodamine dyes, carboxyrhodamines, N,N,N',N'-tetramethyl carboxyrhodamines, carboxy R110s, carboxy R6Gs, carboxy-X-rhodamines and Cy5.

79. The energy transfer dye according to claim 66 wherein the acceptor dye is selected from the group consisting DR110-2, DR6G-2, DTMR and DROX.

80. A fluorescently labeled reagent comprising:
- a reagent selected from the group consisting of a nucleoside, nucleoside monophosphate, nucleoside diphosphate, nucleoside triphosphate, oligonucleotide and oligonucleotide analog, modified to be linked to an energy transfer fluorescent dye; and
- an energy transfer fluorescent dye attached to the reagent, the energy transfer fluorescent dye including
  - a donor dye capable of absorbing light at a first wavelength and emitting excitation energy in response;
  - an acceptor dye capable of absorbing the excitation energy emitted by the donor dye and fluorescing at a second wavelength in response; and
  - a linker linking the donor dye to the acceptor dye such that the acceptor dye absorbs substantially all of the excitation energy emitted by the donor dye, the linker including a functional group selected from the group consisting of an alkene, diene, alkyne, a five and six membered ring having at least one unsaturated bond or a fused ring structure.

81. The fluorescently labeled reagent according to claim 80 wherein the energy transfer fluorescent dye has the structure:

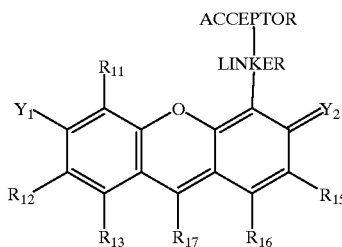

wherein

Y$_1$ and Y$_2$ are each independently selected from the group consisting of hydroxyl, oxygen, iminium and amine; and R$_{11}$–R$_{13}$ and R$_{15}$–R$_{17}$ are each independently selected from the group consisting of hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof.

82. The fluorescently labeled reagent according to claim 70 wherein the energy transfer fluorescent dye has the structure:

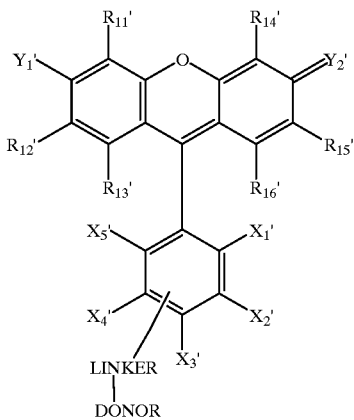

wherein

Y$_1$' and Y$_2$' are each independently selected from the group consisting of hydroxyl, oxygen, iminium and amine;

R$_{11}$'–R$_{16}$' are each independently selected from the group consisting of hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof;

X$_1$'–X$_5$' are selected to correspond to an acceptor dye which is capable of absorbing the excitation energy emitted by the donor dye and fluorescing at a second wavelength in response; and one of X$_3$' and X$_4$' includes the linker.

83. The fluorescently labeled reagent according to claim 80 wherein the energy transfer fluorescent dye has the structure:

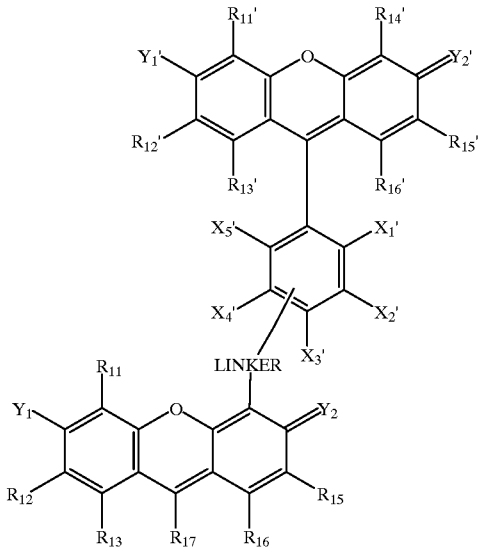

wherein:

Y$_1$, Y$_1$', Y$_2$ and Y$_2$' are each independently selected from the group consisting of hydroxyl, oxygen, iminium and amine;

R$_{11}$–R$_{13}$, R$_{15}$–R$_{17}$ and R$_{11}$'–R$_{16}$' are each independently selected from the group consisting of hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof;

X$_1$'–X$_5$' are each independently selected from the group consisting of hydrogen, fluorine, chlorine, bromine, iodine, carboxyl, alkyl, alkene, alkyne, sulfonate, amino, ammonium, amido, nitrile, alkoxy, where adjacent substituents are taken together to form a ring, and combinations thereof;

Y$_1$, Y$_2$, R$_{11}$–R$_{13}$ and R$_{15}$–R$_{17}$ are selected to correspond to a donor dye capable of absorbing light at a first wavelength and emitting excitation energy in response;

Y$_1$', Y$_2$', R$_{11}$'–R$_{16}$', and X$_1$'–X$_5$' are selected to correspond to an acceptor dye which is capable of absorbing the excitation energy emitted by the donor dye and fluorescing at a second wavelength in response; and one of X$_3$' and X$_4$' includes the linker.

84. The fluorescently labeled reagent according to claim 80 wherein the energy transfer fluorescent dye has the structure:

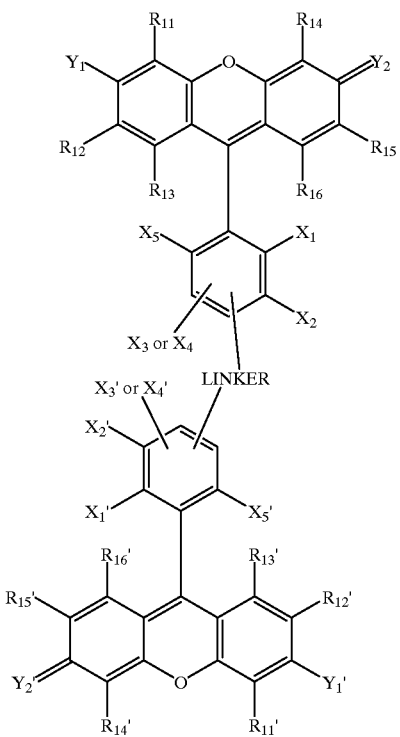

wherein:
  $Y_1$, $Y_1'$, $Y_2$ and $Y_2'$ are each independently selected from the group consisting of hydroxyl, oxygen, iminium and amine;
  $R_{11}$–$R_{16}$ and $R_{11}'$–$R_{16}'$ are each independently selected from the group consisting of hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof;
  $X_1$–$X_5$ and $X_1'$–$X_5'$ are each independently selected from the group consisting of hydrogen, fluorine, chlorine, bromine, iodine, carboxyl, alkyl, alkene, alkyne, sulfonate, amino, ammonium, amido, nitrile, alkoxy, where adjacent substituents are taken together to form a ring, and combinations thereof;
  $Y_1$, $Y_2$, $R_{11}$–$R_{16}$ and $X_1$–$X_5$ are selected to correspond to a donor dye capable of absorbing light at a first wavelength and emitting excitation energy in response;
  $Y_1'$, $Y_2'$, $R_{11}'$–$R_{16}'$, and $X_1'$–$X_5'$ are selected to correspond to an acceptor dye which is capable of absorbing the excitation energy emitted by the donor dye and fluorescing at a second wavelength in response; and
  one of $X_3$ and $X_4$ and one of $X_3'$ and $X_4'$ are taken together to form the linker.

85. The fluorescently labeled reagent according to claim 80 wherein the linker functional group is a five or six membered ring selected from the group consisting of cyclopentene, cyclohexene, cyclopentadiene, cyclohexadiene, furan, thiofuran, pyrrole, isopyrole, isoazole, pyrazole, isoimidazole, pyran, pyrone, benzene, pyridine, pyridazine, pyrimidine, pyrazine oxazine, indene, benzofuran, thionaphthene, indole and naphthalene.

86. The fluorescently labeled reagent according to claim 80 wherein the acceptor dye is a member of a class of dyes selected from the group consisting of xanthene, cyanine, phthalocyanine and squaraine dyes.

87. The fluorescently labeled reagent according to claim 80 wherein the donor dye is a member of the xanthene class of dyes.

88. The fluorescently labeled reagent according to claim 87 wherein the acceptor dye is a member of a class of dyes selected from the group consisting of xanthene, cyanine, phthalocyanine and squaraine dyes.

89. The fluorescently labeled reagent according to claim 80 wherein the donor dye is a member of a class of dyes selected from the group consisting of fluorescein, rhodamine and asymmetric benzoxanthene dyes.

90. The fluorescently labeled reagent according to claim 89 wherein the acceptor dye is a member of a class of dyes selected from the group consisting of xanthene, cyanine, phthalocyanine and squaraine dyes.

91. The fluorescently labeled reagent according to claim 80 wherein the donor dye is selected from the group consisting of carboxyfluoresceins, 4,7-dichlorofluorescein dyes, asymmetric benzoxanthene dyes, rhodamine, 4,7-dichlororhodamine dyes, carboxyrhodamines, N,N,N',N'-tetramethyl carboxyrhodamines, carboxy R110s, and carboxy R6Gs.

92. The fluorescently labeled reagent according to claim 80 wherein the acceptor dye is selected from the group consisting of 4,7-dichlorofluorescein dyes, asymmetric benzoxanthene dyes, rhodamine, 4,7-dichlororhodamine dyes, carboxyrhodamines, N,N,N',N'-tetramethyl carboxyrhodamines, carboxy R110s, carboxy R6Gs, carboxy-X-rhodamines and Cy5.

93. The fluorescently labeled reagent according to claim 80 wherein the acceptor dye is selected from the group consisting DR110-2, DR6G-2, DTMR and DROX.

94. The fluorescently labeled reagent according to claim 80 wherein the reagent is selected from the group consisting of deoxynucleoside, deoxynucleoside monophosphate, deoxynucleoside diphosphate and deoxynucleoside triphosphate.

95. The fluorescently labeled reagent according to claim 94 wherein the deoxynucleotides are selected from the group consisting of deoxycytosine, deoxyadenosine, deoxyguanosine, and deoxythymidine.

96. The fluorescently labeled reagent according to claim 80 wherein the reagent is selected from the group consisting of dideoxynucleoside, dideoxynucleoside monophosphate, dideoxynucleoside diphosphate and dideoxynucleoside triphosphate.

97. The fluorescently labeled reagent according to claim 96 wherein the dideoxynucleotides are selected from the group consisting of dideoxycytosine, dideoxyadenosine, dideoxyguanosine, and dideoxythymidine.

98. The fluorescently labeled reagent according to claim 80 wherein the reagent is an oligonucleotide.

99. The fluorescently labeled reagent according to claim 80 wherein the oligonucleotide has a 3' end which is extendable by using a polymerase.

100. A method for sequencing a nucleic acid sequence comprising:
  forming a mixture of extended labeled primers by hybridizing a nucleic acid sequence with a fluorescently labeled oligonucleotide primer in the presence of deoxynucleoside triphosphates, at least one dideoxynucleoside triphosphate and a DNA polymerase, the DNA polymerase extending the primer with the deoxynucleoside triphosphates until a dideoxynucleoside triphosphate is incorporated which terminates extension of the primer;

separating the mixture of extended primers; and determining the sequence of the nucleic acid sequence by fluorescently measuring the mixture of extended primers formed;

the fluorescently labeled oligonucleotide primer including an oligonucleotide sequence complementary to a portion of the nucleic acid sequence being sequenced and having a 3' end extendable by a polymerase, and an energy transfer fluorescent dye attached to the oligonucleotide, the energy transfer fluorescent dye including a donor dye capable of absorbing light at a first wavelength and emitting excitation energy in response, an acceptor dye capable of absorbing the excitation energy emitted by the donor dye and fluorescing at a second wavelength in response, and a linker linking the donor dye to the acceptor dye such that the acceptor dye absorbs substantially all of the excitation energy emitted by the donor dye, the linker including a functional group selected from the group consisting of an alkene, diene, alkyne, a five and six membered ring having at least one unsaturated bond or a fused ring structure.

101. The method according to claim 100 wherein the energy transfer fluorescent dye has the structure:

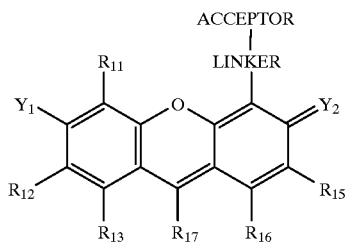

wherein $Y_1$ and $Y_2$ are each independently selected from the group consisting of hydroxyl, oxygen, iminium and amine; and $R_{11}$–$R_{13}$ and $R_{15}$–$R_{17}$ are each independently selected from the group consisting of hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof.

102. The method according to claim 100 wherein the energy transfer fluorescent dye has the structure:

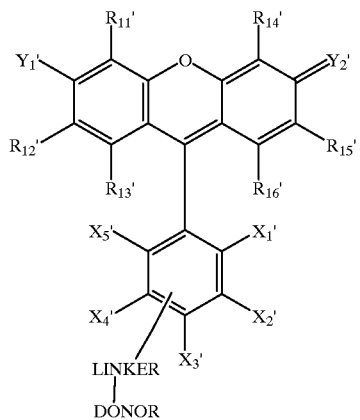

wherein $Y_1'$ and $Y_2'$ are each independently selected from the group consisting of hydroxyl, oxygen, iminium and amine;

$R_{11}'$–$R_{16}'$ are each independently selected from the group consisting of hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof;

$X_1'$–$X_5'$ are selected to correspond to an acceptor dye which is capable of absorbing the excitation energy emitted by the donor dye and fluorescing at a second wavelength in response; and one of $X_3'$ and $X_4'$ includes the linker.

103. The method according to claim 100 wherein the energy transfer fluorescent dye has the structure:

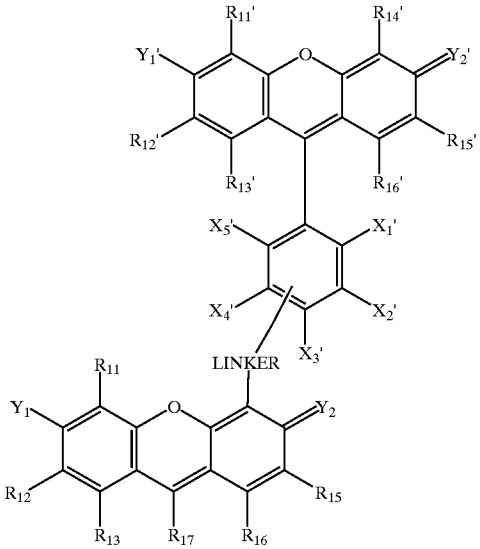

wherein:

$Y_1$, $Y_1'$, $Y_2$ and $Y_2'$ are each independently selected from the group consisting of hydroxyl, oxygen, iminium and amine;

$R_{11}$–$R_{13}$, $R_{15}$–$R_{17}$ and $R_{11}'$–$R_{16}'$ are each independently selected from the group consisting of hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof;

$X_1'$–$X_5'$ are each independently selected from the group consisting of hydrogen, fluorine, chlorine, bromine, iodine, carboxyl, alkyl, alkene, alkyne, sulfonate, amino, ammonium, amido, nitrile, alkoxy, where adjacent substituents are taken together to form a ring, and combinations thereof;

$Y_1$, $Y_2$, $R_{11}$–$R_{13}$ and $R_{15}$–$R_{17}$ are selected to correspond to a donor dye capable of absorbing light at a first wavelength and emitting excitation energy in response;

$Y_1'$, $Y_2'$, $R_{11}'$–$R_{16}'$, and $X_1'$–$X_5'$ are selected to correspond to an acceptor dye which is capable of absorbing the excitation energy emitted by the donor dye and fluorescing at a second wavelength in response; and one of $X_3'$ and $X_4'$ includes the linker.

104. The method according to claim 100 wherein the energy transfer fluorescent dye has the structure:

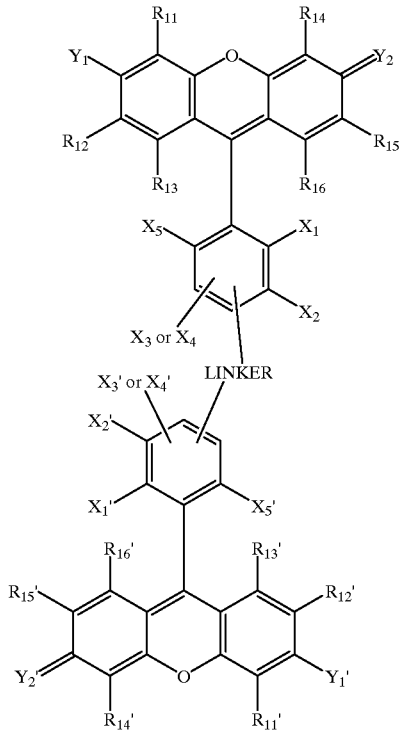

wherein:

$Y_1$, $Y_1'$, $Y_2$ and $Y_2'$ are each independently selected from the group consisting of hydroxyl, oxygen, iminium and amine;

$R_{11}$–$R_{16}$ and $R_{11}'$–$R_{16}'$ are each independently selected from the group consisting of hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof;

$X_1$–$X_5$ and $X_1'$–$X_5'$ are each independently selected from the group consisting of hydrogen, fluorine, chlorine, bromine, iodine, carboxyl, alkyl, alkene, alkyne, sulfonate, amino, ammonium, amido, nitrile, alkoxy, where adjacent substituents are taken together to form a ring, and combinations thereof;

$Y_1$, $Y_2$, $R_{11}$–$R_{16}$ and $X_1$–$X_5$ are selected to correspond to a donor dye capable of absorbing light at a first wavelength and emitting excitation energy in response;

$Y_1'$, $Y_2'$, $R_{11}'$–$R_{16}'$, and $X_1'$–$X_5'$ are selected to correspond to an acceptor dye which is capable of absorbing the excitation energy emitted by the donor dye and fluorescing at a second wavelength in response; and one of $X_3$ and $X_4$ and one of $X_3'$ and $X_4'$ are taken together to form the linker.

105. A method for sequencing a nucleic acid sequence comprising:

forming a mixture of extended primers by hybridizing a nucleic acid sequence with a primer in the presence of deoxynucleoside triphosphates, at least one fluorescently labeled dideoxynucleoside triphosphate and a DNA polymerase, the DNA polymerase extending the primer with the deoxynucleoside triphosphates until a fluorescently labeled dideoxynucleoside triphosphate is incorporated onto the extended primer which terminates extension of the primer;

separating the mixture of extended primers; and determining the sequence of the nucleic acid sequence by detecting the fluorescently labeled dideoxynucleotide attached to the separated mixture of extended primers;

the fluorescently labeled dideoxynucleoside triphosphate including a dideoxynucleoside triphosphate, and an energy transfer fluorescent dye attached to the dideoxynucleoside triphosphate, the energy transfer dye including a donor dye capable of absorbing light at a first wavelength and emitting excitation energy in response, an acceptor dye capable of absorbing the excitation energy emitted by the donor dye and fluorescing at a second wavelength in response, and a linker linking the donor dye to the acceptor dye such that the acceptor dye absorbs substantially all of the excitation energy emitted by the donor dye, the linker including a functional group selected from the group consisting of an alkene, diene, alkyne, a five and six membered ring having at least one unsaturated bond or a fused ring structure.

106. The method according to claim 105 wherein the energy transfer fluorescent dye has the structure:

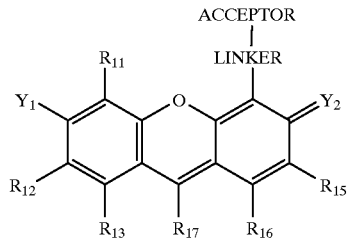

wherein $Y_1$ and $Y_2$ are each independently selected from the group consisting of hydroxyl, oxygen, iminium and amine; and $R_{11}$–$R_{13}$ and $R_{15}$–$R_{17}$ are each independently selected from the group consisting of hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof.

107. The method according to claim 105 wherein the energy transfer fluorescent dye has the structure:

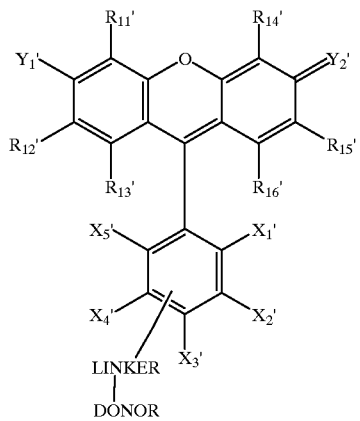

wherein $Y_1'$ and $Y_2'$ are each independently selected from the group consisting of hydroxyl, oxygen, iminium and amine;

$R_{11}'$–$R_{16}'$ are each independently selected from the group consisting of hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof;

$X_1'$–$X_5'$ are selected to correspond to an acceptor dye which is capable of absorbing the excitation energy emitted by the donor dye and fluorescing at a second wavelength in response; and one of $X_3'$ and $X_4'$ includes the linker.

108. The method according to claim 105 wherein the energy transfer fluorescent dye has the structure:

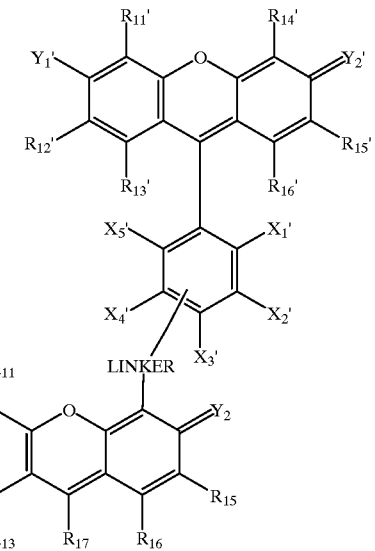

wherein:

$Y_1$, $Y_1'$, $Y_2$ and $Y_2'$ are each independently selected from the group consisting of hydroxyl, oxygen, iminium and amine;

$R_{11}$–$R_{13}$, $R_{15}$–$R_{17}$ and $R_{11}'$–$R_{16}'$ are each independently selected from the group consisting of hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof;

$X_1'$–$X_5'$ are each independently selected from the group consisting of hydrogen, fluorine, chlorine, bromine, iodine, carboxyl, alkyl, alkene, alkyne, sulfonate, amino, ammonium, amido, nitrile, alkoxy, where adjacent substituents are taken together to form a ring, and combinations thereof;

$Y_1$, $Y_2$, $R_{11}$–$R_{13}$ and $R_{15}$–$R_{17}$ are selected to correspond to a donor dye capable of absorbing light at a first wavelength and emitting excitation energy in response;

$Y_1'$, $Y_2'$, $R_{11}'$–$R_{16}'$, and $X_1'$–$X_5'$ are selected to correspond to an acceptor dye which is capable of absorbing the excitation energy emitted by the donor dye and fluorescing at a second wavelength in response; and one of $X_3'$ and $X_4'$ includes the linker.

109. The method according to claim 100 wherein the energy transfer fluorescent dye has the structure:

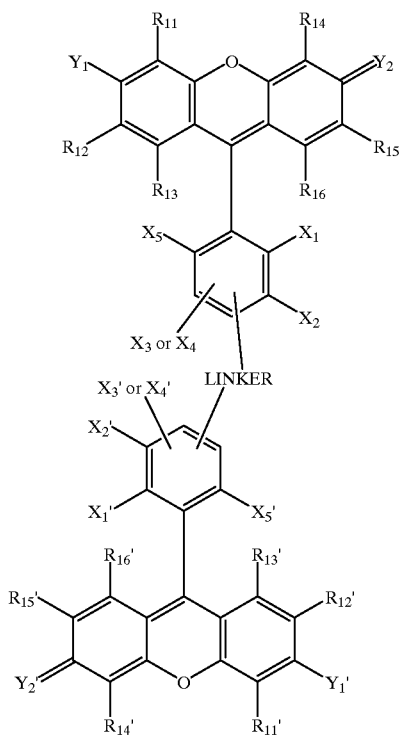

wherein:

$Y_1$, $Y_1'$, $Y_2$ and $Y_2'$ are each independently selected from the group consisting of hydroxyl, oxygen, iminium and amine;

$R_{11}$–$R_{16}$ and $R_{11}'$–$R_{16}'$ are each independently selected from the group consisting of hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof;

$X_1$–$X_5$ and $X_1'$–$X_5'$ are each independently selected from the group consisting of hydrogen, fluorine, chlorine, bromine, iodine, carboxyl, alkyl, alkene, alkyne, sulfonate, amino, ammonium, amido, nitrile, alkoxy, where adjacent substituents are taken together to form a ring, and combinations thereof;

$Y_1$, $Y_2$, $R_{11}$–$R_{16}$, and $X_1$–$X_5$ are selected to correspond to a donor dye capable of absorbing light at a first wavelength and emitting excitation energy in response;

$Y_1'$, $Y_2'$, $R_{11}'$–$R_{16}'$, and $X_1'$–$X_5'$ are selected to correspond to an acceptor dye which is capable of absorbing the excitation energy emitted by the donor dye and fluorescing at a second wavelength in response; and one of $X_3$ and $X_4$ and one of $X_3'$ and $X_4'$ are taken together to form the linker.

* * * * *

UNITED STATES PATENT AND TRADEMARK OFFICE
CERTIFICATE OF CORRECTION

PATENT NO.   : 5,945,526
DATED        : August 31, 1999
INVENTOR(S)  : Lee, Linda G., Spurgeon, Sandra L. and Rosenblum, Barnett It is certified that error appears in the above-identified patent and that said Letters Patent is hereby corrected as shown below:

Title page,
Item [63], please amend the paragraph to read as follows:
-- Continuation of application No. 08/726,462, Oct. 4, 1996, Pat. No. 5,800,996, which is a continuation-in-part of application No. 08/642,330, May 3, 1996, Pat. No. 5,863,727, and application No. 08/672,196, Jun. 27, 1996, Pat. No. 5,847,162. --

Signed and Sealed this

Twenty-fifth Day of February, 2003

JAMES E. ROGAN
*Director of the United States Patent and Trademark Office*

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 1217 nucleotides
      (B) TYPE: nucleic acid
      (C) STRANDEDNESS: single
      (D) TOPOLOGY: linear (xi) SEQUENCE DESCRIPTION: SEQ ID NO: 1:

```
GCCAAGCTTG   CATGCCTGCA   GGTCGACTCT   AGAGGATCCC         40

CGGGTACCGA   GCTCGAATTC   GTAATCATGG   TCATAGCTGT         80

TTCCTGTGTG   AAATTGTTAT   CCGCTCACAA   TTCCACACAA        120

CATACGAGCC   GGAAGCATAA   AGTGTAAAGC   CTGGGGTGCC        160

TAATGAGTGA   GCTAACTCAC   ATTAATTGCG   TTGCGCTCAC        200

TGCCCGCTTT   CCAGTCGGGA   AACCTGTCGT   GCCAGCTGCA        240
```

```
TTAATGAATC  GGCCAACGCG  CGGGGAGAGG  CGGTTTGCGT         280

ATTGGGCGCC  AGGGTGGTTT  TTCTTTTCAC  CAGTGAGACG         320

GGCAACAGCT  GATTGCCCTT  CACCGCCTGG  CCCTGAGAGA         360

GTTGCAGCAA  GCGGTCCACG  CTGGTTTGCC  CCAGCAGGCG         400

AAAATCCTGT  TTGATGGTGG  TTCCGAAATC  GGCAAAATCC         440

CTTATAAATC  AAAAGAATAG  CCCGAGATAG  GGTTGAGTGT         480

TGTTCCAGTT  TGGAACAAGA  GTCCACTATT  AAAGAACGTG         520

GACTCCAACG  TCAAAGGGCG  AAAAACCGTC  TATCAGGGCG         560

ATGGCCCACT  ACGTGAACCA  TCACCCAAAT  CAAGTTTTTT         600

GGGGTCGAGG  TGCCGTAAAG  CACTAAATCG  GAACCCTAAA         640

GGGAGCCCCC  GATTTAGAGC  TTGACGGGGA  AAGCCGGCGA         680

ACGTGGCGAG  AAAGGAAGGG  AAGAAAGCGA  AAGGAGCGGG         720

CGCTAGGGCG  CTGGCAAGTG  TAGCGGTCAC  GCTGCGCGTA         760

ACCACCACAC  CCGCCGCGCT  TAATGCGCCG  CTACAGGGCG         800

CGTACTATGG  TTGCTTTGAC  GAGCACGTAT  AACGTGCTTT         840

CCTCGTTGGA  ATCAGAGCGG  GAGCTAAACA  GGAGGCCGAT         880

TAAAGGGATT  TTAGACAGGA  ACGGTACGCC  AGAATCTTGA         920

GAAGTGTTTT  TATAATCAGT  GAGGCCACCG  AGTAAAAGAG         960

TCTGTCCATC  ACGCAAATTA  ACCGTTGTAG  CAATACTTCT        1000

TTGATTAGTA  ATAACATCAC  TTGCCTGAGT  AGAAGAACTC        1040

AAACTATCGG  CCTTGCTGGT  AATATCCAGA  ACAATATTAC        1080

CGCCAGCCAT  TGCAACAGGA  AAAACGCTCA  TGGAAATACC        1120

TACATTTTGA  CGCTCAATCG  TCTGAAATGG  ATTATTTACA        1160

TTGGCAGATT  CACCAGTCAC  ACGACCAGTA  ATAAAAGGGA        1200

CATTCTGGCC  AACAGAG                                  1217

(2) INFORMATION FOR SEQ ID NO: 2:

(i) SEQUENCE CHARACTERISTICS:
        (A) LENGTH: 18 nucleotides
        (B) TYPE: nucleic acid
        (C) STRANDEDNESS:  single
        (D) TOPOLOGY:  linear (xi) SEQUENCE DESCRIPTION: SEQ ID NO: 2:

TGTAAAACGA  CGGCCAGT                                    18

(2) INFORMATION FOR SEQ ID NO: 3:

(i) SEQUENCE CHARACTERISTICS:
        (A) LENGTH: 738 nucleotides
        (B) TYPE: nucleic acid
        (C) STRANDEDNESS:  single
        (D) TOPOLOGY:  linear (xi) SEQUENCE DESCRIPTION: SEQ ID NO: 3:

ATACGACTCA  CTATAGGGCG  AATTCGAGCT  CGGTACCCGG          40

GGATCCTCTA  GAGTCGACCT  GCAGGCATGC  AAGCTTGAGT          80

ATTCTATAGT  GTCACCTAAA  TAGCTTGGCG  TAATCATGGT         120
```

-continued

| | | | | |
|---|---|---|---|---|
| CATAGCTGTT | TCCTGTGTGA | AATTGTTATC | CGCTCACAAT | 160 |
| TCCACACAAC | ATACGAGCCG | GAAGCATAAA | GTGTAAAGCC | 200 |
| TGGGGTGCCT | AATGAGTGAG | CTAACTCACA | TTAATTGCGT | 240 |
| TGCGCTCACT | GCCCGCTTTC | CAGTCGGGAA | ACCTGTCGTG | 280 |
| CCAGCTGCAT | TAATGAATCG | GCCAACGCGC | GGGGAGAGGC | 320 |
| GGTTTGCGTA | TTGGGCGCTC | TTCCGCTTCC | TCGCTCACTG | 360 |
| ACTCGCTGCG | CTCGGTCGTT | CGGCTGCGGC | GAGCGGTATC | 400 |
| AGCTCACTCA | AAGGCGGTAA | TACGGTTATC | CACAGAATCA | 440 |
| GGGGATAACG | CAGGAAAGAA | CATGTGAGCA | AAAGGCCAGC | 480 |
| AAAAGGCCAG | GAACCGTAAA | AAGGCCGCGT | TGCTGGCGTT | 520 |
| TTTCCATAGG | CTCCGCCCCC | CTGACGAGCA | TCACAAAAAT | 560 |
| CGACGCTCAA | GTCAGAGGTG | GCGAAACCCG | ACAGGACTAT | 600 |
| AAAGATACCA | GGCGTTTCCC | CCTGGAAGCT | CCCTCGTGCG | 640 |
| CTCTCCTGTT | CCGACCCTGC | CGCTTACCGG | ATACCTGTCC | 680 |
| GCCTTTCTCC | CTTCGGGAAG | CGTGGCGCTT | TCTCATAGCT | 720 |
| CACGCTGTAG | GTATCTCA | | | 738 |